US011401519B2

(12) United States Patent
Watts et al.

(10) Patent No.: US 11,401,519 B2
(45) Date of Patent: Aug. 2, 2022

(54) ANTI-ADAM33 OLIGONUCLEOTIDES AND RELATED METHODS

(71) Applicants: UNIVERSITY OF MASSACHUSETTS, Boston, MA (US); UNIVERSITY OF SOUTHAMPTON, Southampton (GB)

(72) Inventors: Jonathan Watts, Worcester, MA (US); Hans Michael Haitchi, Southampton (GB); Hannah Pendergraff, Kongens Lyngby (DK)

(73) Assignees: UNIVERSITY OF MASSACHUSETTS, Boston, MA (US); UNIVERSITY OF SOUTHAMPTON

( * ) Notice: Subject to any disclaimer, the term of this patent is extended or adjusted under 35 U.S.C. 154(b) by 111 days.

(21) Appl. No.: 16/001,265

(22) Filed: Jun. 6, 2018

(65) Prior Publication Data

US 2019/0002885 A1    Jan. 3, 2019

Related U.S. Application Data

(60) Provisional application No. 62/516,315, filed on Jun. 7, 2017.

(51) Int. Cl.
   *C12N 15/113*    (2010.01)

(52) U.S. Cl.
   CPC ...... *C12N 15/1137* (2013.01); *C12N 2310/11* (2013.01); *C12N 2310/111* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/344* (2013.01); *C12N 2310/351* (2013.01); *C12N 2310/3513* (2013.01); *C12N 2310/3515* (2013.01); *C12Y 304/24* (2013.01)

(58) Field of Classification Search
   CPC ........ C12N 2310/321; C12N 2310/322; C12N 2310/33; C12N 2310/34; C12N 2310/35; C12N 2310/3525; C12N 2310/3527; C12N 2310/341; C12N 2310/346
   USPC ........... 435/6.1, 6.11, 91.1, 91.31, 455, 458; 514/44 A; 536/23.1, 24.5
   See application file for complete search history.

(56) References Cited

U.S. PATENT DOCUMENTS

| 5,684,143 | A | 11/1997 | Gryaznov |
| 5,858,988 | A | 1/1999 | Wang |
| 6,291,438 | B1 | 9/2001 | Wang |
| 7,399,845 | B2 | 7/2008 | Punith |
| 7,427,672 | B2 | 9/2008 | Imanishi |
| 2004/0002470 | A1 | 1/2004 | Keith et al. |
| 2004/0171570 | A1 | 9/2004 | Allerson et al. |
| 2005/0130923 | A1 | 6/2005 | Balkrishen et al. |
| 2005/0164968 | A1 | 7/2005 | Mscwiggen et al. |
| 2011/0039914 | A1 | 2/2011 | Pavco et al. |
| 2015/0164968 | A1* | 6/2015 | Otani ................ C12P 17/10 424/777 |
| 2015/0252364 | A1* | 9/2015 | Krieg ................ A61K 31/7088 514/44 A |
| 2020/0362353 | A1* | 11/2020 | Bennett ................ A61P 21/00 |

FOREIGN PATENT DOCUMENTS

| WO | 99/14226 A2 | 3/1999 |
| WO | 03/004602 A2 | 1/2003 |
| WO | WO 2003/030832 A2 | 4/2003 |
| WO | 2007134181 A2 | 11/2007 |
| WO | 2008101157 A1 | 8/2008 |
| WO | 2008148120 A1 | 12/2008 |
| WO | 2008154401 A2 | 12/2008 |
| WO | 2009006478 A2 | 1/2009 |
| WO | WO 2014/076195 A1 | 5/2014 |
| WO | WO 2014/118267 A1 | 8/2014 |
| WO | WO 2014/179620 A1 | 11/2014 |
| WO | WO-2015021457 A2 * | 2/2015 | ............. A61P 21/02 |

OTHER PUBLICATIONS

Pendergraff et al (Poster, Oligonucleotide Therapeutics Society 12th Annual Meeting, Leiden, Netherlands (Oct. 2015) (Year: 2015).*
Fiszer et al. (2011) "Inhibition of mutant huntingtin expression by RNA duplex targeting expanded CAG repeats," Nucleic Acids Res., 39:5578-5585.
Gagnon et al. (2010) "Allele-selective inhibition of mutant huntingtin with antisense oligonucleotides targeting the expanded CAG repeat," Biochemistry, 49:10166-10178.
Hu et al. (2009) "Allele-specific silencing of mutant huntingtin and ataxin-3 genes by targeting expanded CAG repeats in mRNAs," Nat. Biotechnol., 27:478-484.
Powell et al. (2004) "The splicing and fate of ADAM33 transcripts in primary human airways fibroblasts," Am. J. Respir. Cell Mol. Biol., 31:13-21.
Suzuki et al. (2010) "An upstream open reading frame and the context of the two AUG codons affect the abudance of mitochondrial and nuclear RNase H1," Mol. Cell. Biol. 30:5123-5134.
Lima et al. (2016) "Viable RNaseH1 knockout mice show RNaseH1 is essential for R loop processing, mitochondrial and liver function," Nucleic Acids Res., 44:5299-5312.

(Continued)

*Primary Examiner* — Jane J Zara
(74) *Attorney, Agent, or Firm* — Lathrop GPM LLP; James H. Velema, Esq.; Michael J. Spellberg, Esq.

(57) ABSTRACT

The present disclosure provides antisense compounds, methods, and compositions for silencing ADAM33 mRNA. The present disclosure provides antisense compounds, methods, and compositions for the treatment, prevention, or amelioration of diseases, disorders, and conditions associated with ADAM33 in a subject in need thereof. Also contemplated are antisense compounds and methods for the preparation of a medicament for the treatment, prevention, or amelioration of a disease, disorder, or condition associated with ADAM33.

48 Claims, 9 Drawing Sheets

Specification includes a Sequence Listing.

(56) References Cited

OTHER PUBLICATIONS

Hori et al. (2015) "XRN2 is required for the degradation of target RNAs by RNase H1-dependent antisense oligonucleotides," Biochem. Biophys. Res. Commun., 464:506-511.
Kamola et al. (2015) "In silico and in vitro evaluation of exonic and intronic off-target effects form a critical element of therapeutic ASO gapmer optimization," Nucleic Acids Res., 43:8638-8640.
Burel et al. (2016) "Hepatotoxicity of high affinity gapmer antisense oligonucleotides is mediated by RNase H1 dependent promiscuous reduction of very long pre-mRNA transcripts," Nucleic Acids Res., 44:2093-2109.
Kasuya et al. (2016) "Ribonuclease H1-dependent hepatotoxicity caused by locked nucleic acid-modified gapmer antisense oligonucleotides," Sci. Rep., 6:30377.
Lennox et al. (2016) "Cellular localization of long non-coding RNAs affects silencing by RNAi more than by antisense oligonucleotides," Nucleic Acids Res., 44:863-877.
Castanotto et al. (2015) "A cytoplasmic pathway for gapmer antisense oligonucleotide-mediated gene silencing in mammalian cells," Nucleic Acids Res., 43:9350-9361.
Gagnon et al. (2014) "RNAi factors are present and active in human cell nuclei," Cell Rep., 6:211-221.
Wang et al. (2009) "Association of ADAM33 gene polymorphisms with COPD in a northeastern Chinese population," BMC Med. Genet., 10.
Figarska et al. (2013) "ADAM33 Gene Polymorphisms and Mortality," A Prospective Cohort Study, PLoS One, 8.
Shaffiq et al. (2012) "A disintegrin and metalloprotease (ADAM) 33 protein in patients with pulmonary sarcoidosis," Respirology, 17:342-349.
Koshkin et al. (1998) "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 54:3607-3630.
Chillemi et al. (2013) "Oligonucleotides Conjugated to Natural Lipids: Synthesis of Phosphatidyl-Anchored Antisense Oligonucleotides," Bioconj. Chem., 24:648-657.
Martin et al. (1995) "A New Access to 2'-0-Alkylated Ribonucleosides and Properties of 2'-O-Alkylated Oligoribonucleotides," Helv. Chim. Acta., 78:486-504.
Herdewijn et al. (2000) "Heterocyclic modifications of oligonucleotides and antisense technology," Antisense Nucleic Acid Drug Dev., 10(4):297-310.
Eckstein, Fritz (2000) "Phosphorothioate Oligodeoxynucleotides: What is Their Origin and What Is Unique About Them?," Antisense Nucleic Acid Drug Dev., 10:117-121.
Rusckowski et al. (2001) "Biodistribution and Metabolism of a Mixed Backbone Oligonucleotide (GEM 231) Following Single and Multiple Dose Administration in Mice," Antisense Nucleic Acid Drug Dev., 10:333-345.
Stein et al. (2001) "Inhibition of Vesivirus Infections in Mammalian Tissue Culture with Antisense Morpholino Oligomers," Antisense Nucleic Acid Drug Dev., 11(5):317-325.
Vorobjev et al. (2001) "Nuclease Resistance and RNase H Sensitivity of Oligonucleotides Bridged by Oligomethylenediol and Oligoethylene Glycol Linkers," Antisense Nucleic Acid Drug Dev., 11:77-85.
Leumann, J. C. (2002) "DNA Analogues: From Supramolecular Principles to Biological Properties," Bioorganic and Medicinal Chemistry, 10:841-854.
Ittig et al. (2004) "Nuclear antisense effects in cyclophilin A pre-mRNA splicing by oligonucleotides: a comparison of tricyclo-DNA with LNA," Nucleic Acids Res., 32:346-353.
Ittig et al. (2005) Prague, Academy of Sciences of the Czech Republic, 7:21-26, (Coll. Symp. Series, Hocec, M., 2005).
Ivanova et al. (2007) "Tricyclo-DNA Containing Oligonucleotides as Steric Block Inhibitors of Human Immunodeficiency Virus Type 1 Tat-Dependent Trans-Activation and HIV-1 Infectivity," Oligonucleotides, 17:54-65.

Renneberg et al. (2002) "Antisense properties of tricyclo-DNA," Nucleic Acids Res., 30:2751-2757.
Renneberg et al. (2004) "Exploring Hoogsteen and Reversed-Hoogsteen Duplex and Triplex Formation with Tricyclo-DNA Purine Sequences," Chembiochem, 5:1114-1118.
Renneberg et al. (2002) "Watson-Crick Base-Pairing Properties of Tricyclo-DNA," JACS, 124:5993-6002.
Sorenson et al. (2002) "α-L-ribo-Configured Locked Nucleic Acid (α-L-LNA): Synthesis and Properties," J. Am. Chem. Soc., 124(10):2164-2176.
Woolf et al. (1992) "Specificity of antisense oligonucleotides in vivo," Proc. Natl. Acad. Sci. USA, 89:7305-7309.
Gautschi et al. (2001) "Activity of a Novel bcl-2/bcl-xL-Bispecific Antisense Oligonucleotide Against Tumors of Diverse Histologic Origins," J. Natl. Cancer Inst., 93:463-471.
Maher and Dolnick (1988) "Comparative hybrid arrest by tandem antisense oligodeoxyribonucleotides or oligodeoxy-ribonucleoside methylphosphonates in a cell-free system," Nuc. Acid. Res., 16:3341-3358.
Werner et al. (2004) "Asthma is associated with single-nucletodie polymorphisms in ADAM33," Clin. Exp. Allergy, 34(1):26-31.
Sharma et al. (2011) "Role of ADAM33 gene and associated single nucleotide polymorphisms in asthma," Allergy Rhinol (Providence) 2(2):e63-e70.
Al-Khayyat et al. (2012) "T1 and T2 ADAM33 single nucleotide polymorphisms and the risk of childhood asthma in a Saudi Arabian population: a pilot study," Ann. Saudi. Med., 32(5):479-486.
Martinez et al. (2016) "Single nucleotide polymorphisms V4 and T1 of the ADAM33 gene in Venezuelan with asthma or chronic obstructive pulmonary disease," Invest Clin., 57(2): 176-186, with English abstract.
Saad-Hussein et al. (2015) "Association of ADAM33 gene polymorphism and arginase activity with susceptibility to ventilatory impairment in wood dust-exposed workers," Human Exp. Toxicol, 35(9):966-973.
Han et al. (2014) "Association of ADAM33 Gene Polymorphisms with Keloid Scars in a Northeastern Chinese Population," Cell. Phys. Biochem., 34:981-987.
Kim et al. (2016) "ADAM33 Polymorphisms Are Associated with Susceptibilty to Systemic Lupus Erythematosus in a Korean Population," J. Rheum. Dis., 23(2):88-95.
Zihilif et al. (2013) "Frequency of genetic polymorphisms of ADAM33 ad their association with allergic rhinitis among Jordanians," Gene, 531(2):462-466.
Chen et al. (2014) "Association Study on ADAM33 Polymorphisms in Mite-Sensitized Persisten Allergic Rhinits in a Chinese Population," PLoS One, 9(4):e95033.
Uh et al. (2014) "ADAM33 Gene Polymorphisms are Associated with the Risk of Idiooathic Pulmonary Fibrosis," Lung, 192(4):525-532.
Davies et al. (2016) "Soluble ADAM33 intiates airway remodeling to promote susceptibility for allergic asthma in early life," JCI Insight, 1(11):e87632, 17 pages.
Watts, J.K. (2013) "2'-Flourinated oligonucleotides: High binding affinity and novel applications," Oral Presentation at EuroTIDES, Prague, Nov. 2013.
Watts, J.K. (2014) "2'-Flourinated oligonucleotides:Conformational control and high binding affinity," Presented at the RSC Organic Division Southwest Regional Meeting, Oxford, Feb. 2014.
Pendergraff, H.M. (2014) "Novel oligonucleotides for asthma research and therapy," Poster presentation at the IS3NA's "XXI International Roundtable on Nucleosides, Nucleotides and Nucleic Acids," Poznan, Poland, Aug. 2014.
Pendergraff, H.M. (2015) "Single-stranded oligonucleotides and conjugates for silencing a nuclear-retained mRNA implicated in asthma," Poster presented at the Oligonucleotide Therapeutics Society's 12th annual meeting (Leiden, Netherlands, Oct. 2015).
Pendergraff, H.M. (2016) "A comparison of single-stranded oligonucleotides and conjugates for silencing asthma-associated protease ADAM33," Poster presentation at the RSC's 12th Nucleic Acids Forum, (London, UK, Jul. 2016).

(56) References Cited

OTHER PUBLICATIONS

Koppelman et al. (2011) "Evidence of a genetic contribution to lung function decline in asthma," J. Allergy Clin. Immunol., 128:479-484.
Tang et al. (2006) "Airway remodelling in asthma: Current understanding and implications for future therapies," Pharmacol Ther., 112:474-488.
Global Asthma Network, The Global Asthma Report 2014; globalasthmareport.org.
Erdewegh et al. (2002) "Association of the ADAM33 gene with asthma and bronchial hyperresponsiveness," Nature, 418:426-430.
Lee et al. (2004) "ADAM33 polymorphism: association with bronchial hyper-responsiveness in Korean asthmatics," Clin. Exp. Allergy, 34:860-865.
Lee et al. (2006) "A disintegrin and metalloproteinase 33 protein in patients with asthma—Relevance to airflow limitation," Am. J. Respir. Crit. Care Med., 173:729-735.
Puxeddu et al. (2008) "The soluble form of a disintegrin and metalloprotease 33 promotes angiogenesis: Implications for airway remodeling in asthma," Journal of Allergy and Clinical Immunology, 121:1400-1406.
Coussens et al. (2002) "Matrix metalloproteinase inhibitors and cancer: trials and tribulations," Science, 295:2387-2392.
Khorova et al. (2017) "The chemical evolution of oligonucleotide therapies of clinical utility," Nat. Biotechnol., in press, DOI: 10.038/nbt.3765.
Yu et al. (2012) "Single-stranded RNAs Use RNAi to Potently and Allele-Selectively Inhibit Mutant Huntingtin Expression," Cell 150:895-908.
Lima et al. (2012) "Single-Stranded siRNAs Activate RNAi in Animals," Cell, 150:883-894.
Wahlestedt et al. (2000) "Potent and nontoxic antisense oligonucleotides containing locked nucleic acids," Proc. Natl. Acad. Sci. USA, 97:5633-5638.
Kurreck et al. (2002) "Design of antisense oligonucleotides stabilized by locked nucleci acids," Nucleic Acids Res., 30:1911-1918.
Fluiter et al. (2009) "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 5:838-843.
Stein et al. (2010) "Efficient gene silencing by delivery of locked nucleic acid antisense oligonucleotides, unassisted by transfection reagents," Nucleic Acids Res., 38:e3.
Kini et al. (2007) "In vitro binding of single-stranded RNA by human Dicer," FEBS Lett., 581:5611-5616.
Holen et al. (2003) "Similar behaviour of single-strand and double-strand siRNAs they act through a common RNAi pathway," Nucleic Acids Res., 31:2401-2407.
Monia et al. (1993) "Evaluation of 2'-modified oligonucleotides containing 2'-deoxy gaps as antisense inhibitors of gene expression," J. Biol. Chem., 268:14514-14522.
Inoue et al. (1987) "Sequence-dependent hydrolysis of RNA using modified oligonucleotide splints and RNase H," FEBS Lett., 215:327-330.
Agrawal et al. (1995) "Absorption, tissue distribution and in vivo stability in rats of a hybrid antisense oligonucleotide following oral administration," Biochem. Pharmacol., 50:571-576.
Juliano et al. (2014) "Cellular Uptake and Intracellular Trafficking of Oligonucleotides: Implications for Oligonucleotide Pharmacology," Nucl. Acid. Ther., 24:101-113.
Bennet et al. (2010) "RNA Targeting Therapeutics: Molecular Mechanisms of Antisense Oligonucleotides as a Therapeutic Platform," Annu. Rev. Pharmacol. Toxicol 50:259-93.
Watts et al. (2012) "Silencing disease genes in the laboratory and the clinic," J. Pathol., 226:365-379.
Souleimanian et al. (2012) "Antisense 2'-Deoxy, 2'-Fluoroarabino Nucleic Acid (2' F-ANA) Oligonucleotides: In Vitro Gymnotic Silencers of Gene Expression Whose Potency is Enhanced by Fatty Acids," Mol. Ther. Nucl. Acids, 1: e43.

Soifer et al. (2012) "Silencing of Gene Expression by Gymnotic Delivery of Antisense Oligonucleotides," In Functional Genomics: Methods and Protocols, Second Edition, Kaufmann, M.; Klinger, C., Eds. Humana Press Inc: Totowa, 2012; vol. 815, pp. 333-346.
Winkler et al. (2013) "Oligonucleotide conjugates for therapeutic applications," Ther. Deliv., 4:791-809.
Wolfrum et al. (2007) "Mechanisms and optimization of in vivo delivery of lipophilic siRNAs," Nat. Biotechnol., 25:1149-1157.
Hostetler et al. (2001) "In vitro and in vivo activity of 1-O-hexadecylpropane-diol-3-phospho-ganciclovir and 1-O-hexadecylpropane-diol-3-phospho-penciclovir in cytomegalovirus and herpes simplex virus infections," Antiviral Chem. Chemother., 12:61-70.
Prakash et al. (2014) "Targeted delivery of antisense oligonucleotides to hepatocytes using triantennary N-acetyl galactosamine improves potency 10-fold in mice," Nucleic Acids Res., 42:8796-8807.
Aldern e tal. (2003) "Increased antiviral activity of 1-O-hexadecyloxypropyl-2-C-14 cidofovirin MRC-5 human lung fibroblasts is explained by unique cellular uptake and metabolism," Mol. Pharmacol., 63:678-681.
Hostetler et al. (2009) "Alkoxyalkyl prodrugs of acyclic nucleotide phoshonates enhance oral antiviral activity and reduce toxicity: Current state of the art," Antiviral Res., 82:A84-A98.
Yamano et al. (2012) "Lipophilic amines as potent inhibitors of N-acylethanolamine-hydrolyzing acid amidase," Biorg. Med. Chem., 20:3658-3665.
Edwardson et al. (2014) "An efficient and modular route to sequence-defined polymers appended to DNA," Angew. Chem. Int. Ed. Engl., 53:4567-4571.
Banga et al. (2014) "Liposomal Spherical Nucleic Acids," Journal of the American Chemical Society, 136:9866-9869.
Essat et al. (2015) "Self-Assembly into Nanoparticles is Essential for Receptor Mediated Uptake of Therapeutic Antisense Oligonucleotides," Nano Lett., 15:4364-4373.
Subramanian et al. (2015) "Enhancing antisense efficacy with multimers and multi-targeting oligonucleotides (MTOs) using cleavable linkers," Nucleic Acids Res., 43:9123-9132.
Nishina et al. (2015) "Chimeric Antisense Oligonucleotide Conjugated to aplha-Tocopherol," Mol. Ther. Nucl. Acids, 4:e220.
Notredame et al. (2000) "T-Coffee: A Novel Method for Fast and Accurate Multiple Sequence Alignment," J. Mol. Biol., 302:205-217.
Alterman et al. (2015) "Hydrophobically Modified siRNAs Silence Huntingtin mRNA in Primary Neurons and Mouse Brain," Mol. Ther. Nucl. Acids, 4:e266.
Byrne et al. (2013) "Novel hydrophobically modified asymmetric RNAi compounds (sd-rxRNA) demonstrate robust efficacy in the eye," J. Ocul. Pharmacol. Ther., 29:855-864.
Hu et al. (2010) "Allele-selective inhibition of huntingtin expression by switching to an miRNA-like RNAi mechanism," Chem. Biol., 17:1183-1188.
International Search Report for International Application No. PCT/US18/36203, dated Oct. 10, 2018.
Pendergraff et al. (2016) "Single-Stranded Silencing RNAs: Hit Rate and Chemical Modification," Nucleic Acid Therapeutics, 7 pages.
Letsinger et al. (1989) "Cholesteryl-conjugated oligonucleotides: Synthesis, properties, and activity as inhibitors of replication of human immunodeficiency virus in cell culture," Natl. Acad. Sci. USA, 86:6553-6553.
Manoharan et al. (1994) "Cholic Acid-Oligonucleotide Conjugates for Antisense Applications," Bioorg. Med. Chem. Let., 4:1053-1060.
Manoharan et al. (1992) "Chemical Modifications to Improve Uptake and Bioavailability of Antisense Oligonucleotides," Ann. N.Y. Acad. Sci., 660:306-309.
Manoharan et al. (1993) "Introduction of a Lipophilic Thioether Thether in the Minor Groove of Nucleic Acids for Antisense Applications," Bioorg. Med. Chem. Let., 3:2765-2770.

(56) References Cited

OTHER PUBLICATIONS

Oberhauser et al. (1992) "Effective incorporation of 2'-O-methyl-oligoribonucleotides into liposomes and enhanced cell association through modification with thiocholesterol," Nucl. Acids Res., 20:533-538.

Kabanov et al. (1990) "A new class of antivirals: antisense oligonucleotides combined with a hydrophobic substituent effectively inhibit influenza virus reproduction and synthesis of virus-specific proteins in MDCK cells," FEBS Lett., 259:327-330.

Svinarchuk et al. (1993) "Inhibition of HIV profileration in MT-4 cells by antisense oligonucleotide conjugated to lipophilic groups," Biochimie, 75:49-54.

Manoharan et al. (1995) "Lipidic Nucleic Acids," Tetrahedron Lett., 36:3651-3654.

Shea et al. (1990) "Synthesis, hybridization properties and antiviral activity of lipid-oligodeoxynucleotide conjugates," Nucl. Acids Res., 18:3777-3783.

Mancharan et al. (1995) "Oligonucleotide Conjugates: Alteration of the Pharmacokinetic Properties of Antisense Agents," Nucleosides & Nucleosides, 14:969-973.

Mishra et al. (1995) "Improved leishmanicidal effect of phosphorotioate antisense oligonucleotides by LDL-mediated delivery," Biochim. Biophys. Acta, 1264:229-237.

Watts, J.K. (2015) "Molecularly Imprinted Polymers Incorporating Oligonucleotides," Oral Presentation at University of Southampton, Oxford Oligomer 2015.

Pendergraff, "Impact of oligonucleotide chemistry and silencing mechanism on applications in gene silencing and genome editing", Thesis, 2016, pp. 1-219.

Extended European Search Report for European Patent Application No. 18813723.6, dated Dec. 15, 2020.

Pendergraff et al., Poster Abstract for "Novel 1-12 Oligonucleotides for Asthma Research and Therapy", Oligo 2015 Oxford, Mar. 30, 2015, pp. 17-18.

* cited by examiner

Fig. 2A

| siRNA | Sequence<br>Uppercase: RNA; Lowercase: DNA | Calculated mass (g/mol) | Found mass (g/mol) |
|---|---|---|---|
| HMH-1 | 5'     GGAAGUACCUGGAACUGUA<br>    tt CCUUCAUGGACCUUGACAU 5' | S: 6124.7<br>AS: 6567.0 | S: 6123.8<br>AS: 6565.8 |
| HMH-2 | 5'     GGUGAGAGGUAGCUCCUAA<br>    tt CCACUCUCCAUCGAGGAUU 5' | S: 6140.7<br>AS: 6566.0 | S: 6139.8<br>AS: 6564.9 |
| HP-1 | 5'     AGAAAGACAUGUUGGCUAU<br>    tt UCUUUCUGUACAACCGAUA 5' | S: 6109.7<br>AS: 6552.0 | S: 6108.7<br>AS: 6550.8 |
| HP-2 | 5'     GGGAGAUGCUCAUGGAAAC<br>    tt CCCUCUACGAGUACCUUUG 5' | S: 6163.8<br>AS: 6543.0 | S: 6162.7<br>AS: 6542.7 |
| HP-3 | 5'     UGCUUGAGCUGGAGAAGAA<br>    tt ACGAACUCGACCUCUUCUU 5' | S: 6164.8<br>AS: 6527.0 | S: 6163.7<br>AS: 6525.7 |
| HP-4 | 5'     UGGUGAACUCUGCGGGAGA<br>    tt ACCACUUGAGACGCCCUCU 5' | S: 6156.7<br>AS: 6565.0 | S: 6155.7<br>AS: 6564.8 |
| HP-5 | 5'     CCCAACCACACGGAUCAUU tt<br>    tt GGGUUGGUGUGCCUAGUAA     5' | S: 6572.1<br>AS: 6743.1 | S: 6570.9<br>AS: 6742.9 |
| HP-6 | 5'     UGGCCCUGUGCAGGCUGAA tt<br>    tt ACCGGGACACGUCCGACUU     5' | S: 6701.1<br>AS: 6644.1 | S: 6701.0<br>AS: 6643.0 |
| HP-7 | 5'     AGUCCAGAUGCCAAGAUCC tt<br>    tt UCAGGUCUACGGUUCUAGG     5' | S: 6652.1<br>AS: 6663.0 | S: 6652.0<br>AS: 6662.9 |
| HP-8 | 5'     CCAGACGUUUACCUACUGG tt<br>    tt GGUCUGCAAAUGGAUGACC     5' | S: 6606.0<br>AS: 6709.1 | S: 6605.9<br>AS: 6708.0 |
| HP-9 | 5'     AGGGCGCCACAGUGGGCCU tt<br>    tt UCCCGCGGUGUCACCCGGA     5' | S: 6739.1<br>AS: 6636.1 | S: 6739.0<br>AS: 6636.0 |
| HP-10 | 5'     GAUCAAGUCCAGAUGCCAA tt<br>    tt CUAGUUCAGGUCUACGGUU     5' | S: 6676.1<br>AS: 6624.0 | S: 6675.0<br>AS: 6623.8 |
| HP-11 | 5'     UAGCAACCAUAACUGCCAC tt<br>    tt AUCGUUGGUAUUGACGGUG     5' | S: 6596.1<br>AS: 6704.0 | S: 6594.9<br>AS: 6703.9 |
| Scr | 5'     AGUGGAGGCGCCUGCCAC tt<br>    tt UCACCUCCGCGGACGGUG     5' | S: 6739.1<br>AS: 6636.1 | S: 6739.05<br>AS: 6634.99 |

| ss-siRNA | Sequence (5'-3')<br>s: phosphorothioate; LNA; 2'-F-RNA; 2'-O-methyl-RNA; MOE; P: 5' phosphate | Calculated mass (g/mol) | Found mass (g/mol) |
|---|---|---|---|
| ssi-HMH-1a | P-U$_s$ACAGUUCCAGG$_s$U$_s$A$_s$C$_s$U$_s$U$_s$C$_s$C$_s$A$_s$A | 7131.0 | 7131.6 |
| ssi-HP-2 | P-G$_s$UUUCCAUGAGC$_s$A$_s$U$_s$C$_s$U$_s$C$_s$C$_s$C$_s$A$_s$A | 7107.0 | 7106.6 |
| ssi-HP-3 | P-U$_s$UCUUCUCCAGC$_s$U$_s$C$_s$A$_s$A$_s$G$_s$C$_s$A$_s$A$_s$A | 7091.0 | 7090.6 |
| ssi-HMH-1b | P-U$_s$A$_s$CA$_s$GU$_s$UC$_s$CA$_s$GG$_s$UA$_s$C$_s$U$_s$U$_s$C$_s$C$_s$A$_s$A | 7196.0 | 7195.7 |
| ssi-HMH-1c | P-U$_s$A$_s$CA$_s$GU$_s$UC$_s$CA$_s$GG$_s$UA$_s$C$_s$U$_s$U$_s$C$_s$C$_s$A$_s$A | 7108.1 | 7107.7 |
| ssi-HMH-1d | P-U$_s$A$_s$CA$_s$GU$_s$UC$_s$CA$_s$GG$_s$UA$_s$C$_s$U$_s$U$_s$C$_s$C$_s$A$_s$A | 7104.1 | 7103.6 |

Fig. 3A

| LNA gapmer | Sequence (5'-3')<br>-s: phosphorothioate; LNA; Lowercase: DNA;<br>HOP: Hexadecyloxypropyl | Calculated mass (g/mol) | Found mass (g/mol) |
|---|---|---|---|
| 33-G | $T_sG_sA_s$ $t_sc_sc_sg_st_sg_st_sg_sg_s$ $T_sT_sG$ | 5023.0 | 5023.1 |
| 33-H | $A_sT_sG_s$ $a_st_sc_sc_sg_st_sg_st_sg_s$ $G_sT_sT$ | 5007.0 | 5007.1 |
| 33-I | $A_sA_sT_s$ $g_sa_st_sc_sc_sg_st_sg_st_s$ $G_sG_sT$ | 5016.0 | 5016.1 |
| 33-J | $C_sA_sA_s$ $t_sg_sa_st_sc_sc_sg_st_sg_s$ $T_sG_sG$ | 5015.0 | 5015.0 |
| 33-L | $T_sG_sT_s$ $c_sa_st_sg_sg_st_s$ $t_st_st_s$ $C_sA_sG$ | 4996.0 | 4996.0 |
| 33-M | $G_sG_sT_s$ $g_st_sc_sa_st_sg_sg_st_st_s$ $T_sT_sC$ | 5012.0 | 5012.1 |
| 33-N | $A_sG_sG_s$ $t_sg_st_sc_sa_st_sg_sg_st_s$ $T_sT_sT$ | 5022.0 | 5022.0 |
| 33-O | $T_sC_sA_s$ $t_st_st_sa_sg_sg_sa_sg_s$ $C_sT_sA$ | 5003.0 | 5003.1 |
| 33-P | $T_sT_sC_s$ $a_st_st_st_st_sa_sg_sg_sa_s$ $G_sC_sT$ | 4994.0 | 4994.1 |
| 33-Q | $T_sG_sT_s$ $t_sc_sa_st_st_st_sa_sg_s$ $G_sA_sG$ | 5006.0 | 5006.0 |
| 33-R | $T_sC_sC_s$ $g_st_sg_sg_sa_sa_st_st_s$ $G_sC_sA$ | 5027.0 | 5027.1 |
| lna ctrl | $A_sT_sT_s$ $t_st_sa_st_sc_sg_sg_sa_s$ $G_sC_sT$ | 4980.0 | 4980.4 |
| lna scr2 | $A_sA_sC_s$ $a_s{}^mc_sg_st_s{}^mc_st_sa_st_sa_s$ $C_sG_sC$<br>($^mC$ is 5-methylcytosine) | 4984.1 | 4983.5 |

Fig. 5C

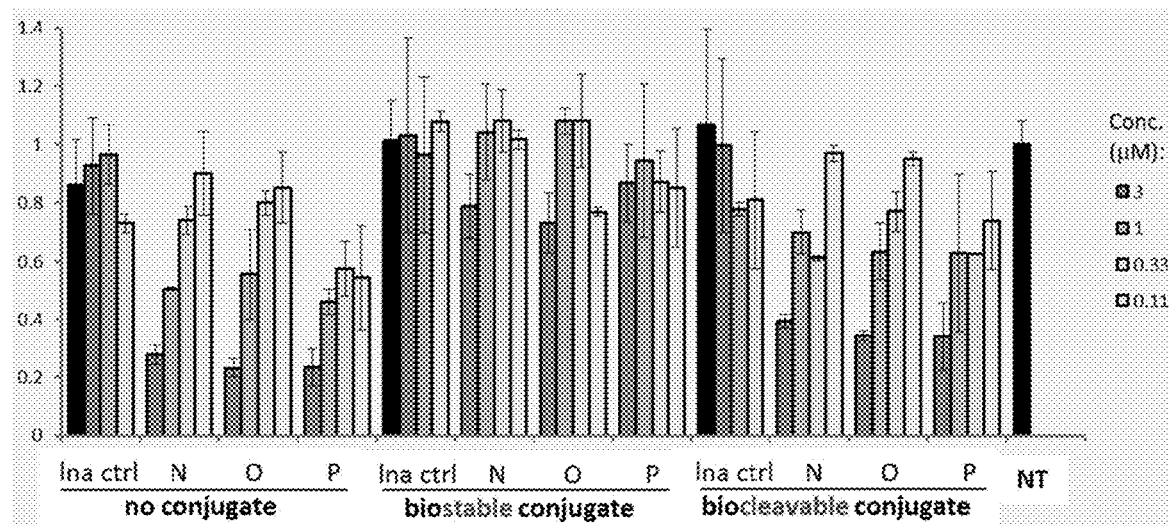

Fig. 5D

| Conjugated LNA gapmer | Sequence (5'-3')<br>$_s$: phosphorothioate; LNA; Lowercase: DNA; HOP: Hexadecyloxypropyl | Calculated mass (g/mol) | Found mass (g/mol) |
|---|---|---|---|
| 33-N biostable | HOP$_s$A$_s$G$_s$G$_s$ t$_s$g$_s$t$_s$c$_s$a$_s$g$_s$g$_s$t$_s$ T$_s$T$_s$T | 5400.2 | 5399.7 |
| 33-O biostable | HOP$_s$T$_s$C$_s$A$_s$ t$_s$t$_s$t$_s$t$_s$a$_s$g$_s$g$_s$a$_s$g$_s$C$_s$T$_s$A | 5364.2 | 5364.8 |
| 33-P biostable | HOP$_s$T$_s$T$_s$C$_s$ a$_s$t$_s$t$_s$t$_s$t$_s$a$_s$g$_s$g$_s$a$_s$G$_s$C$_s$T | 5355.2 | 5355.8 |
| 33-N biocleavable | HOP t t t t t t A$_s$G$_s$G$_s$ t$_s$g$_s$t$_s$c$_s$a$_s$g$_s$g$_s$t$_s$ T$_s$T$_s$T | 7209.4 | 7208.8 |
| 33-O biocleavable | HOP t t t t t t T$_s$C$_s$A$_s$ t$_s$t$_s$t$_s$t$_s$a$_s$g$_s$g$_s$a$_s$g$_s$C$_s$T$_s$A | 7190.5 | 7189.3 |
| 33-P biocleavable | HOP t t t t t t T$_s$T$_s$C$_s$ a$_s$t$_s$t$_s$t$_s$t$_s$a$_s$g$_s$g$_s$a$_s$G$_s$C$_s$T | 7181.5 | 7181.0 |

US 11,401,519 B2

SEQUENCE LISTING

<160> NUMBER OF SEQ ID NOS: 107

<210> SEQ ID NO 1
<211> LENGTH: 4153
<212> TYPE: DNA
<213> ORGANISM: Homo sapiens

<400> SEQUENCE: 1

```
atgcaattct gccctctggc caccgccagg gaagaaaggt tgtctccgtc tgctgcatcg      60
cctttgccca gcaatgaagc ccccaagaca gcggcagccg gttgcctgaa ccttcctatc     120
cttgggggca cccagtgcag gtggatgacc cgactcaacc tccgccaggg caccctcggg     180
gcaggacggg tagcaaggag gggacagaga tcggccccag gagaccacgg aagatcgcgc     240
tcctggggcc aacttcagca gcgagaggcg gcctttgccc accgcctcat cccaccacgc     300
cgcggtcctc caagaacctt cccagcggtt ctctcctcct ctcaggagta gaggccctct     360
gagaccgacg gggagggacg gctcgggccg gtcatccgag gggccgcacg gattccctcc     420
tccgcccagc tccaccccct cgaggggcgg cggtccggga gtggcgaccc ggctccccca     480
```

```
tggcgcgcgc cgtcggggcc cctggccagg ctccgagcgg ggttggcggg gaggggaggc      540
gggagcgagg gcgggcggtg ggaggtgggg gcgggaaggt ccgaaggcgg cggcctgagg      600
ctgcaccggg cacgggtcgg ccgcaatcca gcctgggcgg agccggagtt gcgagccgct      660
gcctagaggc cgaggagctc acagctatgg gctggaggcc ccggagagct cggggggaccc     720 cgttgctgct gctgctacta ctgctgctgc tctggccagt gccaggcgcc ggggtgcttc      780
aaggacatat ccctgggcag ccagtcaccc cgcactgggc cctggatgga caaccctggc      840
gcaccgtcag cctggaggag ccggtctcga agccagacat ggggctggtg gccctggagg      900
ctgaaggcca ggagctcctg cttgagctgg agaagaacca caggctgctg gccccaggat      960
acatagaaac ccactacggc ccagatgggc agccagtggt gctggccccc aaccacacgg     1020
atcattgcca ctaccaaggg cgagtaaggg gcttccccga ctcctgggta gtcctctgca     1080
cctgctctgg gatgagtggc ctgatcaccc tcagcaggaa tgccagctat tatctgcgtc     1140
cctggccacc ccggggctcc aaggacttct caacccacga gatctttcgg atggagcagc     1200
tgctcacctg gaaaggaacc tgtggccaca gggatcctgg gaacaaagcg ggcatgacca     1260
gccttcctgg tggtccccag agcagggggca ggcgagaagc gcgcaggacc cggaagtacc    1320
tggaactgta cattgtggca gaccacaccc tgttcttgac tcggcaccga aacttgaacc     1380
acaccaaaca gcgtctcctg gaagtcgcca actacgtgga ccagcttctc aggactctgg     1440
acattcaggt ggcgctgacc ggcctggagg tgtggaccga gcgggaccgc agccgcgtca     1500
cgcaggacgc caacgccacg ctctgggcct tcctgcagtg gcgccggggg ctgtgggcgc     1560
agcggcccca cgactccgcg cagctgctca cgggccgcgc cttccagggc gccacagtgg     1620
gcctggcgcc cgtcgagggc atgtgccgcg ccgagagctc gggaggcgtg agcacggacc     1680
actcggagct ccccatcggc gccgcagcca ccatggccca tgagatcggc cacagcctcg     1740
gcctcagcca cgaccccgac ggctgctgcg tggaggctgc ggccgagtcc ggaggctgcg     1800
tcatggctgc ggccaccggg cacccgtttc cgcgcgtgtt cagcgcctgc agccgccgcc     1860
agctgcgcgc cttcttccgc aaggggggcg gcgcttgcct ctccaatgcc ccggaccccg     1920
gactcccggt gccgccggcg ctctgcggga acggcttcgt ggaagcgggc gaggagtgtg     1980
actgcggccc tggccaggag tgccgcgacc tctgctgctt tgctcacaac tgctcgctgc     2040
gccccggggc ccagtcgcgcc cacggggact gctgcgtgcg ctgcctgctg aagcggctg     2100 gagcgctgtg ccgccaggcc atgggtgact gtgacctccc tgagttttgc acgggcacct     2160
cctcccactg tcccccagac gtttacctac tggacggctc accctgtgcc aggggcagtg     2220
gctactgctg ggatggcgca tgtcccacgc tggagcagca gtgccagcag ctctgggggc     2280
ctggctccca cccagctccc gaggcctgtt tccaggtggt gaactctgcg ggagatgctc     2340
atggaaactg cggccaggac agcgagggcc acttcctgcc ctgtgcaggg agggatgccc     2400
tgtgtgggaa gctgcagtgc cagggtggaa agcccagcct gctcgcaccg cacatggtgc     2460
cagtggactc taccgttcac ctagatggcc aggaagtgac ttgtcgggga gccttggcac     2520
tccccagtgc ccagctggac ctgcttggcc tgggcctggt agagccaggc acccagtgtg     2580
gacctagaat ggtgtgccag agcaggcgct gcaggaagaa tgccttccag gagcttcagc     2640
gctgcctgac tgcctgccac agccacgggg tttgcaatag caaccataac tgccactgtg     2700
ctccaggctg ggctccaccc ttctgtgaca agcaggcttt ggtggcagc atggacagtg      2760 gccctgtgca ggctgaaaac catgacacct tcctgctggc catgctcctc agcgtcctgc     2820
```

| | |
|---|---|
| tgcctctgct cccagggggcc ggcctggcct ggtgttgcta ccgactccca ggagcccatc | 2880 |
| tgcagcgatg cagctgggggc tgcagaaggg accctgcgtg cagtggcccc aaagatggcc | 2940 |
| cacacaggga ccaccccctg ggcggcgttc accccatgga gttgggcccc acagccactg | 3000 |
| gacagccctg gccctggac cctgagaact ctcatgagcc cagcagccac cctgagaagc | 3060 |
| ctctgccagc agtctcgcct gacccccaag atcaagtcca gatgccaaga tcctgcctct | 3120 |
| ggtgagaggt agctcctaaa atgaacagat ttaaagacag gtggccactg acagccactc | 3180 |
| caggaacttg aactgcaggg gcagagccag tgaatcaccg acctccagc acctgcaggc | 3240 |
| agcttggaag tttcttcccc gagtggagct tcgacccacc cactccagga acccagagcc | 3300 |
| acattagaag ttcctgaggg ctggagaaca ctgctgggca cactctccag ctcaataaac | 3360 |
| catcagtccc agaagcaaag gtcacacagc ccctgacctc cctcaccagt ggaggctggg | 3420 |
| tagtgctggc catcccaaaa gggctctgtc ctgggagtct ggtgtgtctc ctacatgcaa | 3480 |
| tttccacgga cccagctctg tggagggcat gactgctggc cagaagctag tggtcctggg | 3540 |
| gccctatggt tcgactgagt ccacactccc ctggagcctg gctggcctct gcaaacaaac | 3600 |
| ataattttgg ggaccttcct tcctgttttct tcccaccctg tcttctcccc taggtggttc | 3660 |
| ctgagccccc accccaatc ccagtgctac acctgaggtt ctggagctca gaatctgaca | 3720 |
| gcctctcccc cattctgtgt gtgtcggggg gacagaggga accatttaag aaaagatacc | 3780 |
| aaagtagaag tcaaaagaaa gacatgttgg ctataggcgt ggtggctcat gcctataatc | 3840 |
| ccagcacttt gggaagccgg ggtaggagga tcaccagagg ccagcaggtc cacaccagcc | 3900 |
| tgggcaacac agcaagacac cgcatctaca gaaaaatttt aaaattagct gggcgtggtg | 3960 |
| gtgtgtacct gtaggcctag ctgctcagga ggctgaagca ggaggatcac ttgagcctga | 4020 |
| gttcaacact gcagtgagct atggtggcac cactgcactc cagcctgggt gacagagcaa | 4080 |
| gaccctgtct ctaaaataaa ttttaaaaag acatattaca cttaaaaaaa aaaaaaaaaa | 4140 |
| aaaaaaaaaa aaa | 4153 |

<210> SEQ ID NO 2
<211> LENGTH: 4156
<212> TYPE: DNA
<213> ORGANISM: Homo sapiens

<400> SEQUENCE: 2

| | |
|---|---|
| atgcaattct gccctctggc caccgccagg gaagaaaggt tgtctccgtc tgctgcatcg | 60 |
| cctttgccca gcaatgaagc ccccaagaca gcggcagccg gttgcctgaa ccttcctatc | 120 |
| cttggggggca cccagtgcag gtggatgacc cgactcaacc tccgccaggg caccctcggg | 180 |
| gcaggacggg tagcaaggag gggacagaga tcggccccag gagaccacgg aagatcgcgc | 240 |
| tcctggggcc aacttcagca gcgagaggcg gcctttgccc accgcctcat cccaccacgc | 300 |
| cgcggtcctc caagaacctt cccagcggtt ctctcctcct ctcaggagta gaggccctct | 360 |
| gagaccgacg ggggagggacg gctcgggccg gtcatccgag gggccgcacg gattccctcc | 420 |
| tccgcccagc tccaccccct cgaggggcgg cggtccggga gtggcgaccc ggctcccccca | 480 |
| tggcgcgcgc cgtcgggggcc cctggccagg ctccgagcgg ggttggcggg gaggggaggc | 540 |
| gggagcgagg gcgggcggtg ggaggtgggg gcgggaaggt ccgaaggcgg cggcctgagg | 600 |
| ctgcaccggg cacgggtcgg ccgcaatcca gcctgggcgg agccggagtt gcgagccgct | 660 |
| gcctagaggc cgaggagctc acagctatgg gctgaggcc ccgagagct cggggggaccc | 720 |
| cgttgctgct gctgctacta ctgctgctgc tctggccagt gccaggcgcc ggggtgcttc | 780 |

-continued

```
aaggacatat ccctgggcag ccagtcaccc cgcactgggt cctggatgga caaccctggc      840
gcaccgtcag cctggaggag ccggtctcga agccagacat ggggctggtg ccctggagg       900
ctgaaggcca ggagctcctg cttgagctgg agaagaacca caggctgctg gccccaggat      960
acatagaaac ccactacggc ccagatgggc agccagtggt gctggccccc aaccacacgg     1020
atcattgcca ctaccaaggg cgagtaaggg gcttccccga ctcctgggta gtcctctgca     1080
cctgctctgg gatgagtggc ctgatcaccc tcagcaggaa tgccagctat tatctgcgtc     1140
cctggccacc ccggggctcc aaggacttct caacccacga gatctttcgg atggagcagc     1200
tgctcacctg gaaaggaacc tgtggccaca gggatcctgg gaacaaagcg ggcatgacca     1260
gccttcctgg tggtccccag agcaggggca ggcgagaagc gcgcaggacc cggaagtacc     1320
tggaactgta cattgtggca gaccacaccc tgttcttgac tcggaccga aacttgaacc      1380
acaccaaaca gcgtctcctg gaagtcgcca actacgtgga ccagcttctc aggactctgg     1440
acattcaggt ggcgctgacc ggcctggagg tgtggaccga gcgggaccgc agccgcgtca     1500
cgcaggacgc caacgccacg ctctgggcct tcctgcagtg gcgccggggg ctgtgggcgc     1560
agcgccccca cgactccgcg cagctgctca cgggccgcgc cttccagggc gccacagtgg     1620
gcctggcgcc cgtcgagggc atgtgccgcg ccgagagctc gggaggcgtg agcacggacc     1680
actcggagct ccccatcggc gccgcagcca ccatggccca tgagatcggc cacagcctcg     1740
gcctcagcca cgaccccgac ggctgctgcg tggaggctgc ggccgagtcc ggaggctgcg     1800
tcatggctgc ggccaccggg cacccgtttc cgcgcgtgtt cagcgcctgc agccgccgcc     1860
agctgcgcgc cttcttccgc aagggggggcg gcgcttgcct ctccaatgcc ccggaccccg     1920
gactcccggt gccgccggcg ctctgcggga acggcttcgt ggaagcgggc gaggagtgtg     1980
actgcggccc tggccaggag tgccgcgacc tctgctgctt tgctcacaac tgctcgctgc     2040
gcccgggggc ccagtgcgcc cacggggact gctgcgtgcg ctgcctgctg aagccggctg     2100
gagcgctgtg ccgccaggcc atgggtgact gtgacctccc tgagttttgc acgggcacct     2160
cctcccactg tccccagac gtttacctac tggacggctc accctgtgcc aggggcagtg      2220
gctactgctg ggatggcgca tgtcccacgc tggagcagca gtgccagcag ctctgggggc     2280
ctggctccca cccagctccc gaggcctgtt ccaggtggt gaactctgcg ggagatgctc      2340
atggaaactg cggccaggac agcgaggggcc acttcctgcc ctgtgcaggg agggatgccc    2400
tgtgtgggaa gctgcagtgc cagggtggaa agcccagcct gctcgcaccg cacatggtgc     2460
cagtggactc taccgttcac ctagatggcc aggaagtgac ttgtcgggga gccttggcac     2520
tccccagtgc ccagctggac ctgcttggcc tgggcctggt agagccaggc acccagtgtg     2580
gacctagaat ggtgtgccag agcaggcgct gcaggaagaa tgccttccag gagcttcagc     2640
gctgcctgac tgcctgccac agccacgggg tttgcaatag caaccataac tgccactgtg     2700
ctccaggctg ggctccaccc ttctgtgaca agccaggctt tggtggcagc atggacagtg     2760
gccctgtgca ggctgaaaac catgacacct tcctgctggc catgctcctc agcgtcctgc     2820
tgcctctgct cccaggggcc ggcctggcct ggtgttgcta ccgactccca ggagcccatc     2880
tgcagcgatg cagctggggc tgcagaaggg accctgcgtg cagtggcccc aaagatggcc     2940
cacacaggga ccaccccctg ggcggcgttc accccatgga gttgggcccc acagccactg     3000
gacagccctg gcccctggac cctgagaact ctcatgagcc cagcagccac cctgagaagc     3060
ctctgccagc agtctcgcct gaccccccaag cagatcaagt ccagatgcca agatcctgcc    3120
```

| | |
|---|---|
| tctggtgaga ggtagctcct aaaatgaaca gatttaaaga caggtggcca ctgacagcca | 3180 |
| ctccaggaac ttgaactgca ggggcagagc cagtgaatca ccggacctcc agcacctgca | 3240 |
| ggcagcttgg aagtttcttc cccgagtgga gcttcgaccc acccactcca ggaacccaga | 3300 |
| gccacattag aagttcctga gggctggaga acactgctgg gcacactctc cagctcaata | 3360 |
| aaccatcagt cccagaagca aaggtcacac agccctgac ctccctcacc agtggaggct | 3420 |
| gggtagtgct ggccatccca aaagggctct gtcctgggag tctggtgtgt ctcctacatg | 3480 |
| caatttccac ggacccagct ctgtggaggg catgactgct ggccagaagc tagtggtcct | 3540 |
| ggggccctat ggttcgactg agtccacact ccctggagc ctggctggcc tctgcaaaca | 3600 |
| aacataattt tggggacctt ccttcctgtt tcttcccacc ctgtcttctc ccctaggtgg | 3660 |
| ttcctgagcc cccacccca atcccagtgc tacacctgag gttctggagc tcagaatctg | 3720 |
| acagcctctc ccccattctg tgtgtgtcgg ggggacagag ggaaccattt aagaaaagat | 3780 |
| accaaagtag aagtcaaaag aaagacatgt tggctatagg cgtggtggct catgcctata | 3840 |
| atcccagcac tttgggaagc cggggtagga ggatcaccag aggccagcag gtccacacca | 3900 |
| gcctgggcaa cacagcaaga caccgcatct acagaaaaat tttaaaatta gctgggcgtg | 3960 |
| gtggtgtgta cctgtaggcc tagctgctca ggaggctgaa gcaggaggat cacttgagcc | 4020 |
| tgagttcaac actgcagtga gctatggtgg caccactgca ctccagcctg ggtgacagag | 4080 |
| caagaccctg tctctaaaat aaattttaaa aagacatatt cacttaaaa aaaaaaaaa | 4140 |
| aaaaaaaaaa aaaaaa | 4156 |

<210> SEQ ID NO 3
<211> LENGTH: 4078
<212> TYPE: DNA
<213> ORGANISM: Homo sapiens

<400> SEQUENCE: 3

| | |
|---|---|
| atgcaattct gccctctggc caccgccagg gaagaaaggt tgtctccgtc tgctgcatcg | 60 |
| cctttgccca gcaatgaagc ccccaagaca gcggcagccg gttgcctgaa ccttcctatc | 120 |
| cttgggggca cccagtgcag gtggatgacc cgactcaacc tccgccaggg caccctcggg | 180 |
| gcaggacggg tagcaaggag gggacagaga tcggccccag gagaccacgg aagatcgcgc | 240 |
| tcctggggcc aacttcagca gcgagaggcg gcctttgccc accgcctcat cccaccacgc | 300 |
| cgcggtcctc caagaacctt cccagcggtt ctctcctcct ctcaggagta gaggccctct | 360 |
| gagaccgacg gggagggacg gctcgggccg gtcatccgag gggccgcacg gattccctcc | 420 |
| tccgcccagc tccacccct cgaggggcgg cggtccggga gtggcgaccc ggctccccca | 480 |
| tggcgcgcgc cgtcgggccc cctggccagg ctccgagcgg ggttggcggg aggggaggc | 540 |
| gggagcgagg gcgggcggtg ggaggtgggg gcgggaaggt ccgaaggcgg cggcctgagg | 600 |
| ctgcaccggg cacgggtcgg ccgcaatcca gcctgggcgg agccggagtt gcgagccgct | 660 |
| gcctagaggc cgaggagctc acagctatgg gctgaggcc ccgagagct cggggaccc | 720 |
| cgttgctgct gctgctacta ctgctgctgc tctggccagt gccaggcgcc ggggtgcttc | 780 |
| aaggacatat ccctgggcag ccagtcaccc cgcactgggt cctggatgga caaccctggc | 840 |
| gcaccgtcag cctggaggag ccggtctcga agccagacat ggggctggtg gccctggagg | 900 |
| ctgaaggcca ggagtccctg cttgagctgg agaagaacca caggctgctg gccccaggat | 960 |
| acatagaaac ccactacggc ccagatgggc agccagtggt gctggcccc aaccacacgg | 1020 |
| atcattgcca ctaccaaggg cgagtaaggg gcttccccga ctcctgggta gtcctctgca | 1080 |

```
cctgctctgg gatgagtggc ctgatcaccc tcagcaggaa tgccagctat tatctgcgtc    1140
cctggccacc ccggggctcc aaggacttct caacccacga gatctttcgg atggagcagc    1200
tgctcacctg gaaaggaacc tgtggccaca gggatcctgg aacaaagcg ggcatgacca     1260 gccttcctgg tggtccccag agcaggggca ggcgagaagc gcgcaggacc cggaagtacc    1320
tggaactgta cattgtggca gaccacaccc tgttcttgac tcggcaccga aacttgaacc    1380
acaccaaaca gcgtctcctg gaagtcgcca actacgtgga ccagcttctc aggactctgg    1440
acattcaggt ggcgctgacc ggcctggagg tgtggaccga gcgggaccgc agccgcgtca    1500
cgcaggacgc caacgccacg ctctgggcct tcctgcagtg gcgccggggg ctgtgggcgc    1560
agcggcccca cgactccgcg cagctgctca cgggccgcgc cttccagggc gccacagtgg    1620
gcctggcgcc cgtcgagggc atgtgccgcg ccgagagctc ggaggcgtg agcacggacc     1680 actcggagct ccccatcggc gccgcagcca ccatggccca tgagatcggc cacagcctcg    1740
gcctcagcca cgaccccgac ggctgctgcg tggaggctgc ggccgagtcc ggaggctgcg    1800
tcatggctgc ggccaccggg cacccgtttc gcgcgtgtt cagcgcctgc agccgccgcc    1860
agctgcgcgc cttcttccgc aagggggggcg gcgcttgcct ctccaatgcc ccggaccccg    1920
gactcccggt gccgccggcg ctctgcggga acggcttcgt ggaagcgggc gaggagtgtg    1980
actgcggccc tggccaggag tgccgcgacc tctgctgctt tgctcacaac tgctcgctgc    2040 gcccggggc ccagtgcgcc cacggggact gctgcgtgcg ctgcctgctg aagccggctg     2100
gagcgctgtg ccgccaggcc atgggtgact gtgacctccc tgagttttgc acgggcacct    2160
cctcccactg tccccccagac gtttacctac tggacggctc accctgtgcc aggggcagtg    2220
gctactgctg ggatggcgca tgtcccacgc tggagcagca gtgccagcag ctctgggggc    2280
ctggctccca cccagctccc gaggcctgtt ccaggtggt gaactctgcg ggagatgctc      2340
atggaaactg cggccaggac agcgagggcc acttcctgcc ctgtgcaggg agggatgccc    2400
tgtgtgggaa gctgcagtgc cagggtggaa agcccagcct gctcgcaccg cacatggtgc    2460
cagtggactc taccgttcac ctagatggcc aggaagtgac ttgtcgggga gccttggcac    2520
tccccagtgc ccagctggac ctgcttggcc tgggcctggt agagccaggc acccagtgtg    2580
gacctagaat ggtttgcaat agcaaccata actgccactg tgctccaggc tgggctccac    2640
ccttctgtga caagccaggc tttggtgca gcatggacag tggccctgtg caggctgaaa     2700
accatgacac cttcctgctg gccatgctcc tcagcgtcct gctgcctctg ctcccagggg    2760
ccggcctggc ctgtgttgc taccgactcc caggagccca tctgcagcga tgcagctggg     2820
gctgcagaag ggaccctgcg tgcagtggcc ccaaagatgg cccacacagg gaccacccc     2880 tgggcggcgt tcacccccatg gagttgggcc ccacagccac tggacagccc tggccctgg    2940 accctgagaa ctctcatgag cccagcagcc accctgagaa gcctctgcca gcagtctcgc    3000
ctgaccccca agcagatcaa gtccagatgc caagatcctg cctctggtga gaggtagctc    3060
ctaaaatgaa cagatttaaa gacaggtggc cactgacagc cactccagga acttgaactg    3120
caggggcaga gccagtgaat caccggacct ccagcacctg caggcagctt ggaagtttct    3180
tccccgagtg gagcttcgac ccacccactc caggaaccca gagccacatt agaagttcct    3240
gagggctgga gaacactgct gggcacactc tccagctcaa taaaccatca gtcccagaag    3300
caaaggtcac acagccctg acctccctca ccagtggagg ctgggtagtg ctggccatcc     3360
caaaagggct ctgtcctggg agtctggtgt gtctcctaca tgcaatttcc acggacccag    3420
```

```
ctctgtggag ggcatgactg ctggccagaa gctagtggtc ctggggccct atggttcgac    3480
tgagtccaca ctcccctgga gcctggctgg cctctgcaaa caaacataat tttggggacc    3540
ttccttcctg tttcttccca ccctgtcttc tcccctaggt ggttcctgag cccccacccc    3600
caatcccagt gctacacctg aggttctgga gctcagaatc tgacagcctc tcccccattc    3660
tgtgtgtgtc gggggacag agggaaccat ttaagaaaag ataccaaagt agaagtcaaa    3720
agaaagacat gttggctata ggcgtggtgg ctcatgccta taatcccagc actttgggaa    3780
gccggggtag gaggatcacc agaggccagc aggtccacac cagcctgggc aacacagcaa    3840
gacaccgcat ctacagaaaa attttaaaat tagctgggcg tggtggtgtg tacctgtagg    3900
cctagctgct caggaggctg aagcaggagg atcacttgag cctgagttca acactgcagt    3960
gagctatggt ggcaccactg cactccagcc tgggtgacag agcaagaccc tgtctctaaa    4020 ataaattta aaagacata ttacacttaa aaaaaaaaa aaaaaaaaa aaaaaaa    4078

<210> SEQ ID NO 4
<211> LENGTH: 3573
<212> TYPE: DNA
<213> ORGANISM: Homo sapiens

<400> SEQUENCE: 4
gggaggtggg ggcgggaagg tccgaaggcg gcggcctgag gctgcaccgg gcacgggtcg      60
gccgcaatcc agcctgggcg gagccggagt tgcgagccgc tgcctagagg ccgaggagct     120
cacagctatg ggctggaggc cccggagagc tcggggggacc ccgttgctgc tgctgctact     180
actgctgctg ctctggccag tgccaggcgc cggggtgctt caaggacata tccctgggca     240
gccagtcacc ccgcactggg tcctggatgg acaaccctgg cgcaccgtca gcctggagga     300
gccggtctcg aagccagaca tggggctggt ggccctggag gctgaaggcc aggagctcct     360
gcttgagctg gagaagaacc acaggctgct ggccccagga tacatagaaa cccactacgg     420
cccagatggg cagccagtgg tgctggcccc caaccacacg gatcattgcc actaccaagg     480
gcgagtaagg ggcttcccccg actcctgggt agtcctctgc acctgctctg ggatgagtgg     540
cctgatcacc ctcagcagga atgccagcta ttatctgcgt ccctggccac cccggggctc     600
caaggacttc tcaacccacg agatctttcg gatggagcag ctgctcacct ggaaaggaac     660
ctgtggccac agggatcctg gaacaaagc gggcatgacc agccttcctg gtggtccccca     720 gagcaggggc aggcgagaag cgcgcaggac ccggaagtac ctggaactgt acattgtggc     780
agaccacacc ctgttcttga ctcggcaccg aaacttgaac cacaccaaac agcgtctcct     840
ggaagtcgcc aactacgtgg accagcttct caggactctg gacattcagg tggcgctgac     900
cggcctggag gtgtggaccg agcgggaccg cagccgcgtc acgcaggacg ccaacgccac     960
gctctgggcc ttcctgcagt ggcgccgggg gctgtgggcg cagcggcccc acgactccgc    1020
gcagctgctc acgggccgcg ccttccaggg cgccacagtg ggcctggcgc cgtcgagggg    1080
catgtgccgc gccgagagct cgggaggcgt gagcacggac cactcggagc tcccatcgg    1140 cgccgcagcc accatggccc atgagatcgg ccacagcctc ggcctcagcc acgaccccga    1200
cggctgctgc gtgaggctg cggccgagtc cggaggctgc gtcatggctg cggccaccgg    1260
gcaccgtttt ccgcgcgtgt tcagcgcctg cagccgccgc cagctgcgcg ccttcttccg    1320 caagggggc ggcgcttgcc tctccaatgc cccggacccc ggactccggg tgccgccggc    1380
gctctgcggg aacggcttcg tggaagcggg cgaggagtgt gactgcggcc ctggccagga    1440
gtgccgcgac ctctgctgct tgctcacaa ctgctcgctg cgcccggggg cccagtgcgc    1500
```

```
ccacggggac tgctgcgtgc gctgcctgct gaagccggct ggagcgctgt gccgccaggc    1560
catgggtgac tgtgacctcc ctgagttttg cacgggcacc tcctcccact gtcccccaga    1620
cgtttaccta ctggacggct caccctgtgc caggggcagt ggctactgct gggatggcgc    1680 atgtccacg  ctggagcagc agtgccagca gctctggggg cctggctccc acccagctcc    1740
cgaggcctgt ttccaggtgg tgaactctgc gggagatgct catggaaact gcggccagga    1800
cagcgagggc cacttcctgc cctgtgcagg gagggatgcc ctgtgtggga agctgcagtg    1860
ccagggtgga aagcccagcc tgctcgcacc gcacatggtg ccagtggact ctaccgttca    1920
cctagatggc caggaagtga cttgtcgggg agccttggca ctccccagtg cccagctgga    1980
cctgcttggc ctgggcctgg tagagccagg cacccagtgt ggacctagaa tggtgtgcca    2040
gagcaggcgc tgcaggaaga atgccttcca ggagcttcag cgctgcctga ctgcctgcca    2100
cagccacggg gtttgcaata gcaaccataa ctgccactgt gctccaggct gggctccacc    2160
cttctgtgac aagccaggct ttggtggcag catggacagt ggccctgtgc aggctgaaaa    2220
ccatgacacc ttcctgctgg ccatgctcct cagcgtcctg ctgcctctgc tcccaggggc    2280
cggcctggcc tggtgttgct accgactccc aggagcccat ctgcagcgat gcagctgggg    2340
ctgcagaagg gaccctgcgt gcagtggccc caaagatggc ccacacaggg accaccccct    2400
gggcggcgtt caccccatgg agttgggccc acagccact  ggacagccct ggcccctgga    2460
ccctgagaac tctcatgagc ccagcagcca ccctgagaag cctctgccag cagtctcgcc    2520 tgaccccaa  gcagatcaag tccagatgcc aagatcctgc ctctggtgag aggtagctcc    2580
taaaatgaac agatttaaag acaggtggcc actgacagcc actccaggaa cttgaactgc    2640
aggggcagag ccagtgaatc accggacctc cagcacctgc aggcagcttg aagtttctt    2700 ccccgagtgg agcttcgacc cacccactcc aggaacccag agccacatta gaagttcctg    2760
agggctggag aacactgctg ggcacactct ccagctcaat aaaccatcag tcccagaagc    2820
aaaggtcaca cagcccctga cctccctcac cagtggaggc tgggtagtgc tggccatccc    2880
aaaagggctc tgtcctggga gtctggtgtg tctcctacat gcaatttcca cggacccagc    2940
tctgtggagg gcatgactgc tggccagaag ctagtggtcc tggggcccta tggttcgact    3000
gagtccacac tccctggag  cctggctggc ctctgcaaac aaacataatt tggggacct    3060 tccttcctgt ttcttccac  cctgtcttct cccctaggtg gttcctgagc ccccaccccc    3120
aatcccagtg ctacacctga ggttctggag ctcagaatct gacagcctct ccccattct    3180 gtgtgtgtcg ggggacaga  gggaaccatt taagaaaaga taccaaagta gaagtcaaaa    3240
gaaagacatg ttggctatag gcgtggtggc tcatgcctat aatcccagca ctttgggaag    3300
ccggggtagg aggatcacca gaggccagca ggtccacacc agcctgggca acacagcaag    3360
acaccgcatc tacagaaaaa ttttaaaatt agctgggcgt ggtggtgtgt acctgtaggc    3420
ctagctgctc aggaggctga agcaggagga tcacttgagc ctgagttcaa cactgcagtg    3480
agctatggtg gcaccactgc actccagcct gggtgacaga gcaagaccct gtctctaaaa    3540
taaattttaa aagacataa  aaaaaaaaaa aaa                                3573
```

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
     oligonucleotide

```
<400> SEQUENCE: 5
tgatccgtgt ggttg                                                    15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgatccgtg tggtt                                                    15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aatgatccgt gtggt                                                    15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caatgatccg tgtgg                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgtcatggtt ttcag                                                    15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggtgtcatgg ttttc                                                    15

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 11
aggtgtcatg gtttt                                                    15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcattttagg agcta                                                    15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttcattttag gagct                                                    15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgttcatttt aggag                                                    15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tccgtggaaa ttgca                                                    15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgatccgtgt ggttg                                                    15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
```
atgatccgtg tggtt                                                15

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatgatccgt gtggt                                                15

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caatgatccg tgtgg                                                15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgtcatggtt ttcag                                                15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggtgtcatgg ttttc                                                15

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aggtgtcatg gtttt                                                15

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcattttagg agcta                                                    15

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttcattttag gagct                                                    15

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tgttcatttt aggag                                                    15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tccgtggaaa ttgca                                                    15

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttttttgat ccgtgtggtt g                                             21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 tttttttatga tccgtgtggt t                                            21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 tttttttaatg atccgtgtgg t                                            21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tttttcaat gatccgtgtg g                                          21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttttttgtc atggttttca g                                         21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 tttttggtg tcatggtttt c                                          21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 tttttaggt gtcatggttt t                                          21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 ttttttcat tttaggagct a                                          21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 tttttttca ttttaggagc t                                          21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttttttgtt cattttagga g                                            21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tttttttccg tggaaattgc a                                            21

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggcctctgca aacaaacata att                                          23

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggctcagga accacctagg                                              20

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cttcctgttt cttcccaccc tgtcttctct                                   30

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggtccaggg gtcttact                                                18

```
<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cctcaacgac cactttgt                                                   18

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ctcatttcct ggtatgacaa cgaatttggc                                      30

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgatccgtgt ggttg                                                      15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgatccgtgt ggttg                                                      15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aggtgtcatg gtttt                                                      15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aggcatctcg gtttg                                                      15

<210> SEQ ID NO 48
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcattttagg agct                                                       14

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
taagctcaga gttcg                                                      15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgttcatttt aggag                                                      15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtaagctca gagtt                                                      15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tccgtggaaa ttgca                                                      15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tctatgacaa cagct                                                      15

<210> SEQ ID NO 54
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aacacgtcta tacgc                                                      15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aggcatctcg gtttg                                                      15

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
taagctcaga gttcg                                                      15

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggtaagctca gagtt                                                      15

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tctatgacaa cagct                                                      15

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ggaaguaccu ggaacugua                                                  19

<210> SEQ ID NO 60
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
uacaguucca gguacuucct t                                              21

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ggugagaggu agcuccuaa                                                 19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
uuaggagcua ccucucacct t                                              21

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
agaaagacau guuggcuau                                                 19

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
auagccaaca ugucuuucut t                                              21

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 65
gggagaugcu cauggaaac                                                  19

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66 guuccauga gcaucccct t                                                 21

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ugcuugagcu ggagaagaa                                                  19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
uucuucucca gcucaagcat t                                               21

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uggugaacuc ugcgggaga                                                  19

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
ucucccgcag aguucaccat t                                               21
```

```
<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
cccaaccaca cggaucauut t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
aaugauccgu gugguugggt t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
uggcccugug caggcugaat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
uucagccugc acagggccat t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
aguccagaug ccaagauccu t                                              21
```

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
ggaucuuggc aucuggacut t                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
ccagacguuu accuacuggt t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
ccaguaggua aacgucuggt t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
agggcgccac agugggccut t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
aggcccacug uggcgcccut t                                              21

```
<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
gaucaagucc agaugccaat t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
uuggcaucug gacuugauct t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
uagcaaccau aacugccact t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
guggcaguua ugguugcuat t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
```
aguggagggc gccugccact t                                          21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
guggcaggcg cccuccacut t                                          21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uacaguucca gguacuucca a                                          21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
guuuccauga gcaucuccca a                                          21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uucuucucca gcucaagcaa a                                          21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uacaguucca gguacuucca a                                          21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uacaguucca gguacuucca a                                              21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uacaguucca gguacuucca a                                              21

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgatccgtgt ggttg                                                     15

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
atgatccgtg tggtt                                                     15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aatgatccgt gtggt                                                     15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caatgatccg tgtgg                                                     15

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tgtcatggtt ttcag                                                      15

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggtgtcatgg ttttc                                                      15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
aggtgtcatg gtttt                                                      15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcattttagg agcta                                                      15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ttcattttag gagct                                                      15

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tgttcatttt aggag                                                      15

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103

```
tccgtggaaa ttgca                                                          15

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
attttattcg gagct                                                          15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aacacgtcta tacgc                                                          15

<210> SEQ ID NO 106
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aggtgtcagg tttt                                                           14

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107 tttttttaggt gtcaggtttt                                                    20
```

ANTI-ADAM33 OLIGONUCLEOTIDES AND RELATED METHODS

CROSS-REFERENCE TO RELATED APPLICATIONS

This application claims the benefit of U.S. Provisional Patent Application Ser. No. 62/516,315 filed Jun. 7, 2017, the entire disclosure of which is hereby incorporated herein by reference.

SEQUENCE LISTING

The instant application contains a Sequence Listing which has been submitted electronically in ASCII format and is hereby incorporated by reference in its entirety. Said ASCII copy, created on Jun. 6, 2018, is named 60100_UM9-219PC_SL.txt and is 47,628 bytes in size.

BACKGROUND

Short interfering RNAs (siRNAs) are widely employed as a tool for inhibiting gene function. ADAM33 is a gene that has been associated with respiratory diseases, cardiovascular diseases, immune related diseases, and cancer. Unfortunately, however, the use of short interfering RNAs results in only poor silencing of ADAM33 mRNA. Accordingly, there remains a need for agents that are able to effectively silence ADAM33 mRNA with high potency.

SUMMARY

In one aspect of the invention, a synthetic antisense oligonucleotide (ASO), or a pharmaceutically acceptable salt thereof, having a target-recognition sequence that is sufficiently complementary to an ADAM33 transcript to direct cleavage of the ADAM33 transcript by RNase H is provided.

In certain exemplary embodiments, the ASO comprises a chemically modified sugar, a nucleobase, and/or a phosphate linkage.

In certain exemplary embodiments, the target-recognition sequence has the formula A-B-C, wherein A can comprise from about 0 to about 8, about 2 to about 6, or about 3 modified nucleotides, B can comprise from about 4 to about 18, about 6 to about 12, or about 9 deoxyribonucleic acid (DNA) nucleotides and/or DNA-like nucleotides, and C can comprise from about 0 to about 8, from about 2 to about 6, or about 3 modified nucleotides, and wherein the overall length of the ASO is about 10 to about 30 nucleotides.

In certain exemplary embodiments, each of the modified nucleotides is independently selected from the group consisting of a bicyclic nucleotide, and a 2'-modified nucleotide. The bicyclic nucleotide can optionally be selected from the group consisting of a locked nucleotide, an ethyl-constrained nucleotide, an alpha-L-locked nucleic acid, and a tricyclo-DNA, or any combination thereof. The 2'-modified nucleotide can optionally be selected from the group consisting of a 2'-O-methyl RNA, a 2'-O-methoxyethyl RNA, and a 2'-fluoro RNA, or any combination thereof.

In certain exemplary embodiments, A comprises from about 2 to about 4 or about 3 locked nucleotides, B comprises from about 8 to about 12 or about 9 DNA-like nucleotides, and C comprises from about 2 to about 4 or about 3 locked nucleotides.

In certain exemplary embodiments, the ASO comprises a phosphorothioate linkage.

In certain exemplary embodiments, the target-recognition sequence is at least 90% complementary to a portion of the ADAM33 transcript, or is perfectly complementary to a portion of the ADAM33 transcript.

In certain exemplary embodiments, the ASO binds: the open reading frame of the ADAM33 transcript; a 5' or 3' untranslated region of the ADAM33 transcript; the junction between the open reading frame and the untranslated region of the ADAM33 transcript; a conserved region of the ADAM33 transcript; and/or a region of the ADAM33 transcript containing a disease-associated single-nucleotide polymorphism.

In certain exemplary embodiments, the target-recognition sequence comprises a nucleic acid sequence with at least 90% sequence identity to the nucleic acid sequence set forth in any one of SEQ ID NOs:5-15.

In certain exemplary embodiments, the ASO further comprises a conjugate linked to the target-recognition sequence. The conjugate may optionally be a hydrophobic conjugate (e.g., a hexadecyloxypropyl conjugate, a cholesterol conjugate, a polyunsaturated fatty acid conjugate or the like), a tissue-targeting conjugate (e.g., a carbohydrate conjugate, a peptide conjugate or the like), or a conjugate designed to optimize pharmacokinetic parameters (e.g., a polyethylene glycol conjugate).

In certain exemplary embodiments, the conjugate remains stably linked to the target-recognition sequence after cellular internalization.

In certain exemplary embodiments, the ASO comprises a biostable nucleic acid sequence with at least 90% sequence identity to the nucleic acid sequence set forth in any one of SEQ ID NOs:11-13.

In certain exemplary embodiments, the ASO further comprises a linker between the conjugate and the target-recognition sequence, which can optionally be a cleavable linker. In certain embodiments, the cleavable linker degrades when cleaved, or is a nuclease-cleavable linker comprising a phosphodiester linkage. In certain embodiments, the nuclease-cleavable linker comprises from about 2 to about 8, or about 6 nucleotides. In certain embodiments, the cleavable linker is cleaved under reducing conditions or changing pH conditions, is cleaved by an intracellular or endosomal nuclease, or is cleaved by an intracellular or endosomal protease.

In certain exemplary embodiments, the ASO comprises a nucleic acid sequence with at least 90% sequence identity to the nucleic acid sequence set forth in any one of SEQ ID NOs:22-24.

In certain exemplary embodiments, the ADAM33 transcript is a human ADAM33 transcript.

In certain exemplary embodiments, the ASO is capable of mediating cleavage of at least about 80% or at least about 90% of ADAM33 transcripts.

In another aspect of the invention, a method of treating a subject having an ADAM33-related disorder, the method comprising administering to the subject a pharmaceutical composition comprising an effective amount of a synthetic ASO, or a pharmaceutically acceptable salt thereof, having a target-recognition sequence that is sufficiently complementary to an ADAM33 transcript to direct cleavage of the ADAM33 transcript by RNase H, and a pharmaceutically acceptable carrier, is provided.

In certain exemplary embodiments, the pharmaceutical composition is formulated for oral administration, mucosal administration, subcutaneous administration, intramuscular administration, topical administration, intravenous administration, intrathecal administration, intracerebroventricular administration, or inhalation.

In certain exemplary embodiments, the pharmaceutical composition is formulated for inhalation, and is optionally formulated as a powder.

In another aspect of the invention, a pharmaceutical composition comprising a synthetic ASO having a target-recognition sequence that is sufficiently complementary to an ADAM33 transcript to direct cleavage of the ADAM33 transcript by RNase H, and a pharmaceutically acceptable carrier, is provided.

In certain exemplary embodiments, the ASO comprises a chemically modified sugar, a nucleobase, and/or a phosphate linkage.

In certain exemplary embodiments, the target-recognition sequence has the formula A-B-C, wherein A comprises from about 0 to about 8, from about 2 to about 6, or about 3 modified nucleotides, B comprises from about 4 to about 18, from about 6 to about 12, or about 9 deoxyribonucleic acid (DNA) nucleotides and/or DNA-like nucleotides, and C comprises from about 0 to about 8, from about 2 to about 6 or about 3 modified nucleotides, and the overall length of the ASO is from about 10 to about 30 nucleotides.

In certain exemplary embodiments, each of the modified nucleotides is independently selected from the group consisting of a bicyclic nucleotide, and a 2'-modified nucleotide, optionally wherein A comprises from about 2 to about 4 or about 3 locked nucleotides, B comprises from about 8 to about 12 or about 9 DNA-like nucleotides, and C comprises from about 2 to about 4 or about 3 locked nucleotides.

In certain exemplary embodiments, the ASO comprises a phosphorothioate linkage.

In certain exemplary embodiments, the target-recognition sequence is at least 90% complementary to a portion of the ADAM33 transcript or is perfectly complementary to a portion of the ADAM33 transcript.

In certain exemplary embodiments, the ASO binds the open reading frame of the ADAM33 transcript, the junction the open reading frame and the untranslated region of the ADAM33 transcript, a conserved region of the ADAM33 transcript, and/or a region of the ADAM33 transcript containing a disease-associated single-nucleotide polymorphism.

In certain exemplary embodiments, the target-recognition sequence comprises a nucleic acid sequence with at least 90% sequence identity to the nucleic acid sequence set forth in any one of SEQ ID NOs:5-15.

In certain exemplary embodiments, the ASO further comprises a conjugate linked to the target-recognition sequence, that is optionally selected from the group consisting of a hydrophobic conjugate, a tissue-targeting conjugate, and a conjugate designed to optimize pharmacokinetic parameters.

In certain exemplary embodiments, the hydrophobic conjugate is hexadecyloxypropyl.

In certain exemplary embodiments, the ASO comprises a biostable nucleic acid sequence with at least 90% sequence identity to the nucleic acid sequence set forth in any one of SEQ ID NOs:11-13.

In certain exemplary embodiments, the ASO further comprises a linker between the conjugate and the target-recognition sequence.

In certain exemplary embodiments, the linker is a nuclease-cleavable linker comprising a phosphodiester linkage, that optionally comprises about 6 nucleotides.

In certain exemplary embodiments, the ASO comprises a nucleic acid sequence with at least 90% sequence identity to the nucleic acid sequence set forth in any one of SEQ ID NOs:22-24.

In certain exemplary embodiments, the ADAM33 transcript is a human ADAM33 transcript.

In certain exemplary embodiments, the pharmaceutical composition is formulated for oral administration, mucosal administration, subcutaneous administration, intramuscular administration, topical administration, intravenous administration, intrathecal administration, intracerebroventricular administration, or inhalation.

In certain exemplary embodiments, the pharmaceutical composition is formulated for inhalation, and is optionally formulated as a powder.

In another aspect, a method of treating a subject having an ADAM33-related disorder, the method comprising administering to the subject an effective amount of a synthetic antisense oligonucleotide (ASO) having a target-recognition sequence that is sufficiently complementary to an ADAM33 transcript to direct cleavage of the ADAM33 transcript by RNase H is provided.

In certain exemplary embodiments, the ASO comprises a chemically modified sugar, a nucleobase, and/or a phosphate linkage.

In certain exemplary embodiments, the target-recognition sequence has the formula A-B-C, wherein A comprises from about 0 to about 8 or from about 2 to about 6 modified nucleotides, B comprises from about 4 to about 18 or from about 6 to about 12 deoxyribonucleic acid (DNA) nucleotides and/or DNA-like nucleotides, and C comprises from about 0 to about 8 from about 2 to about 6 modified nucleotides; and the overall length of the ASO is from about 10 to about 30 nucleotides.

In certain exemplary embodiments, each of the modified nucleotides is independently selected from the group consisting of a bicyclic nucleotide, and a 2'-modified nucleotide, optionally wherein A comprises from about 2 to about 4 or about 3 locked nucleotides, B comprises from about 8 to about 12 or about 9 DNA-like nucleotides, and C comprises from about 2 to about 4 or about 3 locked nucleotides.

In certain exemplary embodiments, the ASO comprises a phosphorothioate linkage.

In certain exemplary embodiments, the target-recognition sequence is at least 90% complementary or perfectly complementary to a portion of the ADAM33 transcript.

In certain exemplary embodiments, the ASO binds: the open reading frame of the ADAM33 transcript; a 5' or 3' untranslated region of the ADAM33 transcript; the junction the open reading frame and the untranslated region of the ADAM33 transcript; a conserved region of the ADAM33 transcript; and/or a region of the ADAM33 transcript containing a disease-associated single-nucleotide polymorphism.

In certain exemplary embodiments, the target-recognition sequence comprises a nucleic acid sequence with at least 90% sequence identity to the nucleic acid sequence set forth in any one of SEQ ID NOs:5-15.

In certain exemplary embodiments, the ASO further comprises a conjugate linked to the target-recognition sequence that is optionally selected from the group consisting of a hydrophobic conjugate, a tissue-targeting conjugate, and a conjugate designed to optimize pharmacokinetic parameters.

In certain exemplary embodiments, the hydrophobic conjugate is hexadecyloxypropyl.

In certain exemplary embodiments, the ASO comprises a nucleic acid sequence with at least 90% sequence identity to the nucleic acid sequence set forth in any one of SEQ ID NOs:11-13.

In certain exemplary embodiments, the ASO further comprises a linker between the conjugate and the target-recognition sequence that is optionally a nuclease-cleavable linker comprising a phosphodiester linkage that optionally comprises about 6 nucleotides.

In certain exemplary embodiments, the ASO comprises a nucleic acid sequence with at least 90% sequence identity to the nucleic acid sequence set forth in any one of SEQ ID NOs:22-24.

In certain exemplary embodiments, the ADAM33 transcript is a human ADAM33 transcript.

In certain exemplary embodiments, the ADAM33-related disorder is selected from the group consisting of a respiratory disease (e.g., selected form the group consisting of asthma, chronic obstructive pulmonary disease, pulmonary fibrosis, bronchial disease, respiratory infection, interstitial lung disease, sarcoidosis, rhinitis, and any cancerous lesion of the respiratory tract, or any combination thereof), a skin disease (e.g., psoriasis, keloids, and dermatitis, or any combination thereof), a cardiovascular disease (e.g., atherosclerosis), an immune disease (e.g., diabetes or systemic lupus erythematosus), and a cancer or tumor (e.g., selected from the group consisting of gastric cancer, glioblastoma, lung cancer, breast cancer, laryngeal carcinoma, bronchial carcinoma, nasal polyps, and sinonasal papilloma, or any combination thereof), or any combination thereof.

In certain exemplary embodiments, the ADAM33-related disorder is asthma.

In certain exemplary embodiments, the method reverses/prevents inflammation-independent or inflammation-dependent airway remodeling and/or airway inflammation and/or airway hyper-responsiveness.

In certain exemplary embodiments, the ASO is administered to the subject via oral administration, mucosal administration, subcutaneous administration, intramuscular administration, topical administration, intravenous administration, intrathecal administration, intracerebroventricular administration, or inhalation.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 2A-FIG. 2D show that ADAM33 gene expression can be inhibited by siRNA and ss-siRNA oligonucleotides. (FIG. 2A) Oligonucleotide sequences: 'tt' represents a 3' terminal overhang of two deoxy thymidines, duplex siRNAs are otherwise unmodified RNA; ss-siRNA sequence modifications are '$_s$' (phosphorothioate linkage); red: 2'F-RNA; blue: 2'OMe-RNA; purple: 2'-O-MOE-RNA; green: LNA; p (5'-phosphate). For siRNA duplexes, passenger strands are listed on top and guide strands underneath. S represents sense strand and AS represents antisense strand. FIG. 2A discloses SEQ ID NOS 59-92, respectively, in order of appearance. (FIG. 2B) qRT-PCR results from a screen of siRNA duplexes show that very few siRNA sequences were active against this target. (FIG. 2C) qRT-PCR results showing gene silencing efficacy of ss-siRNA analogues of the three most potent duplex siRNAs, in comparison with the parent duplexes. (FIG. 2D) qRT-PCR results comparing potencies of different chemical modification schemes on ss-siRNA activity. For all figure parts, error bars represent standard deviation of biological replicates. All oligonucleotides were transfected at 50 nM into MRC-5 lung fibroblasts using Lipofectamine RNAiMAX. All results were normalized to a scrambled siRNA duplex control.

FIG. 3A-FIG. 3C show that LNA gapmers are highly potent when transfected with a cationic lipid. (FIG. 3A) LNA gapmer sequence modifications are 's' (phosphorothioate linkage); green uppercase: LNA; lower case: DNA. FIG. 3A discloses SEQ ID NOS 93-105, respectively, in order of appearance. (FIG. 3B) qRT-PCR results showing gene silencing by LNA gapmers at 50 nM. All results were normalized to a scrambled siRNA duplex control. Error bars are standard deviation of biological replicates. (FIG. 3C) qRT-PCR results showing dose response analysis of 33-0 and 33-R. Results were normalized to a scrambled LNA gapmer control. Error bars for the dose responses represent standard deviation of technical replicates.

(FIG. 4A) qRT-PCR time course results of gymnotic delivery of ASO 33-0. Oligonucleotides were delivered at 1 μM dose and normalized to a non-treated control. Error bars are standard deviation of technical replicates. The degree of knockdown was intentionally chosen to be suboptimal (by using 1 μM rather than 3 μM ASO) to allow better discrimination of any differences in efficacy. (FIG. 4B) Gene silencing measured by qRT-PCR after gymnotic delivery. Oligonucleotides are delivered to MRC-5 cells at 3 μM dose and normalized to a non-treated control (NT). Error bars represent the standard deviation of biological replicates.

FIG. 5A-FIG. 5D show that lipid-conjugated LNA gapmers show reduced potency unless the lipid is joined to the ASO via a biocleavable linkage. (FIG. 5A) Synthesis and structure of hexadecyloxypropyl LNA conjugates. Reagents and conditions: (i) NaH, $CH_3(CH_2)_{15}Br$, cat. KI; (ii) $^iPr_2NP(O(CH_2)_2CN)Cl$, DIPEA, $CH_2Cl_2$; (iii) standard oligonucleotide synthesis conditions. (FIG. 5B) Dynamic light scattering shows that addition of a lipid tail causes self-assembly of ASOs into larger structures (comparing 33-0, red bars, with its biostable conjugate, black bars). (FIG. 5C) qRT-PCR results showing dose response analysis of A33-N, O, and P and both types of lipid conjugates, after gymnotic delivery to MRC-5 cells at concentrations from 3 to 0.11 μM. Results were normalized to non-treated control sample (NT). Error bars represent standard deviation of biological replicates. (FIG. 5D) A table providing the sequences of the biostable and biocleavable conjugated LNA gapmers (SEQ ID NOS 106, 23, 24, 107, 34 and 35, respectively, in order of appearance).

(FIG. 6A) Oligonucleotides were delivered at 50 nM with Lipofectamine RNAiMAX. Error bars represent the standard deviation of biological replicates. Mouse-targeted sequences are shown in Table 1 (see, experimental section), and were made as fully phosphorothioate (PS) 3-9-3 LNA gapmers (the same chemical architecture as the human sequences). The sequence of LNA-scr2, also a PS 3-9-3 gapmer, is AACacgtctataCGC (SEQ ID NO:54). 33-0 is the human sequence from FIG. 3, included as an additional negative control. (FIG. 6B) A table providing the sequences of the ASOs used (SEQ ID NOS 55-58, respectively, in order of appearance).

DETAILED DESCRIPTION

Figure 1:
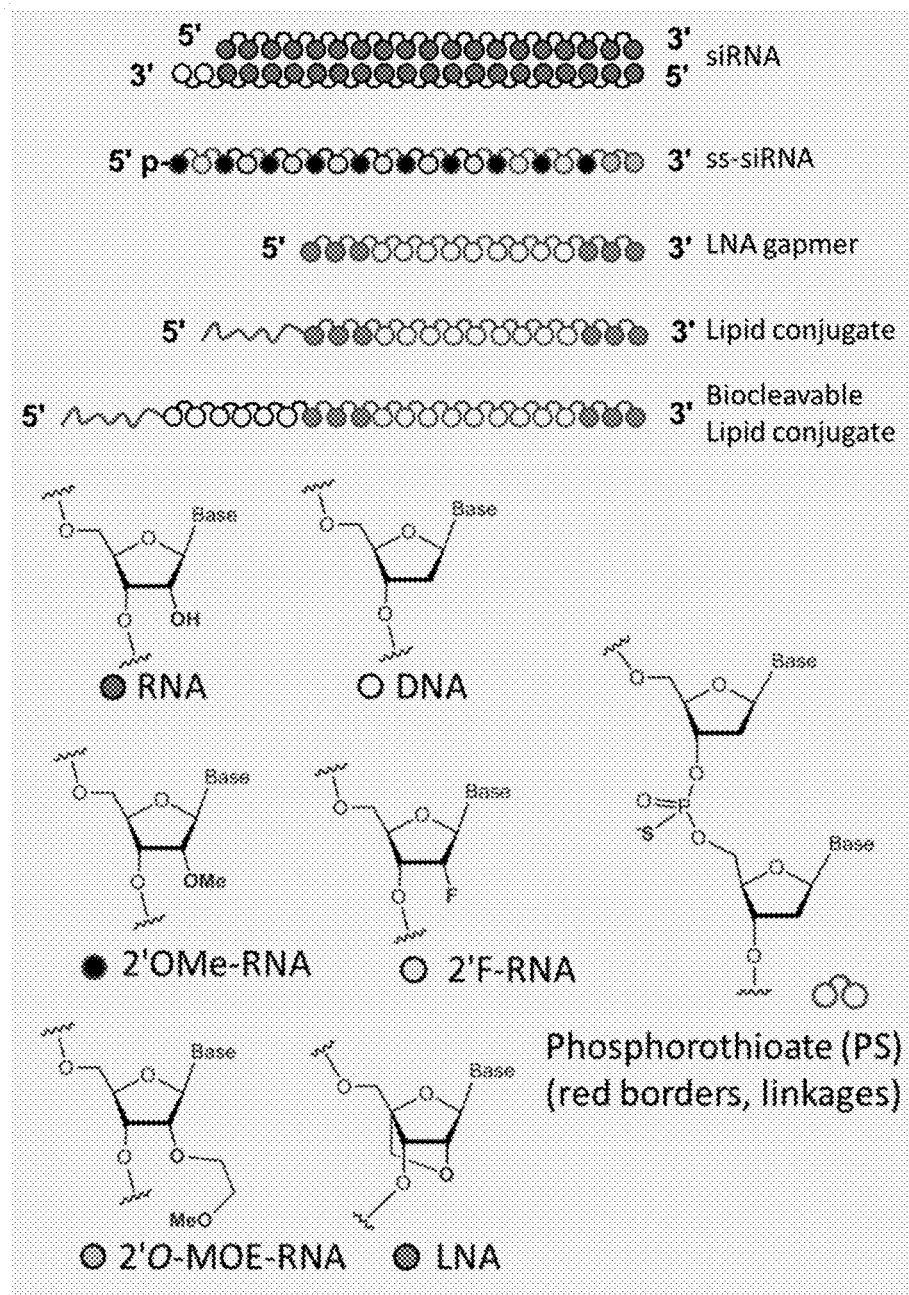
FIG. 1 depicts the types of gene silencing oligonucleotides (top) and chemical modifications (bottom) used. p=phosphate.

The present disclosure provides antisense compounds, methods, and compositions for silencing ADAM33 mRNA. The invention described herein is largely based on the finding that certain RNase H-dependent antisense compounds provide unexpected improvement in the silencing of ADAM33 mRNA over siRNAs. The present disclosure provides antisense compounds, methods, and compositions for the treatment, prevention, or amelioration of diseases, disorders, and conditions associated with ADAM33 in a subject in need thereof. Also contemplated are antisense compounds and methods for the preparation of a medicament for the treatment, prevention, or amelioration of a disease, disorder, or condition associated with ADAM33. ADAM33-related diseases, disorders, and conditions include, without limitation, respiratory diseases, skin diseases, cardiovascular diseases, immune diseases, cancers or tumors, or any combination thereof.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, $2^{nd}$ edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). An RNA nucleotide refers to a single ribonucleotide. The term "DNA" or "DNA molecule" or "deoxyribonucleic acid molecule" refers to a polymer of deoxyribonucleotides. A DNA nucleotide refers to a single deoxyribonucleotide. As used herein, the term "DNA-like" refers to a conformation of, e.g. a modified nucleoside or nucleotide which is similar to the conformation of a corresponding unmodified DNA unit. For example, a DNA-like nucleotide may refer to a conformation of a modified deoxyribonucleotide similar to a corresponding unmodified deoxyribonucleotide. Examples of DNA-like nucleotides include, without limitation, e.g., 2'-deoxyribonucleotides, 2'-deoxy-2'-substituted arabinonucleotides (e.g., 2'-deoxy-2'-fluoroarabinonucleotides, also known in the art as 2'F-ANA or FANA), and corresponding phosphorothioate analogs. As used herein, the term "RNA-like" refers to a conformation of, e.g. a modified nucleoside or nucleotide which is similar to the conformation of a corresponding unmodified RNA unit. RNA-like conformations may adopt an A-form helix while DNA-like conformations adopt a B-form helix. Examples RNA-like nucleotides include, without limitation, e.g., 2'-substituted-RNA nucleotides (e.g., 2'-fluoro-RNA nucleotides also known in the art as 2'F-RNA), locked nucleic acid (LNA) nucleotides (also known in the art as bridged nucleic acids or bicyclic nucleotides), 2'-fluoro-4'-thioarabinonucleotide (also known in the art as 4'S-FANA nucleotides), 2'-O-alkyl-RNA, and corresponding phosphorothioate analogs.

DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary modified nucleotides are modified at any position so as to alter certain chemical properties of the nucleotide yet retain the ability of the modified nucleotide to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Modified nucleotides also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotides such as those described in Herdewijn, Antisense Nucleic Acid Drug Dev., 2000 Aug. 10(4):297-310.

Modified nucleotides may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein, the terms "unmodified nucleotide" or "non-modified nucleotide" refers to a nucleotide composed of naturally occurring nucleobases, sugar moieties, and internucleoside linkages. In some embodiments, a non-modified nucleotide is an RNA nucleotide (i.e. β-D-ribonucleoside) or a DNA nucleotide (i.e. β-D-deoxyribonucleoside).

The term "oligonucleotide" refers to a short polymer of nucleotides and/or modified nucleotides. As discussed above, the oligonucleotides may be linked with linkages which result in a lower rate of hydrolysis as compared to an oligonucleotide linked with phosphodiester linkages. For example, the nucleotides of the oligonucleotide may comprise methylenediol, ethylene diol, oxymethylthio, oxyethylthio, oxycarbonyloxy, phosphorodiamidate, phosphoroamidate, and/or phosphorothioate linkages. Alterations or modifications of the oligonucleotide can further include addition of non-nucleotide material, such as to the end(s) of the oligonucleotide or internally (at one or more nucleotides of the oligonucleotide).

As used herein, the term "antisense compound" refers to a compound which is capable of inhibiting or "silencing" the expression of a target gene. In certain embodiments, the antisense compound is capable of preventing complete processing (e.g., the full translation and/or expression) of an mRNA molecule through a post-transcriptional silencing mechanism. Antisense compounds include, without any limitation, antisense oligonucleotides, gapmer molecules, and dual-function oligonucleotides as well as precursors thereof. In some embodiments, the antisense compound directs a target nucleic acid for cleavage by ribonuclease H (RNase H). For example, an antisense compound of the present disclosure can be an antisense oligonucleotide that directs cleavage of an ADAM33 transcript by RNase H. RNase H is a family of non-sequence-specific endonuclease enzymes that catalyze the cleavage of RNA in an RNA/DNA substrate via a hydrolytic mechanism.

The term "gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments." "Chimeric antisense compound" means an antisense compound that has at least two chemically distinct regions.

As used herein, the term "target gene" is a gene whose expression is to be substantially inhibited or "silenced." This silencing can be achieved by RNA silencing, e.g., by cleaving mRNA corresponding to a target gene or translational repression of the target gene. The term "non-target gene" is a gene whose expression is not to be substantially silenced. For example, a target gene of the present invention is ADAM33, and a non-target gene of the present invention is a gene that is not ADAM33. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g., an orthologue or paralogue) of the target gene.

The term "antisense activity" means any detectable or measurable activity attributable to the hybridization of an antisense compound to its target nucleic acid. In some embodiments, antisense activity is a decrease in the amount or expression of a target nucleic acid or protein encoded by such target nucleic acid. "Antisense compound" means an oligomeric compound that is capable of undergoing hybridization to a target nucleic acid through hydrogen bonding. As used herein, "antisense oligonucleotide" means a single-stranded oligonucleotide having a nucleobase sequence that permits hybridization to a corresponding region or segment of a target nucleic acid.

The term "antisense inhibition" means reduction of target nucleic acid levels or target protein levels in the presence of an antisense compound having a target-recognition sequence that is sufficiently complementary to a target nucleic acid compared to target nucleic acid levels or target protein levels in the absence of the antisense compound. A target nucleic acid can be any nucleic acid. For example, a target nucleic acid of the present invention can be an ADAM33 transcript.

The term "target-recognition sequence" refers to the portion of an antisense compound that recognizes a target nucleic acid. The target-recognition sequence has a nucleobase sequence that permits hybridization to a corresponding region or segment of a target nucleic acid.

As used herein, the "5' end," as in the 5' end of the open reading frame of an ADAM33 transcript, refers to the 5' terminal nucleotides, of the open reading frame of the ADAM33 transcript. As used herein, the "3' end," as in the 3' end of the open reading frame of an ADAM33 transcript, refers to the 3' terminal nucleotides, of the open reading frame of the ADAM33 transcript.

The term "conserved region" refers to a portion, or portions, of a nucleic acid sequence that is conserved, i.e. a portion, or portions of the nucleic acid sequence having a similar or identical sequence across species. A conserved region may be computationally identified, e.g., using any sequence alignment software available in the art.

As used herein, the term "sufficiently complementary" means that the RNA silencing agent has a sequence (e.g., an antisense oligonucleotide having a target-recognition sequence) which is sufficient to bind the desired target mRNA (e.g., an ADAM33 transcript), and to trigger the RNA silencing of the target mRNA (e.g., direct cleavage of the target mRNA by RNase H). For example, a target-recognition sequence with at least 90% complementarity to a target nucleic acid sequence (e.g., a portion of an ADAM33 transcript) may be sufficiently complementary to trigger silencing of the ADAM33 transcript. The term "perfectly complementary" refers to, e.g., a target-recognition sequence with 100% complementarity to a target nucleic acid sequence. Complementary nucleic acid molecules hybridize to each other. The term "hybridization" means the annealing of complementary nucleic acid molecules. In certain embodiments, complementary nucleic acid molecules include an antisense compound and a target nucleic acid.

The term "about" or "approximately" means within 20%, such as within 10%, within 5%, or within 1% or less of a given value or range.

As used herein, "administer" or "administration" refers to the act of injecting or otherwise physically delivering a substance as it exists outside the body (e.g., an antisense compound provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms, e.g., damage to the involved tissues and airways.

As used herein, the term "composition" is intended to encompass a product containing the specified ingredients (e.g., an antisense compound provided herein) in, optionally, the specified amounts, as well as any product which results, directly or indirectly, from combination of the specified ingredients in, optionally, the specified amounts.

"Effective amount" means the amount of active pharmaceutical agent (e.g., an antisense compound of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject is can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sports animals, and pets. In one embodiment, the subject is a mammal, such as a human, having an ADAM33-related disorder (e.g., asthma). In another embodiment, the subject is a mammal, such as a human, that is at risk for developing an ADAM33-related disorder.

As used herein, the term "therapy" refers to any protocol, method and/or agent that can be used in the prevention, management, treatment and/or amelioration of a disease or a symptom related thereto, such as an ADAM33-related disorder (e.g., asthma). In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as an ADAM33-related disorder known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, such as an ADAM33-related disorder, resulting from the administration of one or more therapies (including, but not limited to, the administration of one or more prophylactic or therapeutic agents, such as an antisense oligonucleotide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Antisense Compounds

The present disclosure provides an antisense compound that is capable of mediating cleavage of at least 50%, at least 55%, at least 60%, at least 65%, at least 70%, at least 75%, at least 80%, at least 85%, at least 90%, at least 95% or more of ADAM33 transcripts. In one embodiment, the antisense compound is capable of mediating cleavage of at least 80% of ADAM33 transcripts. In one embodiment, the antisense compound is capable of mediating cleavage of at least 90% of ADAM33 transcripts.

In certain embodiments, antisense compounds that is capable of mediating cleavage of an ADAM33 transcript or portion thereof, have chemically modified subunits arranged in patterns, or motifs, to confer to the antisense compounds properties such as enhanced the inhibitory activity, increased binding affinity for a target nucleic acid, or resistance to degradation by in vivo nucleases.

In some embodiments, an antisense compound of the present disclosure is an antisense oligonucleotide. Chimeric antisense oligonucleotides typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex. In some embodiments, an antisense compound of the present disclosure is a chimeric antisense oligonucleotide having a gapmer motif. In a gapmer an internal region having a plurality of nucleotides that supports RNaseH cleavage is positioned between external regions having a plurality of nucleotides that are chemically distinct from the nucleosides of the internal region.

In some embodiments, the present disclosure provides a synthetic antisense oligonucleotide having a target-recognition sequence that is sufficiently complementary to an ADAM33 transcript or portion thereof, to direct cleavage of the ADAM33 transcript by RNase H. The target-recognition sequence of the antisense oligonucleotide can be the full length of the antisense oligonucleotide, or a portion thereof. In some embodiments, the antisense oligonucleotide comprises a gapmer motif.

In the case of an antisense compound having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$ (i.e., OMe), among others), and bicyclic sugar modified nucleosides (such bicyclic sugar modified nucleosides may include those having a 4'-$(CH_2)_n$—O-2' bridge, where n=1 or n=2). In some embodiments, each distinct region comprises uniform sugar moieties.

The gapmer motif can be described using the formula "A-B-C", where "A" represents the length of the 5' wing region, "B" represents the length of the gap region, and "C" represents the length of the 3' wing region. As such, in some embodiments, an antisense oligonucleotide of the present disclosure has the formula:

A-B-C.

As used herein, a gapmer described as "A-B-C" has a configuration such that the gap segment is positioned immediately adjacent each of the 5' wing segment and the 3' wing segment. Thus, no intervening nucleotides exist between the 5' wing segment and gap segment, or the gap segment and the 3' wing segment.

In some embodiments, the 5' wing region represented by "A" comprises from about 0 to about 8 modified nucleotides, e.g., from about 1 to about 6 modified nucleotides. For example, the 5' wing region represented by "A" can be 0, 1, 2, 3, 4, 5, 6, 7, or 8 nucleotides in length. In some embodiments, the 3' wing region represented by "C" comprises about 0 to about 8 modified nucleotides, e.g., from about 1 to about 6 modified nucleotides. For example, the 3' wing region represented by "C" can be 0, 1, 2, 3, 4, 5, 6, 7, or 8 nucleotides in length. In some embodiments, "A" and "C" are the same, in some embodiments, they are different.

In some embodiments, the gap region represented by "B" comprises from about 4 to about 18 DNA nucleotides and/or DNA-like nucleotides, e.g., from about 4 to about 12 DNA nucleotides and/or DNA-like nucleotides. For example, the gap region represented by "B" can be 4, 5, 6, 7, 8, 9, 10, 11, 12, 13, 14, 15, 16, 17, or 18 DNA nucleotides and/or DNA-like nucleotides in length. Thus, an antisense oligonucleotide of the present disclosure having a target-recognition sequence with the formula "A-B-C" include, but are not limited to the following gapmer formats, for example 1-4-1 (i.e., one nucleotide—four nucleotides—one nucleotide), 1-5-1, 1-6-1, 1-7-1, 1-8-1, 1-9-1, 1-10-1, 1-11-1, 1-12-1, 2-4-2, 2-5-2, 2-6-2, 2-7-2, 2-8-2, 2-9-2, 2-10-2, 2-11-2, 2-12-2, 3-4-3, 3-5-3, 3-6-3, 3-7-3, 3-8-3, 3-9-3, 3-10-3, 3-11-3, 3-12-3, 4-4-4, 4-5-4, 4-6-4, 4-7-4, 4-8-4, 4-9-4, 4-10-4, 4-11-4, 4-12-4, 5-4-5, 5-5-5, 5- 6-5, 5-7-5, 5-8-5, 5-9-5, 5-10-5, 5-11-5, 5-12-5, 6-4-6, 6-5-6, 6-6-6, 6-7-6, 6-8-6, 6-9-6, 6-10-6, 6-11-6, or 6-12-6.

In certain embodiments, antisense compounds targeted to an ADAM33 nucleic acid possess a 3-9-3 gapmer format. In some embodiments, the antisense compound is an antisense oligonucleotide having a target-recognition sequence with the 3-9-3 format that is sufficiently complementary to an ADAM33 transcript, or a portion thereof, to direct cleavage of the ADAM33 transcript by RNase H. In some embodiments, the target-recognition sequence has the formula "A-B-C", wherein "A" comprises about 3 modified nucleotides, "B" comprises about 9 DNA nucleotides and/or DNA-like nucleotides, and "C" comprises about 3 modified nucleotides. In some embodiments, the target-recognition sequence has the formula "A-B-C", wherein "A" comprises 3 locked nucleotides, "B" comprises 9 DNA nucleotides and/or DNA-like nucleotides, and "C" comprises 3 locked nucleotides. In some embodiments, the target-recognition sequence has the formula "A-B-C", wherein "A" comprises 3 locked nucleotides, "B" comprises 9 DNA-like nucleotides, and "C" comprises 3 locked nucleotides.

In some embodiments, antisense compounds that target an ADAM33 nucleic acid possess a "wingmer" motif. The wingmer motif can be described using the formula "X—Y" or "Y—X", where "X" represents the length of the wing region, and "Y" represents the length of the gap region. As such, in some embodiments, an antisense oligonucleotide of the present disclosure has the formula:

X—Y, or

Y—X.

As used herein, a wingmer described as "X—Y" or "Y—X" has a configuration such that the gap segment is positioned immediately adjacent to the wing segment. Thus, no intervening nucleotides exist between the wing segment and the gap segment. Non-limiting examples of wingmer configurations of an antisense compound of the present disclosure include, e.g., 1-10, 1-11, 1-12, 2-9, 2-10, 2-11, 2-12, 3-8, 3-9, 3-10, 3-11, 3-12, 4-7, 4-8, 4-9, 4-10, 4-11, 4-12, 5-6, 5-7, 5-8, 5-9, 5-10, 5-11, or 5-12.

In some embodiments, antisense compounds targeted to an ADAM33 nucleic acid possess a gap-widened motif. As used herein, "gap-widened" refers to an antisense compound having a gap segment of 12 or more contiguous DNA nucleotides and/or DNA-like nucleotides adjacent to a wing region. In the case of a gap-widened gapmer, the gapmer comprises a gap region having 12 or more contiguous DNA nucleotides and/or DNA-like nucleotides positioned between and immediately adjacent to the 5' and 3' wing segments. In the case of a gap-widened wingmer, the wingmer comprises a gap region having 12 or more contiguous DNA nucleotides and/or DNA-like nucleotides positioned immediately adjacent to the wing segment.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ADAM33 nucleic acid comprise one or more modified internucleoside linkages. In certain embodiments, the modified internucleoside linkages are phosphorothioate linkages.

In certain embodiments, each internucleoside linkage of an antisense compound is a phosphorothioate internucleoside linkage.

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F (i.e., 2'-fluoro), 2'-OCH$_3$ (i.e., 2'-O-methyl) and 2'-O(CH$_2$)$_2$OCH$_3$ (i.e., 2'-O-methoxyethyl) substituent groups. The substituent at the 2' position can also be selected from allyl, amino, azido, thio, O-allyl, O—C1-C10 alkyl, OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C1-C10 alkyl. 2'-modified nucleotides are useful in the present invention, for example, 2'-O-methyl RNA, 2'-O-methoxyethyl RNA, 2'-fluoro RNA, and others envisioned by one of ordinary skill in the art.

Examples of bicyclic nucleic acids (BNAs) include without limitation nucleosides comprising a bridge between the 4' and the 2' ribosyl ring atoms. A BNA comprising a bridge between the 4' and 2' ribosyl ring atoms can be referred to as a locked nucleic acid (LNA), and is often referred to as inaccessible RNA. As used herein, the term "locked nucleotide" or "locked nucleic acid (LNA)" comprises nucleotides in which the 2' deoxy ribose sugar moiety is modified by introduction of a structure containing a heteroatom bridging from the 2' to the 4' carbon atoms. The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribopentofuranosyl moiety. In certain embodiments, antisense compounds provided herein include one or more BNA nucleosides wherein the bridge comprises one of the formulas: 4'-(CH$_2$)—O-2' (LNA); 4'-(CH$_2$)—S-2'; 4'-(CH$_2$)—O-2' (LNA); 4'-(CH$_2$)2-O-2' (ENA); 4'-C(CH$_3$)2-O-2' (see PCT/US2008/068922); 4'-CH(CH$_3$)—O-2' and 4'-CH(CH$_2$OCH$_3$)—O-2' (see U.S. Pat. No. 7,399,845, issued on Jul. 15, 2008); 4'-CH$_2$—N(OCH$_3$)-2' (see PCT/US2008/064591); 4'-CH$_2$—O—N(CH$_3$)-2' (see published U.S. Patent Application US2004-0171570, published Sep. 2, 2004);

4'-CH$_2$—N(R)—O-2' (see U.S. Pat. No. 7,427,672, issued on Sep. 23, 2008); 4'-CH$_2$—C(CH$_3$)-2' and 4'-CH$_2$—C(=CH$_2$)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In some embodiments, antisense compounds provided herein include one or more 2', 4'-constrained nucleotides. For example, antisense compounds provided by the present disclosure include those having one or more constrained ethyl (cEt) or constrained methoxyethyl (cMOE) nucleotides. In some embodiments, antisense compounds provided herein are antisense oligonucleotides comprising one or more constrained ethyl (cEt) nucleotides. The terms "constrained ethyl" and "ethyl-constrained" are used interchangeably.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

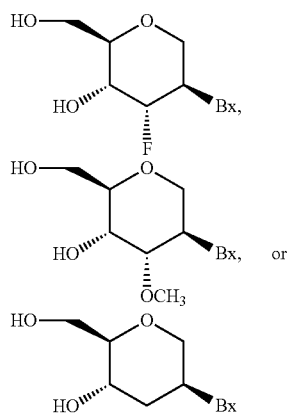

Many other bicyclo and tricyclo sugar surrogate ring systems are also know in the art that can be used to modify nucleosides for incorporation into antisense compounds (see for example review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target.

In certain embodiments, antisense compounds targeted to an ADAM33 nucleic acid comprise one or more kinds of modified nucleotides. In one embodiment, antisense compounds targeted to an ADAM33 nucleic acid comprise 2'-modified nucleotides. In one embodiment, antisense compounds targeted to an ADAM33 nucleic acid comprise a 2'-O-methyl RNA, a 2'-O-methoxyethyl RNA, or a 2'-fluoro RNA. In one embodiment, antisense compounds targeted to an ADAM33 nucleic acid comprise tricyclo-DNA. Tricyclo-DNA belongs to a class of constrained DNA analogs that display improved hybridizing capacities to complementary RNA, see, e.g., Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova *et al.*, *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., *JACS.* 124:5993-6002 (2002). In one embodiment, antisense compounds targeted to an ADAM33 nucleic acid comprise a locked nucleotide, an ethyl-constrained nucleotide, or an alpha-L-locked nucleic acid. Various alpha-L-locked nucleic acids are known by those of ordinary skill in the art, and are described in, e.g., Sorensen et al., *J. Am. Chem. Soc.* (2002) 124(10):2164-2176.

In certain embodiments, antisense compounds targeted to an ADAM33 nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format, wherein 9 non-locked nucleotides are flanked by 3 locked nucleotides on each side.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ADAM33 nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format, wherein 9 non-locked nucleotides are flanked by 3 locked nucleotides on each side. In certain embodiments, antisense compounds targeted to an ADAM33 nucleic acid comprise one or more modified nucleotides. In some embodiments, the modified nucleotide is 5-methylcytosine. In certain embodiments, each cytosine is a 5-methylcytosine.

In some embodiments, an antisense compound of the present disclosure directs cleavage of an ADAM33 transcript by RNase H. In such embodiments, the antisense compound may be referred to as an RNase H-dependent antisense compound. In some embodiments the antisense compound is an RNase H-dependent antisense oligonucleotide. In some embodiments, an antisense oligonucleotide of the present disclosure is an RNase H-dependent antisense oligonucleotide, and may be a single-stranded, chemically modified oligonucleotide that binds to a complementary sequence in the target mRNA (e.g., ADAM33 mRNA). An RNase H-dependent antisense oligonucleotide of the present disclosure reduces expression of a target gene by RNase H-mediated cleavage of the target mRNA, and by inhibition of translation by steric blockade of ribosomes. In some embodiments, an antisense compound of the present disclosure is capable of mediating cleavage of at least 50%, at least 55%, at least 60%, at least 65%, at least 70%, at least 75%, at least 80%, at least 85%, at least 90%, at least 95% or more of ADAM33 transcripts by RNase-H. In one embodiment, the antisense compound is capable of mediating cleavage of at least 80% of ADAM33 transcripts by RNase-H. In one embodiment, the antisense compound is capable of mediating cleavage of at least 90% of ADAM33 transcripts by RNase-H.

In certain embodiments, an antisense compound that targets an ADAM33 transcript is from about 6 to about 24 subunits in length. In other embodiments, the antisense compound that targets an ADAM33 transcript is from about 8 to about 80 subunits in length. For example, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compounds are less than 40 linked subunits in length. In some embodiments, the antisense compounds are from about 12 to about 25 linked subunits in length. In some embodiments, the antisense compounds are from about 15 to about 20 linked subunits in length. In some embodiments, the antisense compound is an antisense oligonucleotide that targets an ADAM33 transcript, and the linked subunits are linked nucleotides.

In certain embodiments antisense compounds targeted to an ADAM33 transcript may be shortened or truncated. For example, a single subunit may be deleted from the 5' end (5' truncation), or alternatively from the 3' end (3' truncation). A shortened or truncated antisense compound targeted to an ADAM33 transcript may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Branched Antisense Compounds

The present disclosure also provides branched antisense compounds comprising at two or more target-recognition sequences that targets a portion of an ADAM33 nucleic acid. A branched antisense compound of the present disclosure may be, e.g., a branched antisense oligonucleotide compound.

As used herein, the term "branched antisense compound" or "branched antisense oligonucleotide" refers to two or more antisense compounds or antisense oligonucleotides are described herein, connected together.

In one embodiment, a branched oligonucleotide compound comprises two or more target-recognition sequences, wherein the target-recognition sequences are connected to one another by one or more moieties selected from a linker, a spacer, and a branching point. Target-recognition sequences are described herein. In some embodiments, the branched oligonucleotide compound comprises 2, 3, 4, 5, 6, 7, 8, or more target-recognition sequences, wherein each target-recognition sequences comprises a 5' end and a 3' end, and each target-recognition sequence is independently connected to a linker, a spacer, or a branching point at the 5' end or the 3' end. In some embodiments, each target-recognition sequence is connected to a linker, a spacer, or a branching point at the 5' end. In some embodiments, each target-recognition sequence is connected to a linker, a spacer, or a branching point at the 3' end. In another embodiment, each target-recognition sequence is connected to a linker, a spacer, or a branching point. In some embodiments, each of the target-recognition sequences are antisense compounds and/or oligonucleotides that target a portion of an ADAM33 nucleic acid.

In some embodiments, a branched oligonucleotide compound of the present disclosure has the formula

wherein N represents a target-recognition sequence of the present disclosure; n represents an integer, e.g., 2, 3, 4, 5, 6, 7, or 8; and L represents a linker selected from an ethylene glycol chain, an alkyl chain, a peptide, RNA, DNA, a phosphate, a phosphonate, a phosphoramidate, an ester, an amide, a triazole, and any combination thereof.

In some embodiments, a branched oligonucleotide compound of the present disclosure has the formula

wherein the compound optionally further comprises one or more branching points B, and wherein the compound optionally further comprises one or more spacers S. In such embodiments, each of the one or more branching points B independently represents a polyvalent organic species or derivative thereof, and each of the one or more spacers S is independently selected from an ethylene glycol chain, an alkyl chain, a peptide, RNA, DNA, a phosphate, a phosphonate, a phosphoramidate, an ester, an amide, a triazole, and any combination thereof. For example, a branched oligonucleotide compound of the present disclosure having the formula L-(N)n has a structure, not to be limited in any fashion, e.g.,

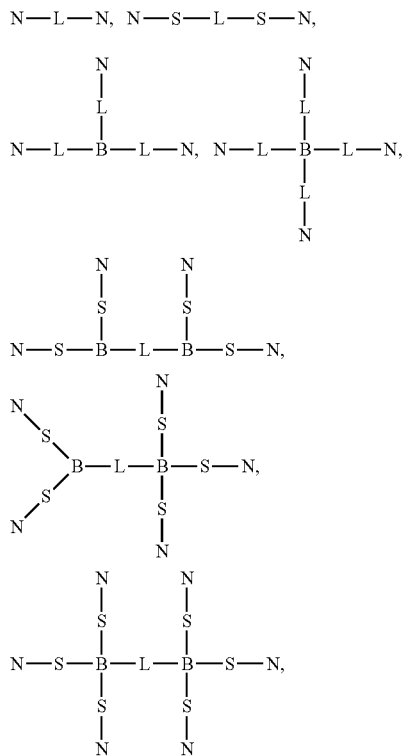

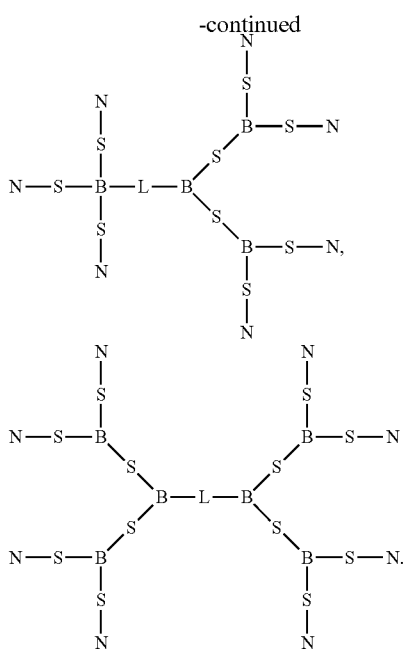

Target-Recognition Sequences

The present disclosure provides an antisense compound comprising a target-recognition sequence that targets a portion of a disintegrin and metalloproteinase domain-containing protein 33 (ADAM33) nucleic acid (e.g., ADAM33 mRNA). In certain embodiments, an antisense compound has a nucleobase sequence that, when written in the 5' to 3' direction, comprises the reverse complement of a portion of an ADAM33 nucleic acid. In some embodiments, an antisense compound is an antisense oligonucleotide. In certain such embodiments, an antisense oligonucleotide has a nucleobase sequence that, when written in the 5' to 3' direction, comprises the reverse complement of a portion of an ADAM33 nucleic acid.

In certain embodiments, a target region is a structurally defined region of an ADAM33 nucleic acid. For example, a target region may encompass a 3' untranslated region (UTR), a 5' untranslated region (UTR), an exon, an intron, an exon/intron junction, a coding region, a translation initiation region, translation termination region, or other defined nucleic acid region, for example, an open reading frame, or the junction between an open reading frame and an untranslated region and any combinations thereof. The structurally defined regions for ADAM33 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

In some embodiments, a target region may encompass a disease-associated single-nucleotide polymorphism (SNP), and an antisense compound of the present disclosure binds a region of an ADAM33 transcript containing a disease-associated SNP. Various ADAM33 SNPs have been curated into the SNP database (dbSNP) for the National Center for Biotechnology Information (NCBI). Various ADAM33 SNPs have been identified that are associated with certain diseases. For example, asthma-associated ADAM33 SNPs have been described in, e.g., Werner et al., *Clin. Exp. Allergy* (2004) 34(1):26-31; Sharma et al., *Allergy Rhinol (Provi-*

*dence*) (2011) 2(2):e63-e70; Al Al-Khayyat et al., *Ann. Saudi Med.* (2012) 32(5):479-486; and Martinez et al., *Invest. Clin.* (2016) 57(2):176-186. ADAM33 SNPs associated with susceptibility to ventilator impairment in wood dust-exposed workers have been described in, e.g., Saad-Hussein, et al., *Human Exp. Toxicol.* (2015) 35(9):966-973. ADAM33 SNPs associated with keloid scars have been described in, e.g., Han, et al., *Cell. Phys. Biochem.* (2014) 34:981-987. ADAM33 SNPs associated with systemic lupus erythematosus have been described in, e.g., Kim et al., *J. Rheum. Dis.* (2016) 23(2):88-95. ADAM33 SNPs associated with allergic rhinitis have been described in, e.g., Zihlif et al., *Gene* (2013) 531(2):462-466; and Chen et al., *PLoS One* (2014) 9(4):e95033. ADAM33 SNPs associated with the risk of idiopathic pulmonary fibrosis have been described in, e.g., Uh et al., *Lung* (2014) 192(4):525-532.

Targeting includes determination of at least one target segment to which an antisense compound hybridizes, such that a desired effect occurs. In certain embodiments, the desired effect is a reduction in mRNA target nucleic acid levels, i.e., a reduction in ADAM33 mRNA levels. In certain embodiments, the desired effect is reduction of levels of protein encoded by the target nucleic acid or a phenotypic change associated with the target nucleic acid, e.g., a reduction in the level of ADAM33 protein.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous.

Suitable target segments may be found within a 5' UTR, a coding region, a 3' UTR, an intron, an exon, and/or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid (e.g., ADAM33) to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences). The determination of suitable target segments may include comparison of the sequences of a target nucleic acid (e.g., ADAM33 mRNA) across several species. For example, various sequence alignment software are known in the art and can be used to identify regions of similar or identical sequence across species.

There may be variation in activity (e.g., as defined by percent reduction of target nucleic acid levels) of the antisense compounds within an active target region. In certain embodiments, reduction in ADAM33 mRNA levels is indicative of inhibition of ADAM33 expression. Reductions in levels of an ADAM33 protein are also indicative of inhibition of target mRNA expression. Further, phenotypic changes are indicative of inhibition of ADAM33 expression. In some embodiments, reduction in the mRNA levels of a gene that operates within an ADAM33 genetic pathway can indicate inhibition of ADAM33 expression. For example, reduction in the mRNA levels of a downstream component of an ADAM33 genetic pathway is indicative of inhibition of ADAM33.

An antisense compound and a target nucleic acid (e.g., an ADAM33 transcript or portion thereof) are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ADAM33 transcript or portion thereof).

Non-complementary nucleobases between an antisense compound and an ADAM33 nucleic acid may be tolerated provided that the antisense compound remains able to specifically hybridize to a target nucleic acid. Moreover, an antisense compound may hybridize over one or more segments of an ADAM33 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an ADAM33 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region (e.g., an equal length portion of an ADAM33 transcript), and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to an ADAM33 nucleic acid, or a target region, or a target segment or target sequence thereof. As used herein, "fully complementary" or "perfectly complementary" means each nucleobase of an antisense compound is capable of precise base pairing with the corresponding nucleobases of a target nucleic acid. For example, a 20 nucleobase antisense compound is perfectly complementary to a target sequence that is 400 nucleobases long, so long as there is a corresponding 20 nucleobase portion of the target nucleic acid that is fully complementary to the antisense compound. Perfectly complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

In some embodiments, the ADAM33 nucleic acid is a human ADAM33 transcript. In some embodiments, the human ADAM33 transcript is any of the sequences set forth in GenBank NCBI Reference Sequence: NM_001282447.2 (incorporated herein as SEQ ID NO:1), GenBank NCBI Reference Sequence: NM_025220.4 (incorporated herein as SEQ ID NO:2), GenBank NCBI Reference Sequence: NM_153202.3 (incorporated herein as SEQ ID NO:3), and GenBank NCBI Reference Sequence: NM_025220.3 (incorporated herein as SEQ ID NO:4). In some embodiments, the ADAM33 nucleic acid is a mouse ADAM33 transcript. In some embodiments, the mouse ADAM33 transcript is of the sequence set forth in GenBank NCBI Reference Sequence: NM_033615.2.

In some embodiments, the present disclosure provides an antisense compound having a target-recognition sequence that is sufficiently complementary to an equal length portion of an ADAM33 transcript as set forth in GenBank NCBI Reference Sequence: NM_001282447.2 (incorporated herein as SEQ ID NO:1). In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the ADAM33 transcript as set forth in SEQ ID NO:1. In some embodiments, the antisense compound comprises a target-recognition sequence that is perfectly complementary to an equal length portion of the ADAM33 transcript as set forth in SEQ ID NO:1.

In some embodiments, the present disclosure provides an antisense compound having a target-recognition sequence that is sufficiently complementary to an equal length portion of an ADAM33 transcript as set forth in GenBank NCBI Reference Sequence: NM_025220.4 (incorporated herein as SEQ ID NO:2). In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the ADAM33 transcript as set forth in SEQ ID NO:2. In some embodiments, the antisense compound comprises a target-recognition sequence that is perfectly complementary to an equal length portion of the ADAM33 transcript as set forth in SEQ ID NO:2.

In some embodiments, the present disclosure provides an antisense compound having a target-recognition sequence that is sufficiently complementary to an equal length portion of an ADAM33 transcript as set forth in GenBank NCBI Reference Sequence: NM_153202.3 (incorporated herein as SEQ ID NO:3). In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the ADAM33 transcript as set forth in SEQ ID NO:3. In some embodiments, the antisense compound comprises a target-recognition sequence that is perfectly complementary to an equal length portion of the ADAM33 transcript as set forth in SEQ ID NO:3.

In some embodiments, the present disclosure provides an antisense compound having a target-recognition sequence that is sufficiently complementary to an equal length portion of an ADAM33 transcript as set forth GenBank NCBI Reference Sequence: NM_025220.3 (incorporated herein as SEQ ID NO:4). In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the ADAM33 transcript as set forth in SEQ ID NO:4. In some embodiments, the antisense compound comprises a target-recognition sequence that is perfectly complementary to an equal length portion of the ADAM33 transcript as set forth in SEQ ID NO:4.

In some embodiments, the present disclosure provides an antisense compound having a target-recognition sequence that is sufficiently complementary to an equal length portion of the 3' end of the open reading frame of an ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' end of the open reading frame of the ADAM33 transcript as set forth in SEQ ID NO:1. In some embodiments, the antisense compound comprises a target-recognition sequence that is perfectly complementary to an equal length portion of the 3' end of the open reading frame of the ADAM33 transcript as set forth in SEQ ID NO:1. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' end of the open reading frame of the ADAM33 transcript as set forth in SEQ ID NO:2. In some embodiments, the antisense compound comprises a target-recognition sequence that is perfectly complementary to an equal length portion of the 3' end of the open reading frame of the ADAM33 transcript as set forth in SEQ ID NO:2. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' end of the open reading frame of the ADAM33 transcript as set forth in SEQ ID NO:3. In some embodiments, the antisense compound comprises a target-recognition sequence that is perfectly complementary to an equal length portion of the 3' end of the open reading frame of the ADAM33 transcript as set forth in SEQ ID NO:3. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' end of the open reading frame of the ADAM33 transcript as set forth in SEQ ID NO:4. In some embodiments, the antisense compound comprises a target-recognition sequence that is perfectly complementary to an equal length portion of the 3' end of the open reading frame of the ADAM33 transcript as set forth in SEQ ID NO:4.

In some embodiments, the present disclosure provides an antisense compound having a target-recognition sequence that is sufficiently complementary to an equal length portion of the 5' end of the open reading frame of an ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' end of the open reading frame of the ADAM33 transcript as set forth in SEQ ID NO:1. In some embodiments, the antisense compound comprises a target-recognition sequence that is perfectly complementary to an equal length portion of the 5' end of the open reading frame of the ADAM33 transcript as set forth in SEQ ID NO:1. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' end of the open reading frame of the ADAM33 transcript as set forth in SEQ ID NO:2. In some embodiments, the antisense compound comprises a target-recognition sequence that is perfectly complementary to an equal length portion of the 5' end of the open reading frame of the ADAM33 transcript as set forth in SEQ ID NO:2. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' end of the open reading frame of the ADAM33 transcript as set forth in SEQ ID NO:3. In some embodiments, the antisense compound comprises a target-recognition sequence that is perfectly complementary to an equal length portion of the 5' end of the open reading frame of the ADAM33 transcript as set forth in SEQ ID NO:3. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' end of the open reading frame of the ADAM33 transcript as set forth in SEQ ID NO:4. In some embodiments, the antisense compound comprises a target-recognition sequence that is perfectly complementary to an equal length portion of the 5' end of the open reading frame of the ADAM33 transcript as set forth in SEQ ID NO:4.

In some embodiments, the present disclosure provides an antisense compound having a target-recognition sequence that is sufficiently complementary to an equal length portion of the 3' untranslated region of an ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' untranslated region of the ADAM33 transcript as set forth in SEQ ID NO:1. In some embodiments, the antisense compound comprises a target-recognition sequence that is perfectly complementary to an equal length portion of the 3' untranslated region of the ADAM33 transcript as set forth in SEQ ID NO:1. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' untranslated region of the ADAM33 transcript as set forth in SEQ ID NO:2. In some embodiments, the antisense compound comprises a target-recognition sequence that is perfectly complementary to an equal length portion of the 3' untranslated region of the ADAM33 transcript as set forth in SEQ ID NO:2. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' untranslated region of the ADAM33 transcript as set forth in SEQ ID NO:3. In some embodiments, the antisense compound comprises a target-recognition sequence that is perfectly complementary to an equal length portion of the 3' untranslated region of the ADAM33 transcript as set forth in SEQ ID NO:3. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 3' untranslated region of the ADAM33 transcript as set forth in SEQ ID NO:4. In some embodiments, the antisense compound comprises a target-recognition sequence that is perfectly complementary to an equal length portion of the 3' untranslated region of the ADAM33 transcript as set forth in SEQ ID NO:4.

In some embodiments, the present disclosure provides an antisense compound having a target-recognition sequence that is sufficiently complementary to an equal length portion of the 5' untranslated region of an ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' untranslated region of the ADAM33 transcript as set forth in SEQ ID NO:1. In some embodiments, the antisense compound comprises a target-recognition sequence that is perfectly complementary to an equal length portion of the 5' untranslated region of the ADAM33 transcript as set forth in SEQ ID NO:1. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' untranslated region of the ADAM33 transcript as set forth in SEQ ID NO:2. In some embodiments, the antisense compound comprises a target-recognition sequence that is perfectly complementary to an equal length portion of the 5' untranslated region of the ADAM33 transcript as set forth in SEQ ID NO:2. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' untranslated region of the ADAM33 transcript as set forth in SEQ ID NO:3. In some embodiments, the antisense compound comprises a target-recognition sequence that is perfectly complementary to an equal length portion of the 5' untranslated region of the ADAM33 transcript as set forth in SEQ ID NO:3. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of the 5' untranslated region of the ADAM33 transcript as set forth in SEQ ID NO:4. In some embodiments, the antisense compound comprises a target-recognition sequence that is perfectly complementary to an equal length portion of the 5' untranslated region of the ADAM33 transcript as set forth in SEQ ID NO:4.

In some embodiments, the present disclosure provides an antisense compound having a target-recognition sequence that is sufficiently complementary to a conserved region of an ADAM33 transcript, e.g., of a human ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of a conserved region of the ADAM33 transcript as set forth in SEQ ID NO:1. In some embodiments, the antisense compound comprises a target-recognition sequence that is perfectly complementary to an equal length portion of a conserved region of the ADAM33 transcript as set forth in SEQ ID NO:1. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of a conserved region of the ADAM33 transcript as set forth in SEQ ID NO:2. In some embodiments, the antisense compound comprises a target-recognition sequence that is perfectly complementary to an equal length portion of a conserved region of the ADAM33 transcript as set forth in SEQ ID NO:2. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of a conserved region of the ADAM33 transcript as set forth in SEQ ID NO:3. In some embodiments, the antisense compound comprises a target-recognition sequence that is perfectly complementary to an equal length portion of a conserved region of the ADAM33 transcript as set forth in SEQ ID NO:3. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of a conserved region of the ADAM33 transcript as set forth in SEQ ID NO:4. In some embodiments, the antisense compound comprises a target-recognition sequence that is perfectly complementary to an equal length portion of a conserved region of the ADAM33 transcript as set forth in SEQ ID NO:4.

In some embodiments, the present disclosure provides an antisense compound having a target-recognition sequence that is sufficiently complementary to a conserved region of a non-human (e.g., non-human primate, rodent, etc.) ADAM33 transcript. In some embodiments, the antisense compound comprises a target-recognition sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to an equal length portion of a conserved region of a non-human (e.g., non-human primate, rodent, etc.) ADAM33 transcript. In some embodiments, the antisense compound comprises a target-recognition sequence that is perfectly complementary to an equal length portion of a conserved region of a non-human (e.g., non-human primate, rodent, etc.) ADAM33 transcript.

In certain embodiments, the present disclosure provides an antisense oligonucleotide targeting a human ADAM33 transcript, having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

(SEQ ID NO: 5)
5'-T$_s$G$_s$A$_s$t$_s$c$_s$c$_s$g$_s$t$_s$g$_s$t$_s$g$_s$g$_s$T$_s$T$_s$G-3'

(SEQ ID NO: 6)
5'-A$_s$T$_s$G$_s$a$_s$t$_s$c$_s$c$_s$g$_s$t$_s$g$_s$t$_s$g$_s$G$_s$T$_s$T-3'

(SEQ ID NO: 7)
5'-A$_s$A$_s$T$_s$g$_s$a$_s$t$_s$c$_s$c$_s$g$_s$t$_s$g$_s$t$_s$G$_s$G$_s$T-3'

-continued

5'-C$_s$A$_s$A$_s$t$_s$g$_s$a$_s$t$_s$c$_s$c$_s$g$_s$t$_s$g$_s$T$_s$G$_s$G-3' (SEQ ID NO: 8)

5'-T$_s$G$_s$T$_s$c$_s$a$_s$t$_s$g$_s$g$_s$t$_s$t$_s$t$_s$c$_s$C$_s$A$_s$G-3' (SEQ ID NO: 9)

5'-G$_s$G$_s$T$_s$g$_s$t$_s$c$_s$a$_s$t$_s$g$_s$g$_s$t$_s$t$_s$T$_s$T$_s$C-3' (SEQ ID NO: 10)

5'-A$_s$G$_s$G$_s$t$_s$g$_s$t$_s$c$_s$a$_s$t$_s$g$_s$g$_s$t$_s$T$_s$T$_s$T-3' (SEQ ID NO: 11)

5'-T$_s$C$_s$A$_s$t$_s$t$_s$t$_s$t$_s$a$_s$g$_s$g$_s$a$_s$g$_s$C$_s$T$_s$A-3' (SEQ ID NO: 12)

5'-T$_s$T$_s$C$_s$a$_s$t$_s$t$_s$t$_s$t$_s$a$_s$g$_s$g$_s$a$_s$G$_s$C$_s$T-3' (SEQ ID NO: 13)

5'-T$_s$G$_s$T$_s$t$_s$c$_s$a$_s$t$_s$t$_s$t$_s$a$_s$g$_s$G$_s$A$_s$G-3' (SEQ ID NO: 14)

5'-T$_s$C$_s$C$_s$g$_s$t$_s$g$_s$g$_s$a$_s$a$_s$a$_s$t$_s$G$_s$C$_s$A-3' (SEQ ID NO: 15)

wherein an 's' denotes a phosphorothioate linkage, an upper-case letter denotes a linked nucleotide (LNA), and a lower case letter denotes a deoxyribonucleotide. In certain embodiments, the present disclosure provides an antisense oligonucleotide having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence as set forth in any of SEQ ID NOs:5-15. In some embodiments, an antisense oligonucleotide of the present disclosure comprises a nucleic acid sequence with at least 90% sequence identity to the nucleic acid sequence set forth in any one of SEQ ID NOs:5-15. In some embodiments, an antisense oligonucleotide of the present disclosure comprises a nucleic acid sequence with at least 95% sequence identity to the nucleic acid sequence set forth in any one of SEQ ID NOs:5-15.

In some embodiments, the present disclosure provides an antisense oligonucleotide targeting a mouse ADAM33 transcript, having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

5'-T$_s$G$_s$A$_s$t$_s$c$_s$c$_s$g$_s$t$_s$g$_s$t$_s$g$_s$g$_s$T$_s$T$_s$G-3' (SEQ ID NO: 5)

5'-A$_s$G$_s$G$_s$c$_s$a$_s$t$_s$c$_s$t$_s$c$_s$g$_s$g$_s$t$_s$T$_s$T$_s$G-3' (SEQ ID NO: 55)

5'-T$_s$A$_s$A$_s$g$_s$c$_s$t$_s$c$_s$a$_s$g$_s$a$_s$g$_s$t$_s$T$_s$C$_s$G-3' (SEQ ID NO: 56)

5'-G$_s$G$_s$T$_s$a$_s$a$_s$g$_s$c$_s$t$_s$c$_s$a$_s$g$_s$a$_s$G$_s$T$_s$T-3' (SEQ ID NO: 57)

5'-T$_s$C$_s$T$_s$a$_s$t$_s$g$_s$a$_s$c$_s$a$_s$a$_s$c$_s$a$_s$G$_s$C$_s$T-3' (SEQ ID NO: 58)

wherein an 's' denotes a phosphorothioate linkage, an uppercase letter denotes a linked nucleotide (LNA), and a lower case letter denotes a deoxyribonucleotide. In certain embodiments, the present disclosure provides an antisense oligonucleotide targeting a mouse ADAM33 transcript, having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence as set forth in any of SEQ ID NOs:5 and 16-19.

Conjugated Antisense Compounds

Antisense compounds may be covalently linked to one or more moieties or conjugates which enhance the activity, cellular distribution or cellular uptake of the resulting antisense oligonucleotides. Antisense compounds may be covalently linked to one or more moieties or conjugates which enhance and/or optimize pharmacokinetic parameters. Various pharmacokinetic parameters are known to a person of ordinary skill in the art, for example, absorbance, concentration of a compound in the body, the degree to which a compound permeates the body, the rate of elimination/clearance of a compound, the volume of plasma cleared of a compound per unit time, and others.

Typical conjugate groups include cholesterol moieties and lipid moieties. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan etal, Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). For example, a lipid moiety based on 1-O-hexa-decyloxy-1,3-propanediol can be conjugated to an antisense compound of the present disclosure. Such a lipid moiety has previously been shown to increase small molecule uptake and improve the oral bioavailability of nucleoside drugs (see, e.g., Aldern et al., *Mol. Pharmacol.* 2003, 63:678-681; and Hostetler, *Antiviral Res.* 2009, 82:A84-A98). Additional conjugate groups include carbohydrates, phospholipids, biotin, phenazine, folate, phenanthridine, anthraquinone, acridine, fluoresceins, rhodamines, coumarins, and dyes. In some embodiments, conjugation of a ligand to an antisense compound allows recognition by cell-surface receptors (see, e.g., Wolfrum et al., *Nat. Biotechnol.* 2007, 25:1149-1157; Hostetler et al., *Antiviral Chem. Chemother.* 2001, 12:61-70; and Prakash et al., *Nucleic Acids Res.* 2014, 42:8796-807). Methods of attaching one or more moieties or conjugates are well known in the art.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In some embodiments, an antisense compound of the present disclosure comprises a conjugate. In one embodiment, an antisense compound of the present disclosure comprises a target-recognition sequence and a conjugate, wherein the conjugate is linked to the target-recognition sequence. In some embodiments, the conjugate is selected from any of the conjugates described herein, for example, a hydrophobic conjugate, a tissue-targeting conjugate, or a conjugate designed to optimize pharmacokinetic parameters. A hydrophobic conjugate useful for conjugating to antisense compounds of the present disclosure, includes a hexadecyloxypropyl conjugate, a cholesterol conjugate, a polyunsaturated fatty acid conjugate, and others known in the art that may improve cellular uptake of a conjugate antisense compound. In some embodiments, the conjugate may be a tissue-targeting conjugate, for example, a carbohydrate conjugate, or a peptide conjugate, or any conjugate known in the art that can target an antisense compound of the present disclosure to a specific tissue. In some embodiments, an antisense compound of the present disclosure is conjugated with a polyethylene glycol conjugate. In one embodiment, a polyethylene glycol conjugate antisense compound optimizes pharmacokinetic properties of the antisense compound.

In certain embodiments, the present disclosure provides a biostable antisense oligonucleotide having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

(SEQ ID NO: 5)
5'-$T_sG_sA_st_sc_sc_sg_st_sg_st_sg_sg_sT_sT_sG$-3'

(SEQ ID NO: 6)
5'-$A_sT_sG_sa_st_sc_sc_sg_st_sg_st_sg_sG_sT_sT$-3'

(SEQ ID NO: 7)
5'-$A_sA_sT_sg_sa_st_sc_sc_sg_st_sg_st_sG_sG_sT$-3'

(SEQ ID NO: 8)
5'-$C_sA_sA_st_sg_sa_st_sc_sc_sg_st_sg_sT_sG_sG$-3'

(SEQ ID NO: 9)
5'-$T_sG_sT_sc_sa_st_sg_sg_st_st_st_sC_sA_sG$-3'

(SEQ ID NO: 10)
5'-$G_sG_sT_sg_st_sc_sa_st_sg_sg_st_sT_sT_sC$-3'

(SEQ ID NO: 11)
5'-$A_sG_sG_st_sg_st_sc_sa_st_sg_sg_st_sT_sT_sT$-3'

(SEQ ID NO: 12)
5'-$T_sC_sA_st_st_st_st_sa_sg_sg_sa_sg_sC_sT_sA$-3'

(SEQ ID NO: 13)
5'-$T_sT_sC_sa_st_st_st_st_sa_sg_sg_sa_sG_sC_sT$-3'

(SEQ ID NO: 14)
5'-$T_sG_sT_st_sc_sa_st_st_st_st_sa_sg_sG_sA_sG$-3'

(SEQ ID NO: 15)
5'-$T_sC_sC_sg_st_sg_sg_sa_sa_sa_st_st_sG_sC_sA$-3' wherein an 's' denotes a phosphorothioate linkage, an uppercase letter denotes a linked nucleotide (LNA), and a lower case letter denotes a deoxyribonucleotide, and wherein the biostable antisense oligonucleotide comprises a hydrophobic conjugate terminal to the target-recognition sequence. In some embodiments, the hydrophobic conjugate is hexadecyloxypropyl (HOP). In such embodiments, the biostable antisense oligonucleotide having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

(SEQ ID NO: 16)
5'-(HOP)$_sT_sG_sA_st_sc_sc_sg_st_sg_st_sg_sg_sT_sT_sG$-3'

(SEQ ID NO: 17)
5'-(HOP)$_sA_sT_sG_sa_st_sc_sc_sg_st_sg_st_sg_sG_sT_sT$-3'

(SEQ ID NO: 18)
5'-(HOP)$_sA_sA_sT_sg_sa_st_sc_sc_sg_st_sg_st_sG_sG_sT$-3'

(SEQ ID NO: 19)
5'-(HOP)$_sC_sA_sA_st_sg_sa_st_sc_sc_sg_st_sg_sT_sG_sG$-3'

(SEQ ID NO: 20)
5'-(HOP)$_sT_sG_sT_sc_sa_st_sg_sg_st_st_st_sC_sA_sG$-3'

(SEQ ID NO: 21)
5'-(HOP)$_sG_sG_sT_sg_st_sc_sa_st_sg_sg_st_sT_sT_sC$-3'

(SEQ ID NO: 22)
5'-(HOP)$_sA_sG_sG_st_sg_st_sc_sa_st_sg_sg_st_sT_sT_sT$-3'

(SEQ ID NO: 2$_s$)
5'-(HOP)$_sT_sC_sA_st_st_st_st_sa_sg_sg_sa_sg_sC_sT_sA$-3'

(SEQ ID NO: 24)
5'-(HOP)$_sT_sT_sC_sa_st_st_st_st_sa_sg_sg_sa_sG_sC_sT$-3'

(SEQ ID NO: 25)
5'-(HOP)$_sT_sG_sT_st_sc_sa_st_st_st_st_sa_sg_sG_sA_sG$-3'

(SEQ ID NO: 26)
5'-(HOP)$_sT_sC_sC_sg_st_sg_sg_sa_sa_sa_st_st_sG_sC_sA$-3' wherein an 's' denotes a phosphorothioate linkage, an uppercase letter denotes a linked nucleotide (LNA), a lower case letter denotes a deoxyribonucleotide, and (HOP) denotes a hexadecyloxypropyl conjugate. In certain embodiments, the present disclosure provides a biostable antisense oligonucleotide having a target-recognition sequence that comprises a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence as set forth in any of SEQ ID NOs:16-26. In some embodiments, a biostable antisense oligonucleotide of the present disclosure comprises a nucleic acid sequence with at least 90% sequence identity to the nucleic acid sequence set forth in any one of SEQ ID NOs:16-26. In some embodiments, a biostable antisense oligonucleotide of the present disclosure comprises a nucleic acid sequence with at least 95% sequence identity to the nucleic acid sequence set forth in any one of SEQ ID NOs:16-26.

In some embodiments, the present disclosure provides a biostable antisense compound. In one embodiment, the biostable antisense compound comprises a target-recognition sequence and a conjugate, wherein the conjugate is linked to the target-recognition sequence. In some embodiments, the conjugate of a conjugated antisense compound remains stably linked to the antisense compound after cellular internalization. In one embodiment, the conjugate of a conjugate antisense compound remains stably linked to the target-recognition sequence after cellular internalization.

In some embodiments, the present disclosure provides biocleavable analogues of antisense oligonucleotides described herein. In such cases, biocleavable analogues comprise a hydrophobic conjugate that leads to stronger association with cell membranes and a linker. In one embodiment, the linker is a cleavable linker that when cleaved, releases the antisense oligonucleotide, e.g., releases the antisense oligonucleotide into endosomes. In some embodiments, an antisense compound comprises a cleavable linker, wherein the cleavable linker degrades when cleaved. In some embodiments, the linker is a nuclease-cleavable linker comprising a phosphodiester linkage. In some embodiments, the nuclease-cleavable linker comprising a phosphodiester linkage is about 2 to about 8 nucleotides. For example, a nuclease-cleavable phosphodiester linker can be 3, 4, 5, 6, 7, 8 nucleotides in length, or longer, e.g., 9, 10, 11, 12, 13, 14, 15, 16, 17, 18 nucleotides in length, or longer. In one embodiment, the nuclease-cleavable linker comprises about 6 nucleotides. In some embodiments, the cleavable linker is cleaved after cellular internalization. In some embodiments, the cleavable linker is cleaved within an endosome. In some embodiments, the cleavable linker is cleaved under reducing conditions. In some embodiments, the cleavable linker is cleaved under changing pH conditions, for example the cleavable linker is cleaved when the pH decreases, or when the pH increases. In some embodiments, the cleavable linker is cleaved by an intracellular nuclease or protease. In some embodiments, the cleavable linker is cleaved by an endosomal nuclease or protease.

In certain embodiments an antisense oligonucleotide of the present disclosure is a biocleavable antisense oligonucleotide comprising a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

(SEQ ID NO: 27)
5'-(HOP)tttttt$T_s$$G_s$$A_s$$t_s$$c_s$$c_s$$g_s$$t_s$$g_s$$t_s$$g_s$$g_s$$T_s$$T_s$$G$-3'

(SEQ ID NO: 28)
5'-(HOP)tttttt$A_s$$T_s$$G_s$$a_s$$t_s$$c_s$$c_s$$g_s$$t_s$$g_s$$t_s$$g_s$$G_s$$T_s$T-3'

(SEQ ID NO: 29)
5'-(HOP)tttttt$A_s$$A_s$$T_s$$g_s$$a_s$$t_s$$c_s$$c_s$$g_s$$t_s$$g_s$$t_s$$G_s$$G_s$T-3'

(SEQ ID NO: 30)
5'-(HOP)tttttt$C_s$$A_s$$A_s$$t_s$$g_s$$a_s$$t_s$$c_s$$c_s$$g_s$$t_s$$g_s$$T_s$$G_s$G-3'

(SEQ ID NO: 31)
5'-(HOP)tttttt$T_s$$G_s$$T_s$$c_s$$a_s$$t_s$$g_s$$g_s$$t_s$$t_s$$t_s$$t_s$$C_s$$A_s$G-3'

(SEQ ID NO: 32)
5'-(HOP)tttttt$G_s$$G_s$$T_s$$g_s$$t_s$$c_s$$a_s$$t_s$$g_s$$g_s$$t_s$$t_s$$T_s$$T_s$C-3'

(SEQ ID NO: 33)
5'-(HOP)tttttt$A_s$$G_s$$G_s$$t_s$$g_s$$t_s$$c_s$$a_s$$t_s$$g_s$$g_s$$t_s$$T_s$$T_s$T-3'

(SEQ ID NO: 34)
5'-(HOP)tttttt$T_s$$C_s$$A_s$$t_s$$t_s$$t_s$$t_s$$a_s$$g_s$$g_s$$a_s$$g_s$$C_s$$T_s$A-3'

(SEQ ID NO: 35)
5'-(HOP)tttttt$T_s$$T_s$$C_s$$a_s$$t_s$$t_s$$t_s$$t_s$$a_s$$g_s$$g_s$$a_s$$G_s$$C_s$T-3'

(SEQ ID NO: 36)
5'-(HOP)tttttt$T_s$$G_s$$T_s$$t_s$$c_s$$a_s$$t_s$$t_s$$t_s$$t_s$$a_s$$g_s$$G_s$$A_s$G-3'

(SEQ ID NO: 37)
5'-(HOP)tttttt$T_s$$C_s$$C_s$$g_s$$t_s$$g_s$$g_s$$a_s$$a_s$$a_s$$t_s$$t_s$$G_s$$C_s$A-3' wherein an 's' denotes a phosphorothioate linkage, an upper-case letter denotes a linked nucleotide (LNA), a lower case letter denotes a deoxyribonucleotide, and (HOP) denotes a hexadecyloxypropyl conjugate. In certain embodiments, the present disclosure provides a biocleavable antisense oligonucleotide comprising a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence as set forth in any of SEQ ID NOs:27-37. In some embodiments, a biocleavable antisense oligonucleotide of the present disclosure comprises a nucleic acid sequence with at least 90% sequence identity to the nucleic acid sequence set forth in any one of SEQ ID NOs:27-37. In some embodiments, a biocleavable antisense oligonucleotide of the present disclosure comprises a nucleic acid sequence with at least 95% sequence identity to the nucleic acid sequence set forth in any one of SEQ ID NOs:27-37.

Pharmaceutical Compositions and Formulations

Provided herein are pharmaceutical compositions and formulations which include the antisense compounds described herein. For example, the antisense oligonucleotides described herein can be admixed, encapsulated, conjugated or otherwise associated with other molecules, molecule structures or mixtures of compounds. A pharmaceutical composition of the invention is formulated to be compatible with its intended route of administration. Examples of routes of administration include oral administration, mucosal administration, subcutaneous administration, intramuscular administration, topical administration, intravenous administration, intrathecal administration, intracerebroventricular administration, or inhalation. Examples of routes of administration include parenteral, e.g., intravenous, intradermal, subcutaneous, intraperitoneal, intramuscular, oral (e.g., inhalation), transdermal (topical), and transmucosal administration.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions can be administered in a number of ways depending on, for example, whether local or systemic treatment is desired and/or the area to be treated. In one embodiment, administration is topical to the surface of the respiratory tract, particularly nasal and pulmonary, e.g., by nebulization, inhalation, or insufflation of powders, solutions, gels, or aerosols (e.g., drops or sprays), by mouth and/or nose. For example, in some embodiments, a once-daily inhaler or a once-weekly nebulized formulation can be used. For administration by inhalation, the compounds are delivered in the form of an aerosol spray from pressured container or dispenser which contains a suitable propellant, e.g., a gas such as carbon dioxide, or a nebulizer.

The pharmaceutical compositions and formulations provided herein can, in some embodiments, be conveniently presented in unit dosage form and can be prepared according to conventional techniques well known in the pharmaceutical industry. Such techniques can include bringing into association the active ingredients with the pharmaceutical carrier(s) or excipient(s). In general, the formulations can be prepared by uniformly and intimately bringing into association the active ingredients with liquid carriers, finely divided solid carriers, or both, and then, if necessary, shaping the product (e.g., into a specific particle size for delivery). In one embodiment, the pharmaceutical formulations are prepared for pulmonary administration in an appropriate solvent, e.g., water or normal saline, and optionally in a sterile formulation with carriers or other agents to allow for the formation of droplets of the desired diameter for delivery using inhalers, nasal delivery devices, nebulizers, and other devices for pulmonary delivery. Alternatively, the pharmaceutical formulations can be formulated as dry powders for use in dry powder inhalers.

In some embodiments of the compositions (e.g., pharmaceutical compositions or formulations) provided herein, the synthetic antisense oligonucleotide is formulated to be administered by systemic administration. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In other embodiments, the synthetic antisense oligonucleotide is formulated to be administered by local administration. In some embodiments, the synthetic antisense oligonucleotide is formulated to be administered by intranasal, intratracheal, sublingual, aerosol and/or respiratory administration. In other embodiments, the synthetic antisense oligonucleotide is administered by insufflation or as a nasal spray or nasal gel. In other embodiments, the synthetic antisense oligonucleotide is formulated to be administered using a nebulizer, nasal inhaler, metered dose inhaler, dry powder inhaler, pulmonary inhaler, or a combination thereof.

The compounds can also be prepared in the form of suppositories (e.g., with conventional suppository bases such as cocoa butter and other glycerides) or retention enemas for rectal delivery.

An agent of the present disclosure, e.g., an antisense compound targeting an ADAM33 transcript can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

An agent of the present disclosure, e.g., an antisense compound targeting an ADAM33 transcript can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

An antisense compound targeted to an ADAM33 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ADAM33 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound.

Methods of Treatment

The present disclosure provides a method of treating a subject having an ADAM33-related disorder. Methods of treatment include administering to the subject in need thereof an effective amount of an antisense compound described herein. In some embodiments, the antisense compound comprises a target-recognition sequence that is sufficiently complementary to an ADAM33 nucleic acid (e.g., an ADAM33 transcript) to direct cleavage of the ADAM33 nucleic acid by RNase H.

Methods of treating a subject having an ADAM33-related disorder are useful in treating any ADAM33-related disorder known to those of ordinary skill in the art. For example, an ADAM33-related disorder includes, without limitation, e.g., a respiratory disease, a skin disease, a cardiovascular disease (e.g., atherosclerosis), an immune disease (e.g., systemic lupus erythematosus), and a cancer or tumor, or any combination thereof.

In some embodiments, a method of treating an ADAM33-related disorder is useful in treating a subject having an ADAM33-related respiratory disease known to those of ordinary skill in the art. For example, an ADAM33-related respiratory disease includes, without limitation, asthma, chronic obstructive pulmonary disease, pulmonary fibrosis, bronchial disease, respiratory infection, interstitial lung disease, sarcoidosis, rhinitis, and any cancerous lesion of the respiratory tract, or any combination thereof. In one embodiment, a method of treating an ADAM33-related disorder is useful in treating a subject having asthma. In one embodiment, a method of treating an ADAM33-related disorder is useful in reversing/preventing airway remodeling and/or airway inflammation and/or airway hyperresponsiveness. In one embodiment, airway remodeling is inflammation-dependent. In one embodiment, airway remodeling is inflammation-independent. For example, see, Davies et al., *JCI Insight* (2016) 1(11):e87632.

In some embodiments, a method of treating an ADAM33-related disorder is useful in treating a subject having an ADAM33-related skin disease known to those of ordinary skill in the art. For example, an ADAM33-related skin disease includes, without limitation, psoriasis, keloids, and dermatitis, or any combination thereof.

In some embodiments, a method of treating an ADAM33-related disorder is useful in treating a subject having an ADAM33-related cancer or tumor known to those of ordinary skill in the art. For example, an ADAM33-related cancer or tumor includes, without limitation, gastric cancer, glioblastoma, lung cancer, breast cancer, laryngeal carcinoma, bronchial carcinoma, nasal polyps, and sinonasal papilloma, or any combination thereof.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present invention is further illustrated by the following examples which should not be construed as further limiting.

Example 1: Materials and Methods

General Methods:

$^1$H, $^{13}$C, $^{31}$P NMR spectra were recorded on Bruker DPX or Bruker AV NMR spectrometers operating at 400, 101 and 162 MHz respectively. Small molecules were analyzed using a Waters (Manchester, UK) TQD mass spectrometer equipped with a triple quadrupole analyzer. Samples were introduced to the mass spectrometer via an Acquity UPC$^2$ system including a UPC$^2$ Waters HSS C18 SB column (100 mm×3.0 mm 1.8 µm) Gradient 90% $CO_2$:10% methanol modifier (25 mM ammonium acetate) to 60% $CO_2$:40% methanol modifier (25 mM ammonium acetate) in 3 min at a flow rate of 1.5 mL/min. The make-up flow (methanol/1% formic acid) was pumped at a flow rate of 0.45 mL/min into the mass spectrometer. Mass spectra were recorded using positive ion electrospray ionization.

Oligonucleotides:

The first set of siRNAs for sequence screening was purchased from Integrated DNA Technologies (Leuven). All other oligonucleotides were synthesized in-house at a 1 µmol scale on Applied Biosystems 394 DNA/RNA synthesizers with Unylinker (ChemGenes) or nucleoside-loaded CPG supports and standard detritylation and capping reagents. Activation was achieved with 5-Benzylthio-1H-Tetrazole (BTT, 0.3M in acetonitrile). Oxidation was achieved using 0.02 M iodine in THF/water/pyridine. Sulfurization was accomplished with the 1,2,4-dithiazolines EDITH (Link Technologies) or DTT (0.1M, ChemGenes). RNA, 2'F-RNA and 2'OMe-RNA phosphoramidites (ChemGenes) were dissolved to a concentration of 0.15M in anhydrous acetonitrile immediately prior to use. LNA and MOE phosphoramidites were synthesized by standard methods from 3'-hydroxyl precursors (Rasayan) using 2-cyanoethyloxy(N,N-diisopropylamino)phosphonamidic chloride and were used at 0.1 or 0.15 M in acetonitrile, with the exception of LNA 5-MeC (all "LNA-C" is actually LNA 5-Me-C) which was dissolved in a 3:1 mixture of THF:acetonitrile. Coupling times for all modified phosphoramidites were 10 minutes.

Unmodified RNA was deprotected using a 3:1 ratio of $NH_4OH$/EtOH for 48 hours at room temperature. The RNA 2'OH tert-butyldimethylsilyl protecting group was removed with a 4:1 DMSO/TEA.3HF solution at 65° C. for 3 hours. The reaction was cooled to room temperature then precipitated by the addition of 3M NaOAc (25 µL) and BuOH (1 mL). The mixture was centrifuged at 4° C. for 5 minutes at 8000 rpm, washed with 70% EtOH, air dried, and the pellet was resuspended in RNase-free water. 2'-modified RNA, LNA and DNA were deprotected with concentrated $NH_4OH$ at 55° C. overnight.

Oligonucleotides were evaporated to dryness by rotary evaporation then resuspended in 1 mL RNase-free water. If LCMS and analytical PAGE (see below) indicated that the oligomer was sufficiently pure, it was desalted with a Nap-10 column (GE Healthcare) and used directly. All oligonucleotides were characterized on Bruker MicrOTOF Ultimate 3000 or Agilent Q-TOF LCMS systems with electrospray ionization and time of flight analysis, using negative ionization mode.

20 µM working stocks of siRNAs were prepared by annealing the sense and antisense strands in a final 2.5×PBS buffer. The solutions were heated at 95° C. for 10 minutes and then cooled to room temperature at a rate of 1° C. per minute.

Oligonucleotide Purification and Electrophoresis:

Approximately 20 $A_{260}$ units (preparative gel) or 0.1 $A_{260}$ units (analytical gel) was loaded into a 20% polyacrylamide gel containing 7M urea and run at 400V for ~3 hours. Analytical gels were visualized using Stains-All (Sigma). For preparative gels, the product band was briefly visualized by UV shadowing, excised from the gel and incubated in RNase-free water overnight. The aqueous solution was then concentrated by rotary evaporator, resuspended in RNase-free water, and desalted via a Nap-25 column (GE Healthcare). The desalted oligonucleotide was evaporated to dryness again and resuspended in a small volume of RNase-free water.

Hexadecyloxypropyl-conjugated oligonucleotides were purified by ion exchange chromatography using an Agilent 1200-series HPLC, an Agilent PL-SAX column, and eluents containing 30% aqueous acetonitrile with increasing sodium perchlorate.

Cell Culture and Transfection:

MRC-5 embryonic fibroblasts were maintained at 37° C. and 5% $CO_2$ in DMEM supplemented with 10% FBS, 2% L-Glutamine, 1% NEAA, and 1% sodium pyruvate (all from Sigma). Cells were plated in 6-well plates at 150,000 cells/well (cationic lipid) or 25 k cell/well (gymnotic) 24 hours prior to transfection, unless otherwise stated. Mouse embryonic fibroblasts (MEFs) were maintained in DMEM supplemented with 10% FBS and were plated in 6-well plates at 100 k cells/well 24 hours prior to transfection.

Oligonucleotides were transfected at 50 nM concentration for single dose or decreasing doses for dose responses. Cells were transfected using RNAiMAX (Life Technologies) using 0.75 µL lipid per 1 µL of oligonucleotide (siRNA) or 0.67 µL per 1 µL oligonucleotide (LNA) in OptiMEM (Life Technologies). Gymnotic delivery was achieved using 1 µM or 3 µM oligonucleotide concentration in full cell culture media. Cells were harvested for RNA analysis 3 days after transfection (lipid) or 7 days post treatment (gymnotic) unless otherwise stated.

RNA Harvest and Quantitative Real-Time PCR (qRT-PCR):

Total RNA from cells was harvested 3 days post transfection (lipid transfection) or 7 days post transfection (gymnotic) unless otherwise stated. After washing each well with 1 mL PBS, 1 mL of RiboZol (Amresco) was added to each well, incubated for 2 min at room temperature and transferred to 1.5-mL microcentrifuge tube. Chloroform (200 µL) was added to each tube and the mixture was shaken vigorously for 1 minute then incubated at room temperature for 10 minutes. The mixture was centrifuged at 13,000 rpm for 20 min, and then the clear aqueous layer was transferred to a new 1.5-mL tube, avoiding any interphase. 2-propanol (600 µL) was added to the aqueous layer followed by a 1-min vigorous shake then a 20-min incubation at −20° C. followed by a 15-min centrifugation at 14 k rpm at 4° C. The resulting pellet was washed with ice cold 70% ethanol, re-centrifuged at 8000 rpm for 10 min at 4° C., and then briefly allowed to air dry. The pellet was resuspended in RNase-free water, heated to 55° C. for 5 min, then was quantitated by UV spectroscopy.

1 µg of RNA was treated with 2 units of DNase I (Worthington Biochemical Corporation) for 10 min at 37° C. followed by 10 min at 75° C. RNA was reverse transcribed using a High Capacity cDNA Reverse Transcription Kit (Life Technologies) per manufacturer's protocol.

qRT-PCR was performed using iTaq Supermix (BioRad) on a BioRad CFX96 real time system. Data were normalized relative to levels of GAPDH mRNA. A primer/probe assay (IDT) specific for the ADAM33 3'-untranslated region was used (unless otherwise stated): forward primer, 5'-GGCCTCTGCAAACAAACATAATT-3' (SEQ ID N0:38); reverse primer, 5'-GGGCTCAGGAAC-CACCTAGG-3' (SEQ ID N0:39); probe, 5'-CTTCCTGTTTCTTCCCACCCTGTCTTCTCT-3' (SEQ ID N0:40). GAPDH primer/probe assay (IDT); forward primer, 5'-TGGTCCAGGGGTCTTACT-3' (SEQ ID N0:41); reverse primer, 5'-CCTCAACGACCACTTTGT-3' (SEQ ID N0:42); probe, 5'-CTCAT-TTCCTGGTATGACAACGAATTTGGC-3' (SEQ ID N0:43). For mouse Adam33 mRNA quantitation, the TaqMan (ThermoFisher) probe set Mm00459697_g1 was used. All qRT-PCR experiments were performed in technical replicates. The qRT-PCR cycle was as follows: 95° C. for 7 minutes; (95° C. for 15 seconds; 60° C. for 30 seconds)×40 cycles.

Dynamic Light Scattering:

The lyophilized gapmer ASO (33-0) and its hexadecyloxypropyl conjugate (33-O biostable conjugate) were dissolved in RNase-free water at a concentration of 20 nM and filtered with 0.2 um filter prior to measurement. The filtered samples were then transferred to a 384-well microplate and placed into a DynaPro PlateReader-II system (WYATT Technology) for DLS measurement. The data was collected by averaging 10 measurements (~5 s each) for each sample.

2-cyanoethyl β-(hexadecyloxy)propyl) diisopropylphosphoramidite 3-(Hexadecyloxy)propan-1-ol was synthesized in one step according to the method of Yamano, Y. et al., *Biorg. Med. Chem.* (2012) 20:3658-3665 and recrystallized from hexane. The crystalline product (200 mg, 0.67 mmol) was dissolved in dry $CH_2Cl_2$ and diisopropylethylamine (0.70 mL, 2.68 mmol, 4 equiv) was added while stirring at RT. 2-Cyanoethyloxy(N,N-diisopropylamino) phosphonamidic chloride (0.18 mL, 0.8 mmol, 1.2 eq) was added dropwise and the solution was stirred for 45 min. After completion 15 mL of $CH_2Cl_2$ were added and the organic phase was washed with saturated aqueous $NaHCO_3$ and dried over $MgSO_4$. The crude product was purified on a silica column with Hex:EtOAc:$NEt_3$ 50:50:1 as eluent to afford the title compound as a colorless liquid (175 mg, 52% yield). $R_f$ in EtOAc=0.28. MS (ESI): found 501 (M+H); mass expected for ($C_{28}H_{57}N_2O_3P$+H=501.4). $^1$H NMR (400 MHz, $CDCl_3$) δ 0.89 (t, J=6.85 Hz, 3H, C$\underline{H}_3$CH$_2$) 1.19 (dd, J=6.72, 3.42 Hz, 12H, 2 (C$\underline{H}_3$)$_2$CHN) 1.26 (s, 26H, 13 (C$\underline{H}_2$)$_n$) 1.56 (quin, J=6.94 Hz, 2H, OCH$_2$C$\underline{H}_2$CH$_2$) 1.88 (quin, J=6.30 Hz, 2H, POCH$_2$C$\underline{H}_2$CH$_2$O) 2.64 (t, J=6.60 Hz, 2H, C$\underline{H}_2$CN) 3.40 (t, J=6.66 Hz, 2H, OC$\underline{H}_2$CH$_2$CH$_2$) 3.50 (t, J=6.30 Hz, 2H, POCH$_2$CH$_2$C$\underline{H}_2$O) 3.54-3.65 (m, 2H, 2 C$\underline{H}$) 3.65-3.79 (m, 2H, POC$\underline{H}_2$CH$_2$CH$_2$O) 3.79-3.93 ppm (m, 2H, POC H$_2$CH$_2$CN). $^{13}$C NMR (101 MHz, $CDCl_3$) δ 14.1 (s, 1C, $\underline{C}H_3$CH$_2$) 20.3 (d, J=6.60 Hz, 1C, $\underline{C}H_2$CN) 22.7 (s, 1C, CH$_2$ $\underline{C}H_2$CH$_3$) 24.5 and 24.63 (2 d, J=7.70 Hz, 2×2C, ($\underline{C}H_3$)$_2$CHN) 26.2 (s, 1C, OCH$_2$CH$_2$$\underline{C}H_2$) 29.3 (s, 1C$\underline{H}_{2n}$) 29.5 (s, 1C$\underline{H}_{2n}$) 29.6 (s, 2C$\underline{H}_{2n}$) 29.6 (s, 1C$\underline{H}_{2n}$) 29.7 (s, 5C$\underline{H}_{2n}$) 29.8 (s, 1C$\underline{H}_{2n}$) 31.5 (d, J=7.34 Hz, 1C, POCH$_2$ $\underline{C}H_2$CH$_2$O) 31.9 (s, 1C$\underline{H}_{2n}$) 43.0 (d, J=11.74 Hz, 2C, 2 CH) 58.3 (d, J=19.07 Hz, 1C, PO$\underline{C}H_2$CH$_2$CN) 60.7 (d, J=17.61 Hz, 1C, PO$\underline{C}H_2$CH$_2$CH$_2$O) 67.3 (s, 1C, POCH$_2$CH$_2$$\underline{C}H_2$O) 71.1 (s, 1C, O$\underline{C}H_2$CH$_2$CH$_2$), 117.6 ppm (s, 1C, $\underline{C}$N). $^{31}$P NMR (162 MHz, $CDCl_3$, $^1$H-decoupled) δ 147.56 ppm (s).

Example 2: ADAM33 Silencing by siRNAs and Ss-siRNAs

Four types of oligonucleotide-based gene silencing agents were compared for the inhibition of ADAM33/Adam33 (FIG. 1): (i) duplex siRNAs, (ii) chemically modified single-stranded siRNAs (ss-siRNAs) that operate by the RISC pathway, (iii) LNA gapmer antisense oligonucleotides (ASOs) operating via the RNase H mechanism, and (iv) novel bioclevable lipid conjugates of potent ASOs described herein (including biocleavable conjugates).

Figure 2B:
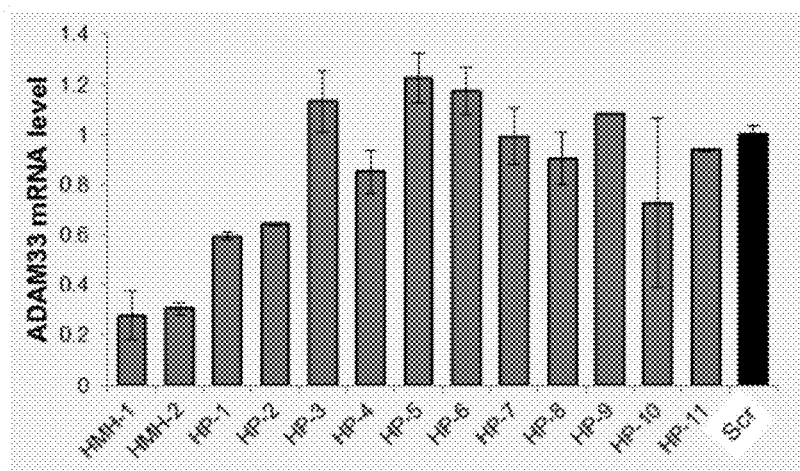

A panel of 13 duplex siRNAs targeting different regions of the ADAM33 transcript were designed and synthesized (FIG. 2A). The efficacy of these siRNAs were tested in MRC-5 human lung fibroblast cells, transfecting the siRNAs with a lipid transfection reagent and measuring silencing by qPCR. Most of the sequences were found to be inactive, while the most active duplexes were able to attain about 70% silencing (FIG. 2B).

Figure 2C:
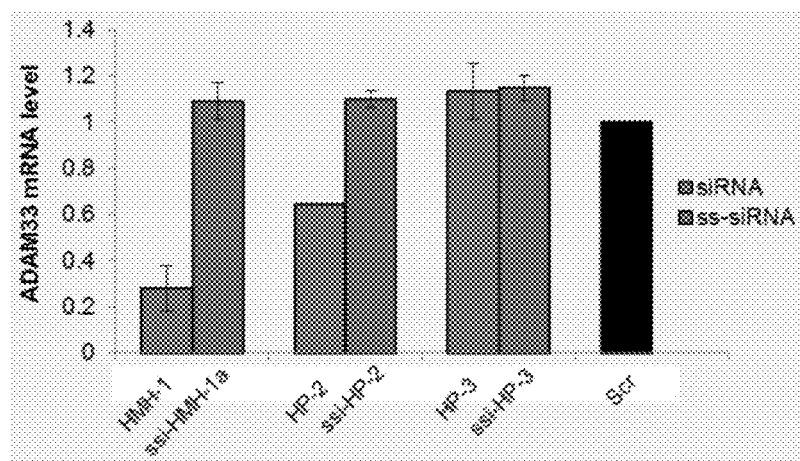
Figure 2D:
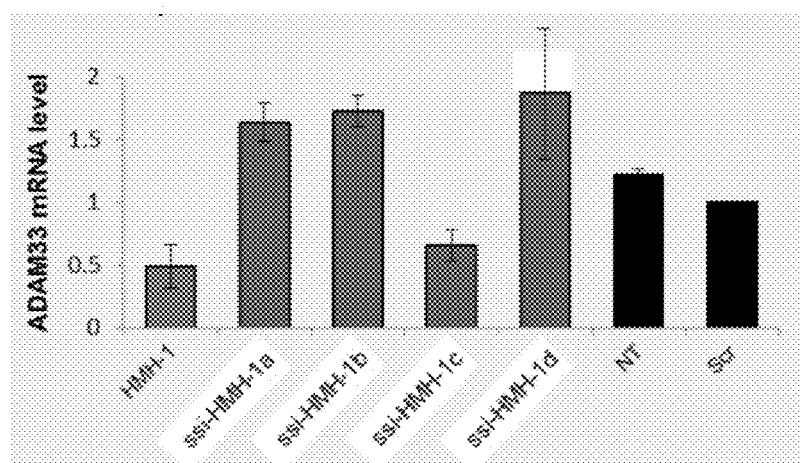

Single-stranded oligonucleotides can be recognized by the RNAi machinery and serve as guide strand, if the oligomer is stabilized to resist nuclease cleavage and contains a 5'-phosphate or phosphonate. To explore whether changing the biophysical properties of the RNAi trigger could improve activity, ss-siRNA analogues of three siRNA sequences were synthesized and tested: highly active sequence, HMH-1, moderately active sequence HP-2, and inactive sequence HP-3. The ss-siRNA analogues showed reduced efficacy (HMH1, HP-2) or maintained inactivity (HP-3, FIG. 2C). For the most active siRNA sequence HMH-1, a chemical optimization of the ss-siRNAs was carried out and one analogue was found with activity that was comparable but not superior to the parent duplex RNA (FIG. 2D). Only the ss-siRNA with 2'OMe-RNA modifications at the 3'-terminus was able to approach the potency of the duplex siRNA (ssi-HMH-1c, FIG. 2D). Neither siRNAs nor ss-siRNAs were able to surpass 70% silencing of the ADAM33 transcript under any of the conditions that were tested.

Example 3: LNA Gapmers Show High Potency when Transfected with a Cationic Lipid

Figure 3B:
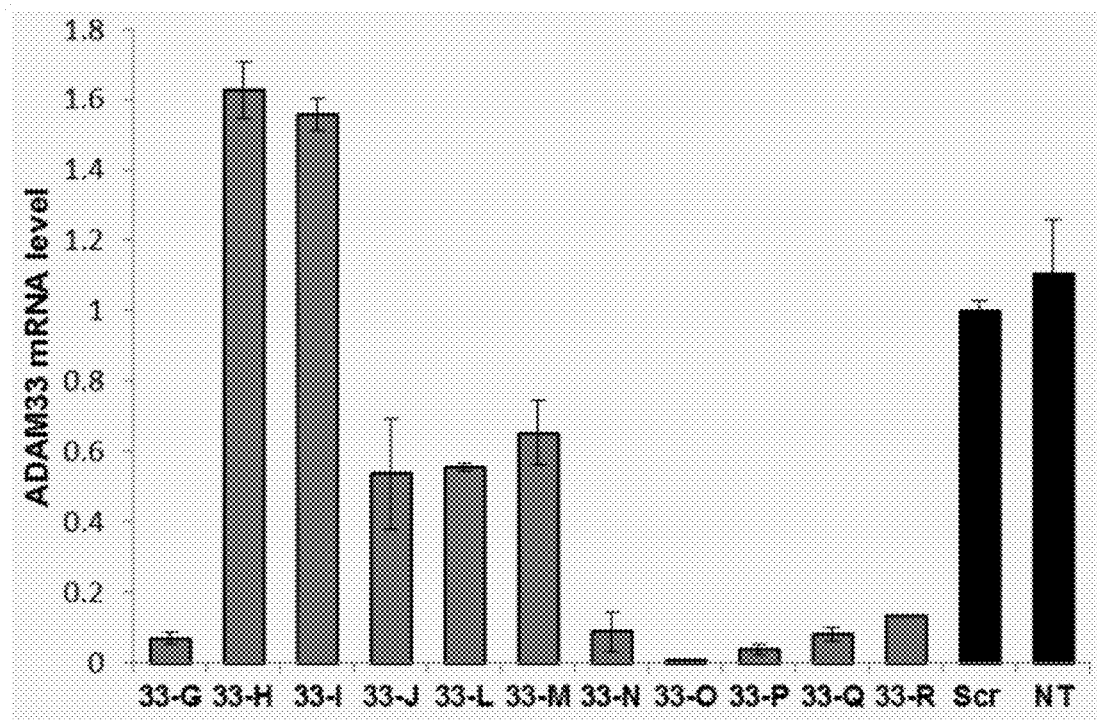
Figure 3C:
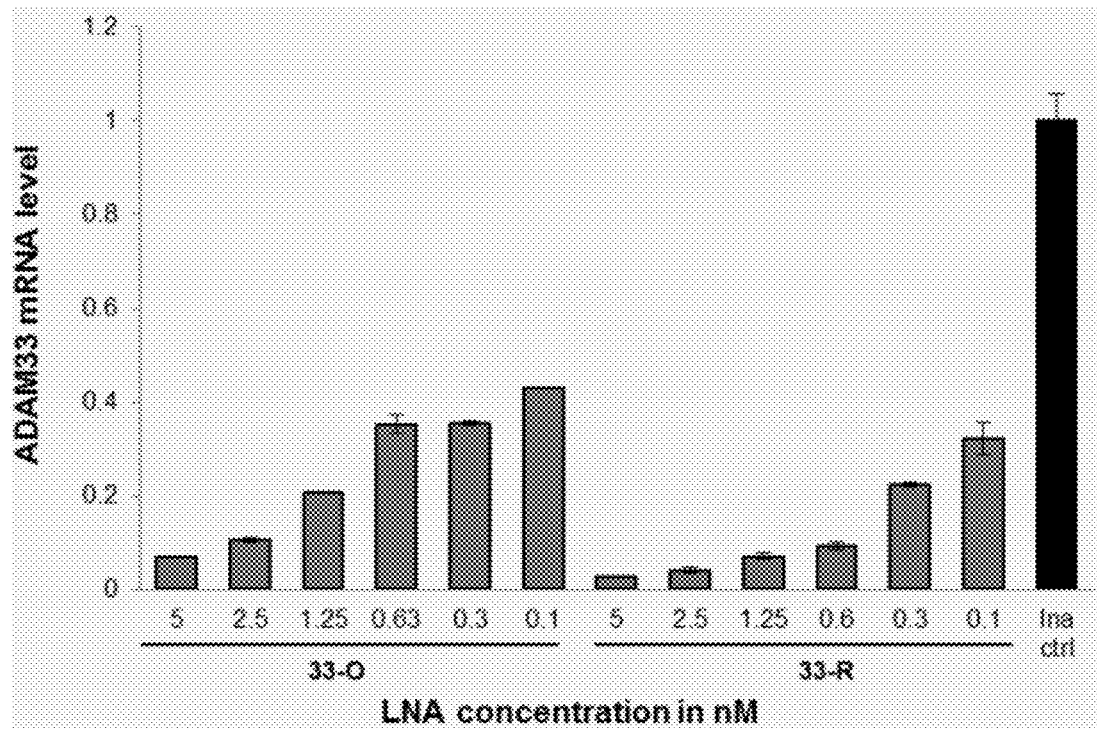

Another major class of single stranded gene silencing oligonucleotides are gapmer antisense oligonucleotides (ASOs). Gapmer ASOs operate through a different mechanism than the siRNAs and ss-siRNAs above: they recruit RNase H to cleave target mRNAs. Twelve phosphorothioate (PS) locked nucleic acid (LNA) 3-9-3 gapmers targeting various regions of ADAM33 mRNA were designed and synthesized (FIG. 3A). The LNA gapmers were tested at 50 nM concentration in MRC-5 fibroblasts using Lipofectamine RNAiMAX as transfection agent. LNAs 33-G, 33-N, 33-O, 33-P, 33-Q, and 33-R all achieved >80% silencing of ADAM33 when normalized to a scrambled siRNA duplex control (FIG. 3B). These very high hit rates and maximal efficacies contrasted sharply with the low hit rates and maximal efficacies observed when using RISC dependent oligonucleotides (siRNAs and ss-siRNAs) for this target. Furthermore, a dose response analysis showed potent, dose-dependent ADAM33 inhibition for 33-O and 33-R to concentrations <0.16 nM (FIG. 3C).

Example 4: Gymnotic Delivery of LNA Gapmers

Ex vivo lung tissue and in vivo lung experiments require oligonucleotides with the ability to exert potent silencing without the use of transfection agents, which can be toxic. Naked LNA or 2'-fluoroarabinonucleic acid (2'F-ANA) gapmers can be taken up by most types of dividing cells in culture in a process termed "gymnosis." Gymnotic delivery does not require serum additives or transfection reagents. It tends to show low toxicity and shows an improved correlation between in vitro and in vivo results.

The gymnotic approach was adopted to test: (a) if the LNA gapmers could enter the MRC-5 cells without the use of transfection agents; (b) how the potency of the LNA gapmers delivered via gymnotic delivery compared to the transfections using a cationic lipid; and (c) whether the gymnotically delivered LNA gapmers were toxic to cultured cells.

Figure 4A:
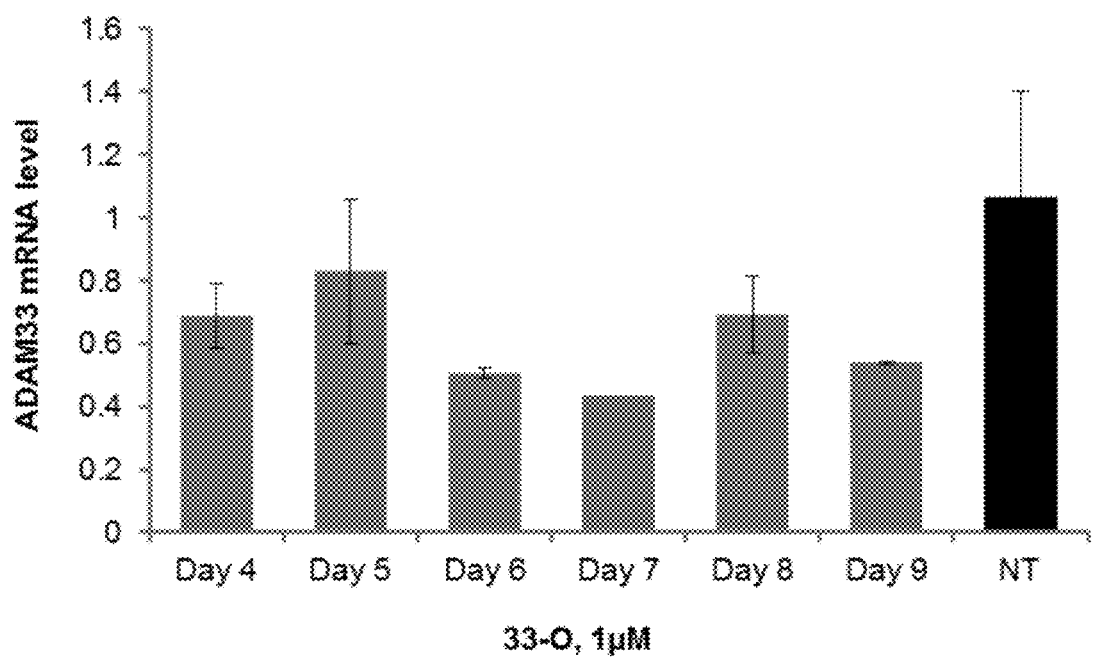
FIG. 4A-FIG. 4B show that gymnotically delivered gapmers are potent inhibitors of ADAM33.
Figure 4B:
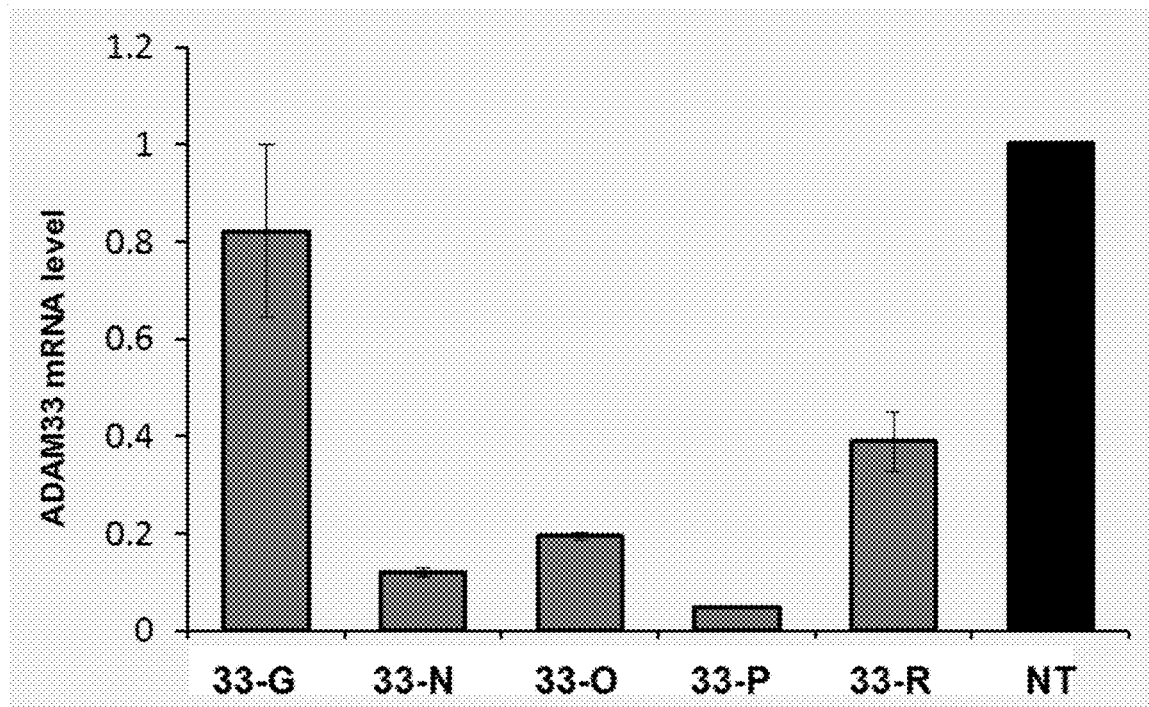

A time course experiment was performed gymnotically delivering 33-0 into MRC-5 cells at a 1 µM dose to determine the optimal day to harvest the cells after treatment, between day 4 and day 9. Results indicate that day 7 post-treatment was an appropriate time to harvest cells (FIG. 4A). LNA gapmers 33-G, N, O, P, and R were then selected for further testing. Oligomers 33-N, O, and P achieved >80% reduction of ADAM33 transcript levels, while 33-R showed 60% ADAM33 silencing at a 3 µM dose (FIG. 4B).

The LNA gapmers were able to efficiently silence ADAM33 expression without the aid of transfection agents. The gymnotically delivered LNAs showed no toxicity to cultured cells (based on phenotype and cell confluence).

Example 5: Hexadecyloxypropyl Conjugates for Cellular Uptake

The use of oligonucleotides as therapeutic agents may be impeded due to relatively poor uptake into most cells. One solution is the covalent attachment of a ligand that allows recognition by cell-surface receptors. A lipid moiety based on 1-O-hexa-decyloxy-1,3-propanediol, which has been previously shown to increase small molecule uptake by MRC-5 fibroblast cells and improve the oral bioavailability of nucleoside drugs, was attached to the LNA gapmers to improve uptake.

Figure 5A:
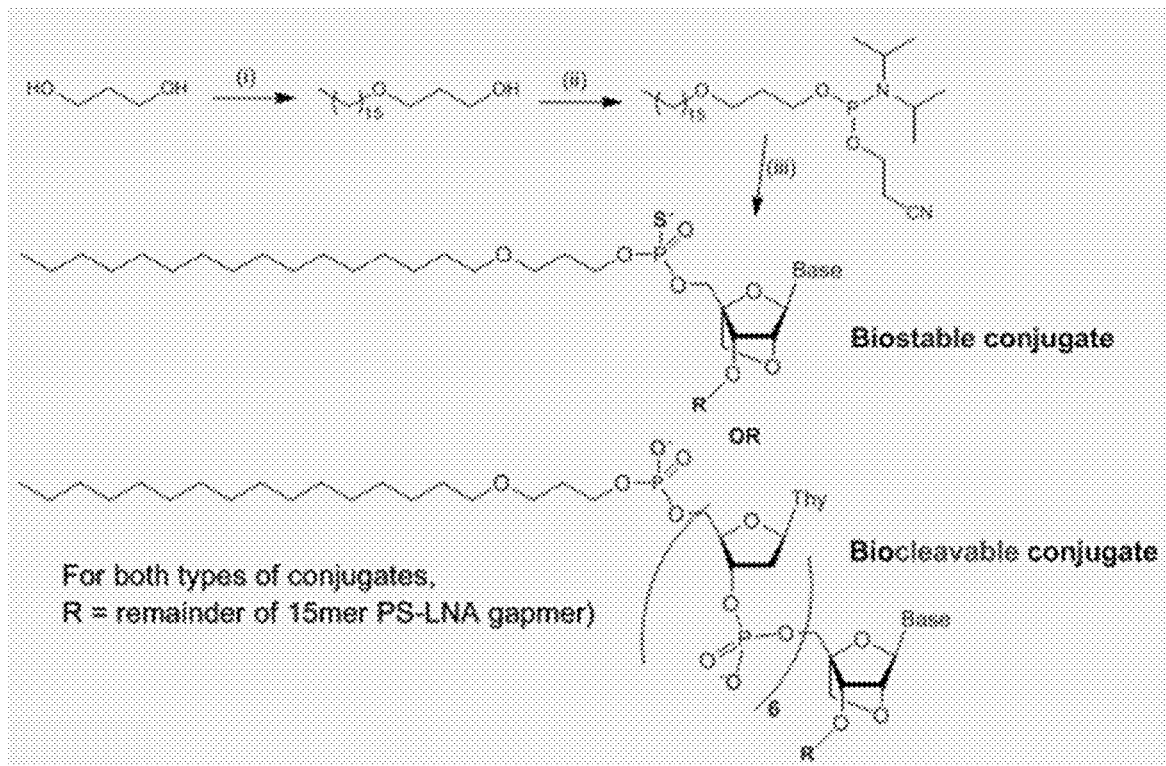

A 1-O-hexadecylpropanediol phosphoramidite was synthesized in two steps (FIG. 5A). Treatment of propanediol in dimethylformamide with sodium hydride followed by addition of hexadecyl bromide and catalytic potassium iodide gave 1-O-hexadecyl-1,3,-propanediol in a single step; recrystallisation with hexane yielded white crystals of excellent purity. The phosphoramidite was synthesized under standard conditions using 2-cyanoethyloxy(N,N-diisopropylamino)phosphonamidic chloride. The phosphoramidite was then conjugated to the 5'-end of LNA gapmers 33-N, O, and P via solid phase synthesis (FIG. 5A).

Without intending to be bound by scientific theory, in addition to direct recognition of cell-surface receptors by conjugated small molecules, conjugation approaches may also change the biophysical properties of the oligonucleotide which may affect their cell uptake in a more indirect way. For example, a variety of amphiphilic oligonucleotide conjugates have been shown to assemble into micelle-type structures. Previous work has described very long polymer conjugates that induce self-assembly of oligonucleotides into clusters, as well as oligonucleotides with shorter hydrophobic tails that assemble around a liposomal core.

Figure 5B:
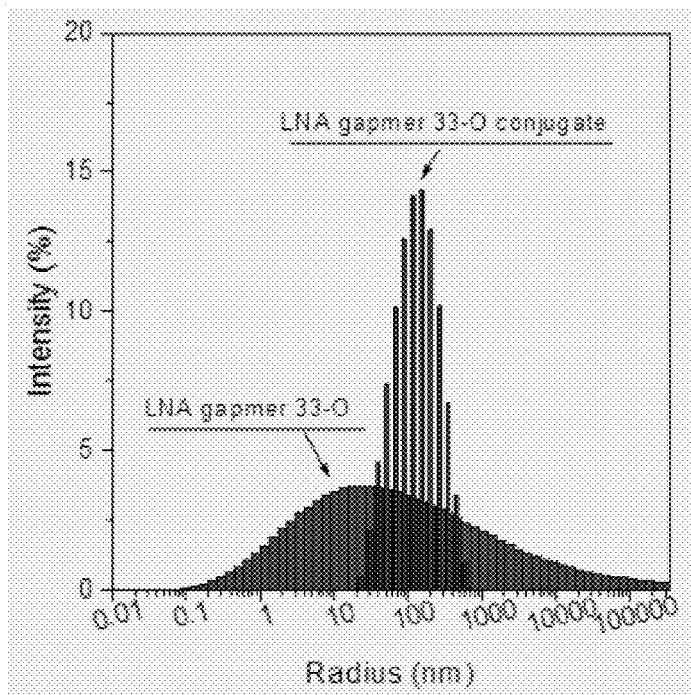

The conjugates were tested to see if they could self-assemble using dynamic light scattering. Indeed, it was found that conjugation of a hexadecyloxypropyl tail clearly induced assembly of oligonucleotides into clusters (FIG. 5B). This demonstrates that even a simple hydrophobic conjugate may be sufficient to induce efficient self-assembly into clusters/micelles.

Clustering/assembly of oligonucleotides often correlates with enhanced uptake and activity, across multiple size scales and likely via multiple mechanisms. In spite of the efficient self-assembly observed for the lipid tail conjugates, the biostable hexadecyloxypropyl conjugates showed reduced silencing efficacy in cells (FIG. 5C). A highly lipophilic tail might lead to stronger association with cell membranes but fails to release active oligonucleotide into the cytoplasm. Bioclevable analogues were generated based on a section of phosphodiester (PO)-linked DNA between the lipid tail and the phosphorothioate (PS) gapmer ASO (FIG. 5A). Nuclease cleavage at the PO linkages would allow release of the gapmer from the lipid tail inside endosomes. It was found that treatment of cells with these biocleavable constructs produced similar potency silencing of ADAM33 relative to the analogous unconjugated gapmers, but did not provide a potency advantage in vitro (FIG. 5C). Sequences of the biostable hexadecyloxypropyl conjugates and biocleavable analogues are provided in FIG. 5D. Hydrophobic conjugates of gapmer oligonucleotides may provide an advantage for tissue distribution or other in vivo properties, and data point to the importance of making hydrophobic conjugates in a biocleavable manner, to avoid any membrane entrapment and associated potency reduction.

Example 6: ASOs Designed to Homologous Regions of the Mouse ADAM33 Transcript are Also Active To explore the biological role of ADAM33/Adam33 in asthma progression, a series of mouse models have been developed. The mouse and human ADAM33/Adam33 transcripts are relatively well conserved in the coding region, but diverge substantially toward the 3'-end of the ORF and in their 3'-UTR sequences (for example, the mouse transcript has a much shorter UTR sequence than the human transcript).

Two of the active ASOs targeting the human ADAM33 transcript described herein also had significant sequence homology to the mouse transcript (G and N, Table 1). While the sequence conservation in the 3'-UTR was very poor, an analysis of the conservation of structural features was performed using T-coffee (see, Notredame, C. et al., *J. Mol. Biol.* (2000) 302:205-217), and targets were designed to regions of conserved structure (P and Q, near the end of the ORF, and R, in the 3'-UTR, Table 1).

TABLE 1

Design of mouse analogues of lead ASO sequences.

| Name | ASO Sequence | SEQ ID NO: |
|---|---|---|
| | 451              465 | |
| 33-G | TGATCCGTGTGGTTG | 44 |
| m33-G | TGATCCGTGTGGTTG | 45 |
| | 627              641 | |

TABLE 1-continued

Design of mouse analogues of lead ASO sequences.

| Name | ASO Sequence | SEQ ID NO: |
|---|---|---|
| | 2217              2231 | |
| 33-N | AGGTGTCATGGTTTT | 46 |
| m33-N | AGGCATCTCGGTTTG | 47 |
| | 2393              2407 | |
| | 2575              2589 | |
| 33-P | TCATTTTAGGAGCT | 48 |
| m33-P | TAAGCTCAGAGTTCG | 49 |
| | 2675              2689 | |
| | 2577              2591 | |
| 33-Q | TGTTCATTTTAGGAG | 50 |
| m33-Q | GGTAAGCTCAGAGTT | 51 |
| | 2677              2691 | |
| | 2929              2934 | |
| 33-R | TCCGTGGAAATTGCA | 52 |
| m33-R | TCTATGACAACAGCT | 53 |
| | 2876              2890 | |

In Table 1, numbers refer to the base numbering within the target transcripts (in each case human on top, mouse below). Bolded, underlined nucleotides in the mouse ASOs represents non-sequence-conserved residues relative to the human ASOs. While P, Q, and R showed only very modest sequence conservation, they showed a greater degree of structural conservation as predicted by T-coffee (see, Notredame, C. et al., *J. Mol. Biol.* (2000) 302:205-217). RefSeq accession numbers of the sequences used for alignments were as follows: human, NM_025220.3 (3573 nt total length, where the ORF ends at 2569); and mouse, NM_033615.2 (3165 nt total length, where the ORF ends at 2694).

Figures 6A, 6B:
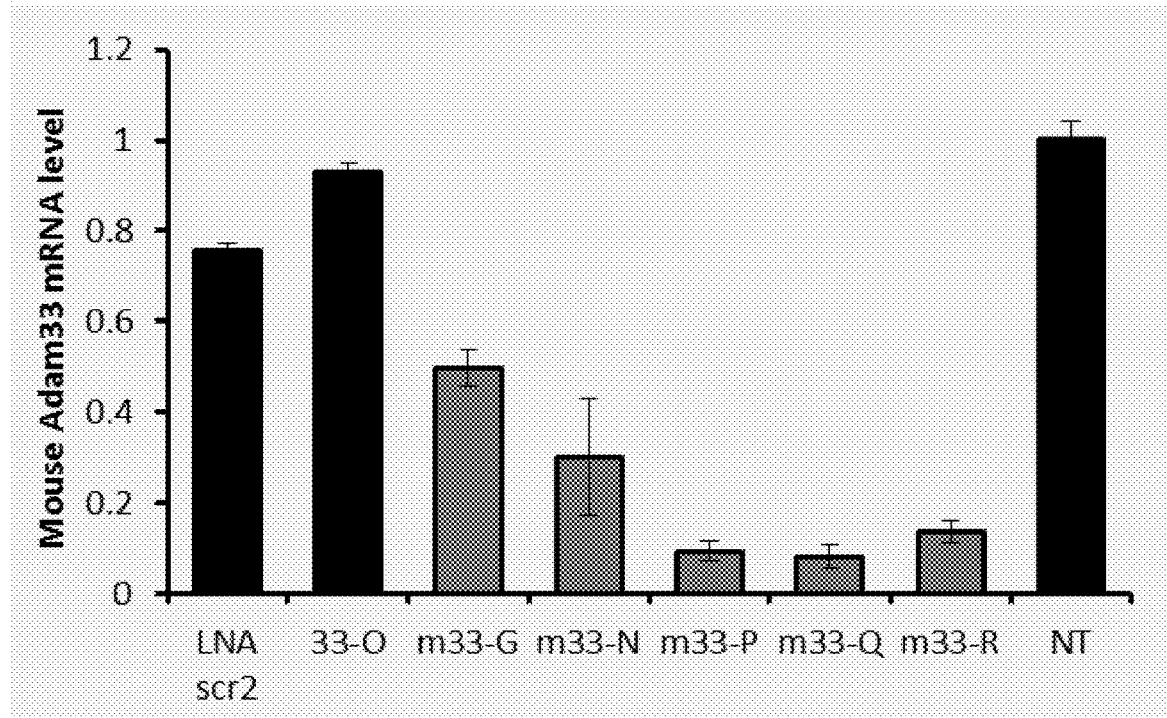
FIG. 6A-FIG. 6B show the identification of ASOs that provide highly effective silencing of mouse Adam33 expression in mouse embryonic fibroblasts.

These five sequences were synthesized as 3-9-3 LNA gapmers and tested for their ability to inhibit Adam33 expression in mouse embryonic fibroblasts (FIG. 6A). The most active ASOs in terms of silencing mouse Adam33 expression were those targeting the 3'-end of the ORF or the 3'-UTR (FIG. 6A), which were also the three sequences that were less well conserved relative to the human hits. Sequences of the five 3-9-3 LNA gapmers are provided in FIG. 6B.

What is claimed is:

1. A synthetic antisense oligonucleotide (ASO) or a pharmaceutically acceptable salt thereof comprising one or more single-stranded target-recognition sequences that are sufficiently complementary to an ADAM33 transcript to direct cleavage of the ADAM33 transcript by RNase H, wherein the target-recognition sequence comprises a formula A-B-C; wherein:

A comprises from about 0 to about 8 modified nucleotides;

B comprises from about 4 to about 18 deoxyribonucleic acid (DNA) nucleotides and/or DNA-like nucleotides; and C comprises from about 0 to about 8 modified nucleotides;

wherein at least one of the nucleotides of the ASO comprises a modified nucleotide;

wherein the modified nucleotide comprises a chemically modified sugar, a nucleobase, a phosphate linkage, or a mixture thereof;

wherein the overall length of the ASO is about 10 to about 30 nucleotides; and wherein the ASO comprises a nucleotide sequence comprising at least 70%-99% sequence identity to a nucleic acid sequence of any of the following: SEQ ID NOs: 6-15 or 55-58.

2. The ASO of claim 1 wherein the target-recognition sequence comprises a formula A-B-C, wherein:

A comprises from about 2 to about 6 modified nucleotides;

B comprises from about 6 to about 12 deoxyribonucleic acid (DNA) nucleotides and/or DNA-like nucleotides; and C comprises from about 2 to about 6 modified nucleotides.

3. The ASO of claim 1 wherein the modified nucleotide comprises:

a bicyclic nucleotide comprising a locked nucleotide, an ethyl-constrained nucleotide, an alpha-L-locked nucleic acid, a tricyclo-DNA, or any combination thereof;
a 2'-modified nucleotide comprising a 2'-O-methyl RNA, a 2'-O-methoxyethyl RNA, a 2'-fluoro RNA, or any combination thereof;
or a mixture thereof;
wherein the ASO further comprises a phosphorothioate linkage.

4. The ASO of claim 1, wherein the target-recognition sequence is at least 90% complementary to a portion of the ADAM33 transcript or is perfectly complementary to a portion of the ADAM33 transcript.

5. The ASO of claim 1, wherein the ASO further comprises a conjugate linked to the target-recognition sequence.

6. The ASO of claim 5, wherein:
the conjugate remains stably linked to the target-recognition sequence after cellular internalization.

7. The ASO of claim 6, wherein:
the nuclease-cleavable linker comprises from about 2 to about 8 nucleotides.

8. The ASO of claim 1, wherein the ADAM33 transcript is a human ADAM33 transcript.

9. A pharmaceutical composition comprising a synthetic antisense oligonucleotide (ASO) comprising one or more single-stranded target-recognition sequences that are sufficiently complementary to an ADAM33 transcript to direct cleavage of the ADAM33 transcript by RNase H and, a pharmaceutically acceptable carrier wherein the target-recognition sequence comprises a formula A-B-C;
wherein:
A comprises from about 0 to about 8 modified nucleotides;
B comprises from about 4 to about 18 deoxyribonucleic acid (DNA) nucleotides and/or DNA-like nucleotides; and
C comprises from about 0 to about 8 modified nucleotides;
wherein at least one of the nucleotides of the ASO comprises a modified nucleotide;
wherein the modified nucleotide comprises a chemically modified sugar, a nucleobase, a phosphate linkage, or a mixture thereof;
wherein the overall length of the ASO is about 10 to about 30 nucleotides; and
wherein the ASO comprises a nucleotide sequence comprising at least 70%-99% sequence identity to a nucleic acid sequence of any of the following: SEQ ID NOs: 6-15 or 55-58.

10. The composition of claim 9, wherein the modified nucleotide comprises:
a bicyclic nucleotide comprising a locked nucleotide, an ethyl-constrained nucleotide, an alpha-L-locked nucleic acid, and a tricyclo-DNA, or any combination thereof;
a 2'-modified nucleotide,
or a mixture thereof;
wherein the ASO further comprises a phosphorothioate linkage.

11. The composition of claim 9, wherein:
the ASO comprises a phosphorothioate linkage.

12. The composition of claim 9, wherein the ASO further comprises a conjugate linked to the target-recognition sequence.

13. The composition of claim 9, wherein the ASO further comprises a linker between the conjugate and the target-recognition sequence.

14. The composition of claim 9, wherein the ADAM33 transcript is a human ADAM33 transcript.

15. The ASO of claim 1, wherein the ASO binds the open reading frame of the ADAM33 transcript.

16. The ASO of claim 1, wherein the ASO binds a 5' or 3' untranslated region of the ADAM33 transcript.

17. The ASO of claim 1, wherein the ASO binds the junction between the open reading frame and the untranslated region of the ADAM33 transcript.

18. The ASO of claim 1, wherein the ASO binds a conserved region of the ADAM33 transcript.

19. The ASO of claim 1, wherein the ASO binds a region of the ADAM33 transcript containing a disease-associated single-nucleotide polymorphism.

20. The ASO of claim 1, wherein the target-recognition sequence comprises a nucleic acid sequence with at least 90% sequence identity to the nucleic acid sequence set forth in any one of SEQ ID NOs:6-15 or 55-58.

21. The ASO of claim 5, wherein the conjugate is selected from the group consisting of: a hydrophobic conjugate, a tissue-targeting conjugate, and a conjugate designed to optimize pharmacokinetic parameters.

22. The ASO of claim 21, wherein the hydrophobic conjugate is selected from the group consisting of a hexadecyloxypropyl conjugate, a cholesterol conjugate, and a polyunsaturated fatty acid conjugate.

23. The ASO of claim 21, wherein the tissue-targeting conjugate is selected from the group consisting of a carbohydrate conjugate, and a peptide conjugate.

24. The ASO of claim 21, wherein the conjugate designed to optimize pharmacokinetic parameters is a polyethylene glycol conjugate.

25. The ASO of claim 5, wherein the ASO comprises a biostable nucleic acid sequence with at least 90% sequence identity to the nucleic acid sequence set forth in any one of SEQ ID NOs:11-13.

26. The ASO of claim 5, wherein the ASO further comprises a linker between the conjugate and the target-recognition sequence.

27. The ASO of claim 26, wherein the linker is a cleavable linker.

28. The ASO of claim 27, wherein the cleavable linker degrades when cleaved, and/or the cleavable linker is a nuclease-cleavable linker comprising a phosphodiester linkage.

29. The ASO of claim 6, wherein the nuclease-cleavable linker comprises about 6 nucleotides.

30. The ASO of claim 6, wherein the cleavable linker is cleaved under reducing conditions or changing pH conditions.

31. The ASO of claim 6, wherein the cleavable linker is cleaved by an intracellular or endosomal nuclease.

32. The ASO of claim 6, wherein the cleavable linker is cleaved by an intracellular or endosomal protease.

33. The ASO of claim 6, wherein the ASO comprises a nucleic acid sequence with at least 90% sequence identity to the nucleic acid sequence set forth in any one of SEQ ID NOs:22-24.

34. The ASO of claim 1, wherein the ASO is capable of mediating cleavage of at least 80% of ADAM33 transcripts, or at least 90% of ADAM33 transcripts.

35. The composition of claim 10, wherein the 2'-modified nucleotide is selected from the group consisting of a 2'-O- methyl RNA, a 2'-O-methoxyethyl RNA, and a 2'-fluoro RNA, or any combination thereof.

36. The composition of claim 9, wherein the target-recognition sequence is at least 90% complementary to a portion of the ADAM33 transcript or is perfectly complementary to a portion of the ADAM33 transcript.

37. The composition of claim 36, wherein:
the ASO binds the open reading frame of the ADAM33 transcript;
the ASO binds a 5' or 3' untranslated region of the ADAM33 transcript;
the ASO binds the junction the open reading frame and the untranslated region of the ADAM33 transcript;
the ASO binds a conserved region of the ADAM33 transcript; and/or
the ASO binds a region of the ADAM33 transcript containing a disease-associated single-nucleotide polymorphism.

38. The composition of claim 36, wherein the target-recognition sequence comprises a nucleic acid sequence with at least 90% sequence identity to the nucleic acid sequence set forth in any one of SEQ ID NOs:6-15 or 55-58.

39. The composition of claim 12, wherein the conjugate is selected from the group consisting of:
a hydrophobic conjugate,
a tissue-targeting conjugate, and
a conjugate designed to optimize pharmacokinetic parameters.

40. The composition of claim 39, wherein the hydrophobic conjugate is hexadecyloxypropyl.

41. The composition of claim 9, wherein the ASO further comprises a conjugate linked to the target-recognition sequence and a biostable nucleic acid sequence with at least 90% sequence identity to the nucleic acid sequence set forth in any one of SEQ ID NOs:11-13.

42. The composition of claim 13, wherein the linker is a nuclease-cleavable linker comprising a phosphodiester linkage.

43. The composition of claim 42, wherein the nuclease-cleavable linker comprises about 6 nucleotides.

44. The composition of claim 9, wherein the ASO further comprises a linker between the conjugate and the target-recognition sequence.

45. The composition of claim 9, wherein the ASO comprises a nucleic acid sequence with at least 90% sequence identity to the nucleic acid sequence set forth in any one of SEQ ID NOs:22-24.

46. The composition of claim 9, wherein the pharmaceutical composition is formulated for oral administration, mucosal administration, subcutaneous administration, intramuscular administration, topical administration, intravenous administration, intrathecal administration, intracerebroventricular administration, or inhalation.

47. The composition of claim 9, wherein the pharmaceutical composition is formulated for inhalation.

48. The composition of claim 47, wherein the pharmaceutical composition formulated for inhalation is formulated as a powder.

* * * * *